United States Patent [19]
Hua et al.

[11] Patent Number: 5,958,970
[45] Date of Patent: Sep. 28, 1999

[54] TRICYCLIC AND TETRACYCLIC PYRONES

[75] Inventors: Duy H. Hua; Jean-Pierre Perchellet, both of Manhattan, Kans.

[73] Assignee: Kansas State University Research Foundation, Manhattan, Kans.

[21] Appl. No.: 08/902,053

[22] Filed: Jul. 29, 1997

Related U.S. Application Data

[63] Continuation-in-part of application No. 08/813,514, Mar. 7, 1997, abandoned.

[51] Int. Cl.$^6$ .......................... A61K 31/35; A61K 31/38; A61K 31/39; C07D 311/78; C07D 319/08; C07D 327/06; C07D 335/04; C07D 339/08

[52] U.S. Cl. .................. 514/455; 514/224.5; 514/229.8; 514/267; 514/287; 514/291; 514/292; 514/293; 514/338; 514/432; 514/434; 514/437; 514/452; 514/453; 514/454; 544/32; 544/34; 544/95; 544/250; 544/251; 546/64; 546/65; 546/80; 546/81; 546/82; 546/83; 546/89; 546/90; 546/92; 546/280.1; 546/282.4; 546/282.7; 546/283.1; 549/16; 549/17; 549/24; 549/25; 549/26; 549/27; 549/276; 549/282; 549/361; 549/383; 549/384; 549/387; 549/392; 549/393

[58] Field of Search ........................... 514/224.5, 229.8, 514/267, 287, 291, 292, 293, 338, 432, 437, 453, 454, 455, 434, 452; 544/32, 34, 95, 250, 251; 546/64, 65, 80, 81, 82, 83, 89, 90, 92, 280.1, 282.7, 283.1, 282.4; 549/25, 26, 27, 383, 384, 387, 392, 393, 16, 17, 24, 276, 282, 361

[56] References Cited

PUBLICATIONS

Hua, D.H. et al., "A One–Pot Condensation of Pyrones and Enals. Synthesis of 1H,7H–5a,6,8,9–Tetrahydro–1–oxopyrano[4,3–b][1]benzopyrans," *The Journal of Organic Chemistry* (Oct. 3, 1997) 62(20):6888–6896.

Perchellet, J.P. et al., "Antitumor Activity of Novel Tricyclic Pyrone Analogs in Murine Leukemia Cells in Vitro," *Anticancer Research* (Jul.–Aug. 1997) 17(4A):2427–2434.

Billheimer, J.T., "Cholesterol Acyltransferase," (1985) In *Methods in Enzymology* 111:286–293.

Cervera, M. et al., "4–Amino–6–methyl–2H–pyran–2–one, Preparation and Reactions with Aromatic Aldehydes," (1990) *Tetrahedron* 46:7885–7892.

Corey, E.J. and Erickson, B.W., "Oxidative hydrolysis of 1,3–dithiane derivatives to carbonyl compounds using N–halo(succinimide) reagents," (1971) *J. Org. Chem.* 36(3):3553–3560.

Ellman, G.L. et al., "A New and Rapid Colorimetric Determination of Acetylcholinesterase Activity," (1961)*Biochemical Pharmacology* 7:88–95.

Kim, Y.K. et al., "Pyripyropenes, Novel Inhibitors of Acyl–CoA:Cholesterol Acyltransferase Produced by *Aspergillus fumigatus* II. Structure Elucidation of Pyripyropenes A, B, C and D," (1994) *J. Antibiotics* 47:154–162.

Main, A.R. et al., "Purification of cholinesterase from horse serum," (1974) *Biochem. J.* 143:733–744.

Marzetta, C.A. et al. (1994), "Pharmacological properties of a novel ACAT inhibitor (CP–113,818) in cholesterol–fed rats, hamsters, rabbits, and monkeys," *J. Lipid Res.* 35:1829–1838.

Narasimhan, N.S. and Ammanamanchi, R., "Mechanism of acylation of dilithium salts of β–ketoesters: an efficient synthesis of anibine," (1983) *J. Org. Chem* 48:3945–3947.

Obata, R. et al., "Chemical modification and structure–activity relationships of pyripyropenes. 1. Modification at the four hydroxyl group," (1996) *J. Antibiotics* 49:1113–1148.

Omura, S., et al., "Arisugacin, a Novel and Selective Inhibitor of Acetylcholinesterase from Penicillium sp. FO–4259," (1995) *J. Antibiotics* 48:745–746.

Omura, S., et al., "Pyripyropenes, Highly Potent Inhibitors of Acyl–CoA; Cholesterol Acyltransferase Produced by *Aspergillus fumigatus*," (1993) *J. Antibiotics* 46:1168–1169.

Ralston, J.S. et al., "Acetylcholinesterase from Fetal Bovine Serum," (1985) *J. Biol. Chem.* 260:4312–4318.

Rinne, W.W. et al., "New methods of preparation of 2–methylcyclohexen–1–one," (1995) *J. Am. Chem. Soc.* 72:5759–5760.

Stotter, P.L. and Hill, K.A., "α Halocarbonyl Compounds. II. A Position–Specific Preparation of α–Bromo Ketones by Bromination of Lithium Enolates. A Position–Specific Introduction of α, β–Unsaturation into Unsymmetrical Ketones," (1973) *J. Org. Chem.* 38:2576–2578.

Tomoda, H., et al., "Relative and Absolute Stereochemistry of Pyripyropenes A, A Potent, Bioavailable Inhibitor of Acyl–CoA:Cholesterol Acyltransferase (ACAT)," (1994) *J. Am. Chem. Soc.* 116:12097–12098.

*Primary Examiner*—Richard L. Raymond
*Assistant Examiner*—Brenda Coleman
*Attorney, Agent, or Firm*—Greenlee, Winner and Sullivan, P.C.

[57] ABSTRACT

This invention provides cancer-active tricyclic and tetracyclic oxypyrones and a method of synthesizing these compounds. Preferred compounds have aryl groups at the 3-position of the oxypyrone ring. The tricyclic oxyprone synthetic method is a simple condensation reaction of pyrones with cyclohexenecarboxaldehydes, providing high yields and using few steps. The tetracyclic oxypyrone synthetic method is a simple condensation reaction of carvones with pyrones.

30 Claims, 14 Drawing Sheets

TRICYCLIC AND TETRACYCLIC PYRONES

This application is a continuation-in-part of U.S. application Ser. No. 08/813,514 filed Mar. 7, 1997, all aspects of which that do not conflict with this application are incorporated herein in their entirety.

GOVERNMENT FUNDING

This application was funded, at least in part, by a grant from the United States Government, which may have certain rights therein.

BACKGROUND OF THE INVENTION

It was recently discovered that arisugacin, a natural product isolated from a culture of Penicillium, is an inhibitor of acetylcholinesterase (AChE), and on this basis arisugacin has been predicted to be effective in the treatment of Alzheimer's disease. Related compounds also showed inhibitory activity. Omura, S., et al. (1995), "Arisugacin, a Novel and Selective Inhibitor of Acetylcholinesterase from Penicillium sp. FO-4259," J. Antibiotics 48:745–746. Arisugacin and the related compounds are tetracyclic pyrones (having four fused rings). Other tetracyclic pyrones, certain pyripyropenes, have been shown to be inhibitors of cholesterol acyltransferase (ACAT), and therefore have been predicted to be effective in the treatment of atherosclerosis and hypercholesterolemia. Omura, S., et al. (1993), "Pyripyropenes, Highly Potent Inhibitors of Acyl-CoA; Cholesterol Acyltransferase Produced by *Aspergillus fumigatus*," J. Antibiotics 46:1168–1169; and "Kim, Y. K. et al. (1994), "Pyripyropenes, Novel Inhibitors of Acyl-CoA:Cholesterol Acyltransferase Produced by *Aspergillus fumigatus*," J. Antibiotics 47:154–162. Pyripyropene A, one such inhibitor, is further characterized in Tomoda, H., et al. (1994), "Relative and Absolute Stereochemistry of Pyripyropene A, A Potent, Bioavailable Inhibitor of Acyl-CoA:Cholesterol Acyltransferase (ACAT)," J. Am. Chem. Soc. 116:12097–12098.

A number of multicyclic pyrones are known to the art and described in Chemical Abstracts; however, tricyclic and tetracycic pyrones as disclosed and claimed herein, appear not to have been previously described.

There is a need for simpler inhibitors of AchE and ACAT that are useful as treatments for Alzheimer's disease, atherosclerosis and hypercholesterolemia.

SUMMARY OF THE INVENTION

The tricyclic and tetracyclic pyrones of this invention are useful as inhibitors of AChE and ACAT, and can be used in the treatment of Alzheimer's disease, atherosclerosis and hypercholesterolemia. The tricyclic compounds are also potent inhibitors of cancer cell growth and macromolecule synthesis (e.g., DNA, RNA and protein synthesis) and can be used in the treatment of various forms of cancers including leukemia, ascites, and solid tumors. Further, their short-term inhibition of macromolecule synthesis is reversible following removal, but their long-term inhibition of tumor cell growth is not. Importantly, the tricyclic compounds are also powerful inhibitors of tubulin polymerization and may be useful as cell cycle-specific anticancer drugs. As hereinafter described, certain of these pyrones are useful intermediates in the synthesis of other pyrones of this invention. The tricyclic compounds are cytostatic but not overly cytotoxic.

The tricyclic pyrones of this invention include compounds selected from the group of compounds of the formula:

I.

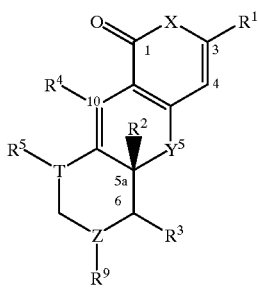

wherein:

T is independently CH, N, S or O;
X is independently O, NH or S;
Y is independently O, NH or S;
Z is independently CH, N, S or O;
$R^1$ is independently Formula I; or
$R^1$ and $R^3$ and $R^4$ and $R^5$ are, independently, H, OH, alkyl, alkenyl, alkynyl, an aromatic ring system,

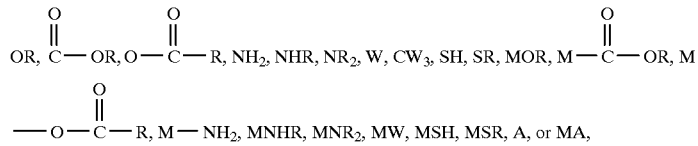

wherein R and M are independently H, alkyl, alkenyl or alkynyl, an aromatic ring system amino, amido, sulfhydryl, or sulfonyl, W is Cl, F, Br or OCl, and A is an aromatic ring system.

$R^2$ and $R^9$ are independently H or R where R is as defined above.

As used herein, the term "aromatic ring system" includes five and six-membered rings, fused rings, heterocyclic rings having oxygen, sulfur or nitrogen as a ring member, OR-substituted and R-substituted aromatic rings where R is defined as above. Preferably the substituents have one to five carbons. As used herein, the terms "alkyl," "alkenyl," an "alkynyl" include C1–C6 straight or branched chains. Unless otherwise specified, a general formula includes all stereoisomers.

Compounds of this invention also include compounds of the formula:

II.

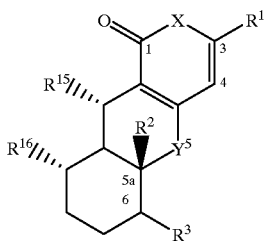

wherein:

X, Y and $R^2$–$R^3$ are as set forth for Formula I;

$R^1$ is independently Formula II or as set forth for Formula I;

$R^{15}$ is independently $NH_2$, OH, or OCOR where R is H, or alkyl;

$R^{16}$ is independently OH or H; and $R^{15}$ and $R^{16}$ taken together are O;

compounds of the formula:

III.

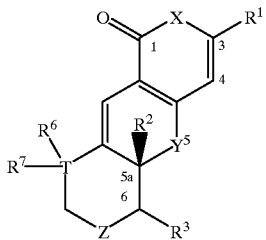

wherein:

X, Y, T, Z and $R^2$ and $R^3$ are as set forth for Formula I;

$R^1$ is independently Formula III or as set forth for Formula I; and $R^6$ is H when $R^7$ is OH, or $R^6$ is OH when $R^7$ is H, or $R^6$ and $R^7$ taken together are =O;

compounds of the formula:

IV.

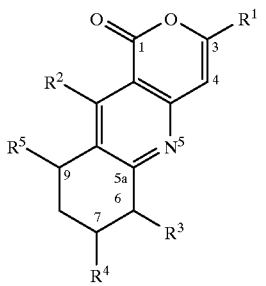

wherein $R^1$ is independently Formula IV or as set forth for Formula I, and $R^3$ is as set forth for Formula I above; and $R^2$, $R^4$ and $R^5$ are defined as $R^3$ for Formula I above; and compounds of the formula:

V.

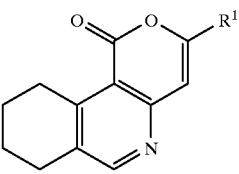

wherein $R^1$ is Formula V or independently is as set forth for Formula I above.

The tetracyclic pyrones of this invention include compounds selected from the group of compounds of the formula:

VI.

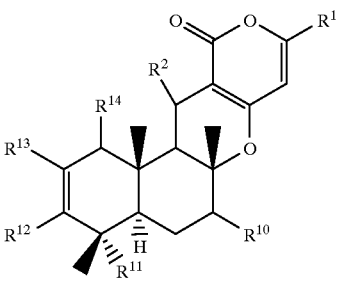

wherein:

$R^1$ and $R^2$ are independently as defined as $R^3$ as set forth for Formula I above;

$R^{10}$ and $R^{11}$ and $R^{13}$ and $R^{14}$ are independently defined as $R^3$ as set forth for Formula I above; and $R^{12}$ is H, alkyl, alkenyl or alkynyl, an aromatic ring system, amino, amido, sulfhydryl, or sulfonyl.

A preferable class of compounds of this invention useful as macromolecule synthesis inhibitors in cancer cells are compounds selected from compounds of the formula:

1.

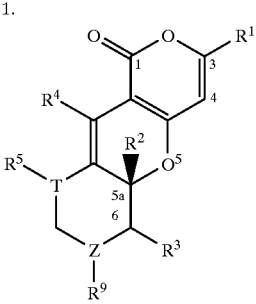

wherein:

$R^1$ is independently selected from the group consisting of H, R, 3-pyridyl, R-substituted 3-pyridyl, phenyl, R-substituted, di-substituted and tri-substituted phenyl, O—R-substituted, di-substituted and tri-substituted phenyl where R is as defined above; and preferably comprises an aromatic ring;

$R^2$ and $R^9$ are independently selected from the group consisting of H and R, where R is as defined above;

$R^3$, $R^4$ and $R^5$ are independently selected from the group H, R, OH, OCHO, and OR where R is as defined above; and T and Z are independently selected from the group consisting of CH, N, S or O.

Most preferably, the compounds are selected from the group consisting of compounds of Formula 1 wherein:

$R^1$ is independently selected from the group consisting of alkyl, 3-pyridyl and 3,4-dimethoxyphenyl; preferably 3-pyridyl or 3,4-dimethoxyphenyl;

$R^2$ is independently selected from the group consisting of H and $CH_3$;

$R^3$ is independently selected from the group of H, OH, and OCHO;

$R^4$ and $R^5$ are independently H;

$R^9$ is independently selected from the group of H and isopropenyl; and

T and Z are independently CH.

Throughout the specification hereof, chemical structures are depicted and numerically labelled. The names of the numbered structures are set forth in Table 1 and indicated in boldface in the text.

TABLE 1

| | Names of Structures |
|---|---|
| 1A | 3-methyl-1H-5a,6,7,8,9-pentahydro-1-oxopyrano[4,3-b][1]benzopyran |
| 1B | cis-3-5a-dimethyl-6-hydroxy-1H-5a,6,7,8,9-pentahydro-1-oxopyrano[4,3-b][1]benzopyran |
| 1C | trans-3-5a-dimethyl-6-hydroxy-1H-5a,6,7,8,9-pentahydro-1-oxopyrano[4,3-b][1]benzopyran |
| 1D | cis-3-5a-dimethyl-6-formyloxy-1H-5a,6,7,8,9-pentahydro-1-oxopyrano[4,3-b][1]benzopyran |
| 1E | trans-3-5a-dimethyl-6-formyloxy-1H-5a,6,7,8,9-pentahydro-1-oxopyrano[4,3-b][1]benzopyran |
| 2A | 3-(3-pyridyl)-1H-5a,6,7,8,9-pentahydro-1-oxopyrano[4,3-b][1]benzopyran |
| 2B | cis-3-(3-pyridyl)-5a-methyl-6-hydroxy-1H-5a,6,7,8,9-pentahydro-1-oxopyrano[4,3-b][1]benzopyran |
| 2C | trans-3-(3-pyridyl)-5a-methyl-6-hydroxy-1H-5a,6,7,8,9-pentahydro-1-oxopyrano[4,3-b][1]benzopyran |
| 2D | cis-3-(3-pyridyl)-5a-methyl-6-formyloxy-1H-5a,6,7,8,9-pentahydro-1-oxopyrano[4,3-b][1]benzopyran |
| 2E | trans-3-(3-pyridyl)-5a-methyl-6-formyloxy-1H-5a,6,7,8,9-pentahydro-1-oxopyrano[4,3-b][1]benzopyran |
| 3A | 3-(3,4-dimethoxyphenyl)-1H-5a,6,7,8,9-pentahydro-1-oxopyrano[4,3-b][1]benzopyran |
| 3B | cis-3-(3,4-dimethoxyphenyl)-5a-methyl-6-hydroxy-1H-5a,6,7,8,9-pentahydro-1-oxopyrano[4,3-b][1]benzopyran |
| 3C | trans-3-(3,4-dimethoxyphenyl)-5a-methyl-6-hydroxy-1H-5a,6,7,8,9-pentahydro-1-oxopyrano[4,3-b][1]benzopyran |
| 3D | cis-3-(3,4-Dimethoxyphenyl)-6-formyloxy-5a-methyl-1H-5a,6,7,8,9-pentahydro-1-oxopyrano[4,3-b][1]benzopyran |
| 3E | trans-3-(3,4-Dimethoxyphenyl)-6-formyloxy-5a-methyl-1H-5a,6,7,8,9-pentahydro-1-oxopyrano[4,3-b][1]benzopyran |
| 4A | cyclohexenecarboxaldehyde |
| 4B | 3-hydroxy-2-methyl-1-cyclohexen-1-carboxaldehyde |
| 4C | 3-formyloxy-2-methyl-1-cyclohexen-1-carboxaldehyde |
| 5A | 4-hydroxy-6-methyl-2-pyrone |
| 5B | 4-hydroxy-6-(3-pyridyl)-2-pyrone |
| 5C | 4-hydroxy-6-(3,4-dimethoxyphenyl)-2-pyrone |
| 6 | 3-5a-dimethyl-6-oxo-1H-5a,6,7,8,9-pentahydro-1-oxopyrano[4,3-b][1]benzopyran |
| 7 | 2-methylcyclohexan-1-one |
| 8 | 2-methyl-2-cyclohexen-1-one |
| 9 | 1,3-dithiane |
| 10 | 1-[2-(1,3-dithianyl)]-2-methyl-2-cyclohexen-1-ol |
| 11 | 3-[2-(1,3-dithianyl)]-2-methyl-2-cyclohexen-1-ol |
| 12A | ethyl nicotinate |
| 12B | ethyl 3,4-dimethoxybenzoate |
| 13A | ethyl 5-(3-pyridyl)-3,5-dioxopentanoate |
| 13B | methyl 5-(3,4-dimethoxyphenyl)-3,5-dioxopentanoate |
| 14A | 3-methyl-1H-5a,6,7,8,9-pentahydro-1-oxopyrano[4,3-b]quinoline |
| 14B | cis-3-5a-dimethyl-6-formyloxy-1H-5a,6,7,8,9-pentahydro-1-oxopyrano[4,3-b]quinoline |
| 14C | cis-3-5a-dimethyl-6-formyloxy-1H-5a,6,7,8,9-pentahydro-1-oxopyrano[4,3-b]benzothiin |
| 18 | 4-bromo-6-methyl-2-pyrone |
| 19 | 4-azido-6-methyl-2-pyrone |

TABLE 1-continued

| | Names of Structures |
|---|---|
| 20 | 4-amino-6-methyl-2-pyrone |
| 21 | 4-mercapto-6-methyl-2-pyrone |
| 22 | tri(deacetyl)pyripyropene A |
| 23 | 20(S)-camptothecin (CPT) |
| 24 | 1H-6,7,8,9-tetrahydro-1-oxopyrano[4,3-b]quinoline |
| 26 | 1H-7,8,9,10-tetrahydro-1-oxopyrano[4,3-c]isoquinoline |
| 27 | (S)-(-)-perillaldehyde |
| 28 | (5aS, 7S)-7-Isopropenyl-3-methyl-1H-5a,6,7,8,9-pentahydro-1-oxopyrano [4,3-b][1] benzopyran |
| 29 | (5aS, 7S)-7-Isopropenyl-3-(3-pyridyl)-1H-5a,6,7,8,9-pentahydro-1-oxopyrano[4,3-b][1]benzopyran |
| 30 | (5aS, 7S)-7-Isopropenyl-3-(3,4-dimethoxyphenyl)-1H-5a,6,7,8,9-pentahydro-1-oxopyrano [4,3-b][1] benzopyran |
| 31 | 3-(Methoxycarbonylmethyl)-1H-5a,6,7,8,9-pentahydro-1-oxopyrano[4,3-b][1]benzopyran |
| 32 | 3-(Carboxymethyl)-1H-5a,6,7,8,9-pentahydro-1-oxopyrano [4,3-b][1] benzopyran |
| 33 | 1,8-Di-{3-[1H-5a,6,7,8,9-pentahydro-1-oxopyrano [4,3-b][1] benzopyranyl]}-2,7-octanedione |
| 34 | (5aS, 7S)-7-[2-(1-hydroxypropyl)]-3-methyl-1H-5a,6,7,8,9-pentahydro-1-oxopyrano [4,3-b][1] benzopyran |
| 35 | (5aS, 7S)-7-[1-(Formyl)ethyl]-3-methyl-1H-5a,6,7,8,9-pentahydro-1-oxopyrano[4,3-b][1] benzopyran |
| 36 | (5aS, 7S)-7-[2-(1-Hydroxypropyl)]-10-hydroxy-3-(3,4-dimethoxyphenyl)-1H-5a,6,7,8,9,9a,10-heptahydro-1-oxopyrano [4,3-b][1] benzopyran |
| 37 | (5aS, 7S)-7-[2-(1-Pentanoyloxypropyl)]-10-hydroxy-3-(3,4-dimethoxyphenyl)-1H-5a,6,7,8,9,9a,10-heptahydro-1-oxopyrano [4,3-b][1] benzopyran |
| 38A | (5aS*, 9aS*, 10S*)-9a,10-Epoxy-3-(3-pyridyl)-1H-5a,6,7,8,9,9a,10-heptahydro-1-oxopyrano [4,3-b][1] benzopyran |
| 38B | (5aS*, 9aR*, 10R*)-9a,10-Dihydroxy-3-(3-pyridyl)-1H-5a,6,7,8,9,9a,10-heptahydro-1-oxopyrano [4,3-b][1] benzopyran |
| 39 | (R)-(-)-carvone |
| 40 | cis-1-iodo-3-(methanesulfonyloxy)-1-propene |
| 41 | (5R,6S)-2,6-Dimethyl-6-(cis-3-iodo-2-propenyl)-5-isopropenyl-2-cyclohexen-1-one |
| 42 | (4aS,5R,8aS)-Methyl-(1H)-1-Oxo-4,4a,5,8,8a-pentahydro-2,5,8a-trimethylnaphthalene-5-acetate |
| 43 | (4aS,5R,8aS)-(1H)-1-Oxo-4,4a,5,8,8a-pentahydro-2,5,8a-trimethylnaphthalene-5-acetic acid |
| 44 | (1S,4aS,8aS)-(1H)-1-[2-(1,3-dithianyl)]-1-hydroxy-4,4a,5,8,8a-pentahydro-2,5,8a-trimethylnaphthalene-5-acetic acid |
| 45 | (4aS,5R,8aS)-(1H)-1-carboxaldehyde-3-formyloxy-4,4a,5,8,8a-pentahydro-2,5,8a-trimethylnaphthalene-5-acetic acid |
| 46 | (4R,4aS,6aS,12bS)-1H,11H-4,4a,5,6,6a,12b-Hexahydro-6-formyloxy-11-oxo-9-(3-pyridyl)-4,6a,12b-trimethylnaphtho[2,1-b]pyrano[3,4-e]pyran-4-acetic acid |
| 47 | (4aS,5S,8aS)-Methyl-(1H)-1-Oxo-4,4a,5,8,8a-pentahydro-2,5,8a-trimethylnaphthalene-5-acetate |

Preferred compounds of this invention are shown in below in Scheme 1 and include compounds selected from the group consisting of: 3-(3-pyridyl)-1H-5a,6,7,8,9-pentahydro-1-oxopyrano[4,3-b]benzopyran [2A]; 3-(3,4-dimethoxyphenyl)-1H-5a, 6,7,8,9-pentahydro-1-oxopyrano[4,3-b]benzopyran [3A]; cis- and trans-3-(3,4-dimethoxyphenyl)-5a-methyl-6-formyloxy-1H-5a,6,7,8,9-pentahydro-1-oxopyrano[4,3-b]benzopyran [3D and 3E]; cis- and trans-3-(3-pyridyl)-5a-methyl-6-formyloxy-1H-5a,6,7,8,9-pentahydro-1-oxopyrano[4,3b]benzopyran [2D and 2E]; cis- and trans-3-(3,4-dimethoxyphenyl)-5a-methyl-6-hydroxy-1 H-5a,6,7,8,9-pentahydro-1-oxopyrano[4,3-b]benzopyran [3B and 3C]; 3-methyl-1H-5a,6,7,8,9-pentahydro-1-oxopyrano[4,3-b]benzopyran [1A]; cis- and trans-3-5a-dimethyl-6-formyloxy-1H-5a,6,7,8,9-pentahydro-1-oxopyrano[4,3-b]benzopyran [1D and 1E]; and cis- and trans-3-(3-pyridyl)-5a-methyl-6-hydroxy-1H-5a, 6,7,8,9-pentahydro-1-oxopyrano[4,3-b]benzopyran [2B and 2C].

A more preferred class of compounds of this invention includes compounds selected from the group consisting of 3-(3-pyridyl)-1H-5a,6,7,8,9-pentahydro-1-oxopyrano[4,3-b]benzopyran [2A]; 3-(3,4-dimethoxyphenyl)-1H-5a,6,7,8,9-pentahydro-1-oxopyrano[4,3-b]benzopyran [3A]; cis- and trans-3-(3,4-dimethoxyphenyl)-5a-methyl-6-formyloxy-1H-5a,6,7,8,9-pentahydro-1-oxopyrano[4,3-b]benzopyran [3D and 3E]; cis- and trans-3-(3-pyridyl)-5a-methyl-6-formyloxy-1H-5a,6,7,8,9-pentahydro-1-oxopyrano[4,3-b]benzopyran [2D and 2E]; cis- and trans-3-(3,4-dimethoxyphenyl)-5a-methyl-6-hydroxy-1H-5a,6,7,8,9-pentahydro-1-oxopyrano[4,3-b]benzopyran [3B and 3C]; and cis- and trans-3-(3,4-dimethoxyphenyl)-5a-methyl-6-hydroxy-1H-5a, 6,7,8,9-pentahydro-1-oxopyrano[4,3-b]benzopyran [3B and 3C]; 1H-6,7,8,9-tetrahydro-1-oxopyrano[4,3-b]quinoline [24]; 1H-7,8,9,10-tetrahydro-1-oxopyrano[4,3-c]isoquinoline [26]; (5aS*, 9aR*, 10R*)-9a, 10-Dihydroxy-3-(3-pyridyl)-1H-5a,6,7,8,9,9a,10-heptahydro-1-oxopyrano[4,3-b][1]benzopyran [38B]; (5aS, 7S)-7-[2-(1-Pentanoyloxypropyl)]-10-hydroxy-3-(3,4-dimethoxyphenyl)-1H-5a,6,7,8,9,9a,10-heptahydro-1-oxopyrano [4,3-b][1]benzopyran [37]; (5aS, 7S)-7-Isopropenyl-3-(3,4-dimethoxyphenyl)-1H-5a,6,7,8,9-pentahydro-1-oxopyrano[4,3-b][1]benzopyran[30]; (5aS, 7S)-7-Isopropenyl-3-(3-pyridyl)-1 H-5a,6,7,8,9-pentahydro-1-oxopyrano[4,3-b][1]benzopyran [29]; (5aS, 7S)-7-Isopropenyl-3-methyl-1H-5a,6,7,8,9-pentahydro-1-oxopyrano[4,3-b][1]benzopyran [28]; and 3-(Carboxymethyl)-1H-5a,6,7,8,9-pentahydro-1-oxopyrano [4,3-b][1] benzopyran [32].

A most preferred class of compounds of this invention includes compounds selected from the group consisting of 3-(3-pyridyl)-1H-5a,6,7,8,9-pentahydro-1-oxopyrano[4,3-b]benzopyran [2A]; 3-(3,4-dimethoxyphenyl)-1H-5a,6,7,8, 9-pentahydro-1-oxopyrano[4,3 -b]benzopyran [3A]; cis- and trans-3-(3,4-dimethoxyphenyl)-5a-methyl-6-formyloxy-1H-5a,6,7,8,9-pentahydro-1-oxopyrano[4,3-b]benzopyran [3D and 3E]; and cis- and trans-3-(3,4-dimethoxyphenyl)-5a-methyl-6-hydroxy-1H-5a,6,7,8,9-pentahydro-1-oxopyrano[4,3-b]benzopyran [3B and 3C]; and 1,8-Di-{3-[1H-5a,6,7,8,9-pentahydro-1-oxopyrano [4,3-b][1]benzopyranyl]}-2,7-octanedione [33].

This invention also provides methods as illustrated in Schemes 1, 2, 6, 7, 8 and 9 below for making the above compounds via condensation reactions between an aldehyde of a cyclohexene having $R^2$ and $R^3$ substituents as defined above, and an ortho-oxy-substituted heterocyclic ring having as a para-substituent a reactive group capable of reacting with the β carbon of the enal function (carbon containing $R^2$) to form the tricyclic product. These anticancer drugs are easy to prepare in large quantities using few steps.

The method comprises contacting:

(a) a compound of the formula:

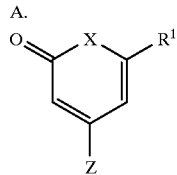

A.

wherein X is as defined for Formula I;
wherein $R^1$ is defined as $R^3$ as set forth in Formula I above; and
Z is a reactive group comprising Y (as defined in Formula I above, i.e. O, S or N);
with
(b) a compound having an aldehyde substituent of the formula:

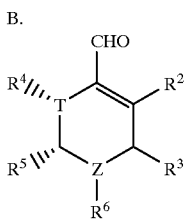

B.

wherein:
$R^2$ and $R^3$ are as defined above for Formula I, $R^6$ is defined as $R^3$ for Formula I above, and
$R^4$ and $R^5$ are as defined above for Formula I; and T and Z are independently CH, N, S or O under reaction conditions whereby a condensation reaction takes place between said compounds of paragraphs (a) and (b) whereby reactive groups $R^3$ and Z react with said substituted ene aldehyde to form a compound as defined in the Formula I above.

Compounds of Formula I and Formula 1 where X≠Y may be made by means known to the art by methods analogous to those disclosed herein. Further, compounds of Formula I and Formula 1 where T÷#CH, Z÷CH, $R^4$÷H, or $R^5$÷H may be made by means known to the art by methods analogous to those disclosed herein.

More preferably, the method comprises making a compound of Formula 1 comprising contacting:

(a) a compound of the formula:

4.

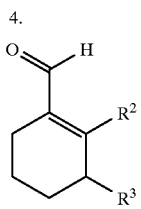

wherein $R^2$ and $R^3$ are as defined for Formula 1 above, with
(b) a compound of the formula:

5.

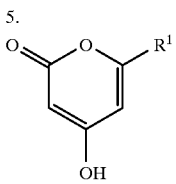

wherein:
$R^1$ is defined as $R^3$ as set forth for Formula 1 above.

Methods are also provided for making compounds of Formula IV above comprising reacting (a) compounds of the formula:

C.

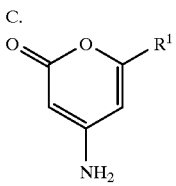

wherein $R^1$ is defined as $R^3$ as set forth above for Formula I;

with
(b) compounds of the formula:

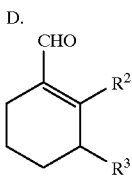
D.

wherein $R^2$ and $R^3$ are as defined above for Formula I.

Methods are provided for making compounds of Formula VI above comprising reacting (a) compounds of the formula:

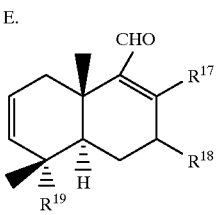
E.

wherein:
$R^{17}$ and $R^{18}$ are independently defined as $R^3$ as set forth for Formula I above;
$R^9$ is $CH_2R$, wherein R is as defined as $R^3$ as set forth for Formula I above; with
(b) compounds of the formula:

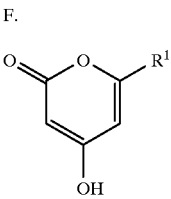
F.

wherein $R^1$ is defined as $R^3$ as set forth for Formula I above.

Methods are also provided for making a compound of Formula E above comprising reacting:
(a) a compound of the formula:

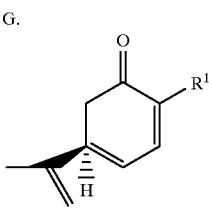
G.

wherein $R^1$ is defined as $R^3$ as set forth for Formula I above; with
(b) a compound of the formula:

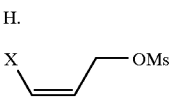
H.

wherein X is I, Br, or Cl, and Ms is methanesulfonyl.

A method is also provided for inhibiting an enzyme selected from the group consisting of acetylcholinesterase and cholesterol acyltransferase in a patient comprising administering to the patient an effective amount of a compound of this invention. An effective amount is an amount capable of effecting measurable inhibition, preferably an amount capable of effecting inhibition equivalent or greater than that of known AChE inhibitor Tacrine or known ACAT inhibitor CP-113,818 (see Examples hereof). As is known to the art, dosage can be adjusted depending on the bioactivity of the particular compound chosen. The compound may be administered in combination with a suitable pharmaceutical carrier such as DMSO, ethyl alcohol, or other carriers known to the art.

Patients include humans, large mammals, livestock animals, pets, and laboratory animals.

A method is also provided for inhibiting macromolecule (e.g., DNA, RNA and protein) synthesis and growth of cancer cells in a patient comprising administering to the patient an effective amount of a compound of this invention. Suitable pharmaceutical carriers may be used for administration of the compound. An effective amount to inhibit macromolecule synthesis or cell growth is an amount sufficient to inhibit macromolecule production or cell growth at least as well as 20(S)-camptothecin (CPT) as measured in standard assays as described in the Examples hereof.

A method is also provided for inhibiting tubulin polymerization in a patient comprising administering to the patient an effective amount of a compound of this invention. Suitable pharmaceutical carriers may be used for administration of the compound. An effective amount is an amount capable of effecting measurable inhibition, preferably an amount capable of effecting inhibition equivalent to known tubulin polymerization inhibitor colchicine.

Methods are also provided herein for prevention of tubulin polymerization, tumor development, inhibiting the rate of tumor growth, and inducing regression of pre-existing tumors comprising administering to a patient an effective amount of a compound of this invention. An effective dosage for each purpose may be readily calculated by those of skill in the art based on effective dosages for inhibition of macromolecule synthesis, optimized and adjusted as required for individual patients.

Interestingly, Tau, which is a major component of the abnormal intracellular tangles of filaments found in the brain of Alzheimer patients, is a non-energy transducing microtubule-associated protein. If tricyclic pyrones bind to tubulin and disrupt microtubule dynamics, they should also decrease or prevent the interactions of Tau and other microtubule-associated proteins with microtubules that are involved in Alzheimer's disease.

The mechanism of action by which the compounds inhibit cancer cells is unknown; however, a possible mechanism is that the compounds bind selectively and strongly with one of the oxidative enzymes which undergoes oxidation at the $C_3$–$C_4$ double bond to form the corresponding $C_3$–$C_4$ epoxide and this epoxide then subsequently undergoes a ring opening reaction with a nucleophile of DNA, RNA, or enzymes in the cancer cell.

DETAILED DESCRIPTION OF THE PREFERRED EMBODIMENTS

Figure 1:
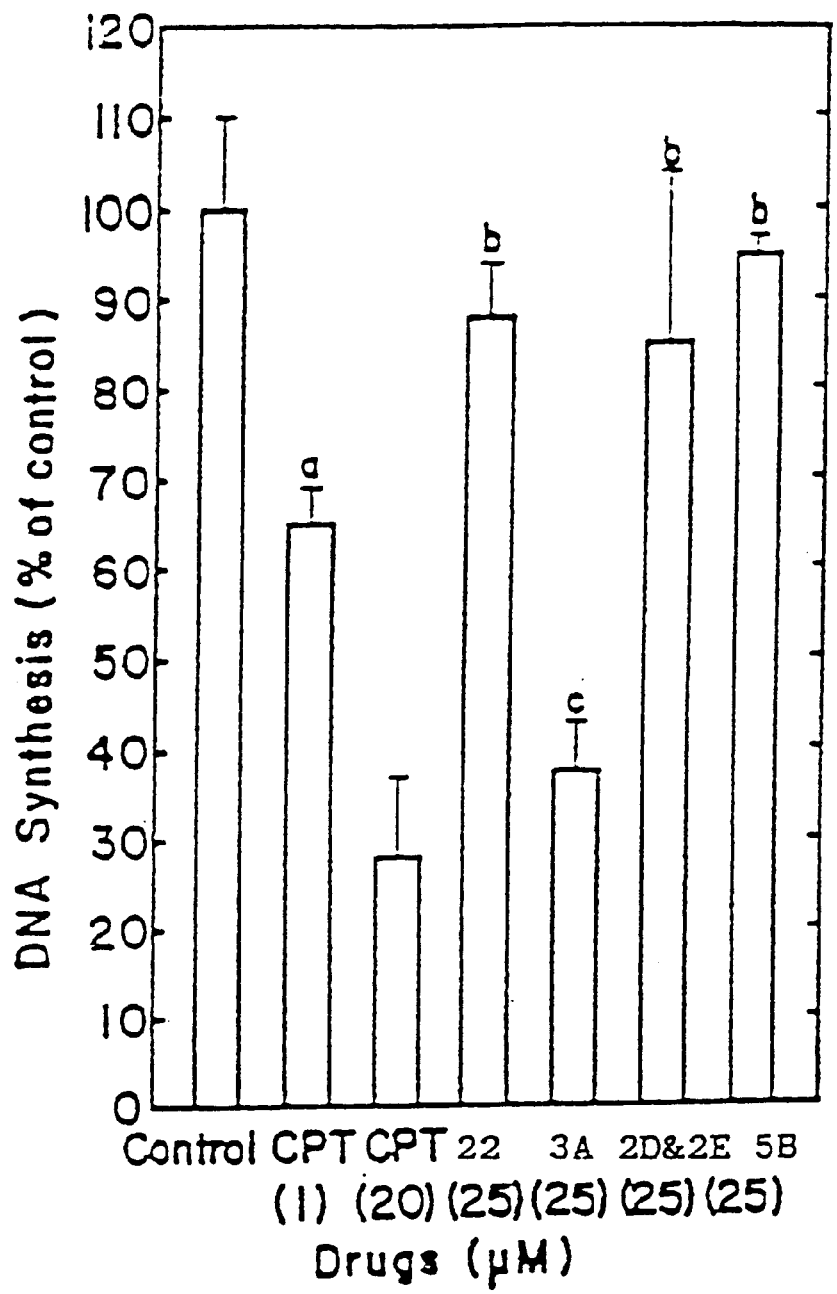
FIG. 1 illustrates a comparison of the effects of four new tricyclic pyrone derivatives and CPT on DNA synthesis in L1210 cells in vitro. About $2.53 \times 10^6$ cells suspended in 0.5 ml of RPMI 1640 medium were incubated at 37° C. for 90 minutes in the presence or absence (control) of the indicated concentrations of drugs. The cells were then pulse-labeled for an additional 30 minutes to determine the rate of $^3$H-thymidine incorporation into DNA. DNA synthesis in vehicle-treated control cells was 43,956±4,569 cpm (100±11%). The blank value (1,241±99 cpm) for cells pulse-labeled for 0 minutes with 1 μCi of $^3$H-thymidine has been subtracted from the results. Bars: means±SD (n=3). $^a$P<0.1, significantly smaller than control; $^b$not significantly different from control; $^c$not different from CPT (20 μM).

Tricyclic pyrones of this invention were tested for their ability to prevent L1210 leukemic cells from synthesizing macromolecules and growing in vitro. The term macromolecules, as used herein, refers to DNA, RNA and proteins. The compounds tested are listed with structures) in Table 2.

TABLE 2

Compounds Tested for Antitumor Activity

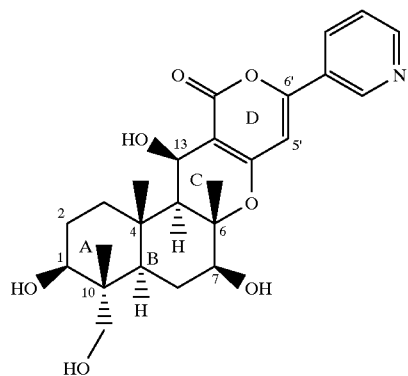

22

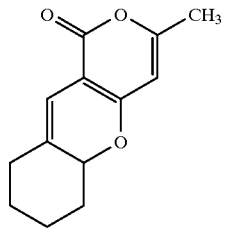

1A

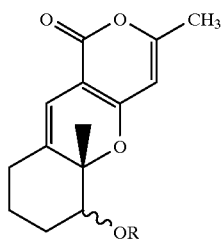

1D & 1E: R = CHO

TABLE 2-continued

Compounds Tested for Antitumor Activity

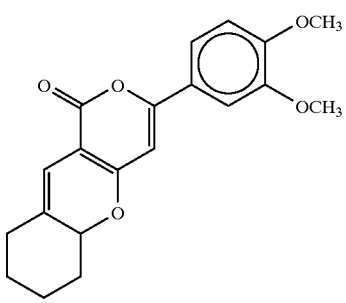

3A

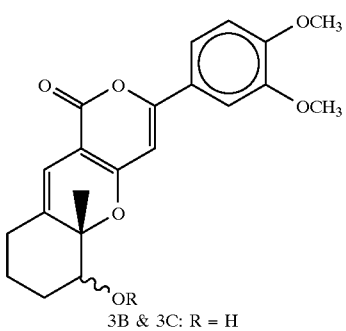

3B & 3C: R = H
3D & 3E: R = CHO

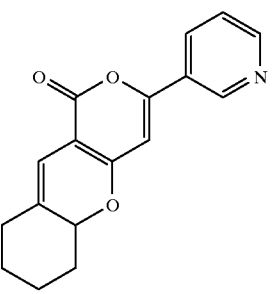

2A

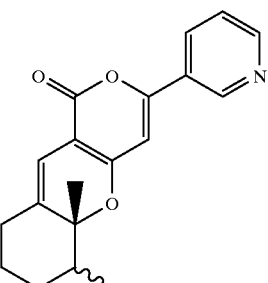

2B & 2C: R = H
2D & 2E: R = CHO

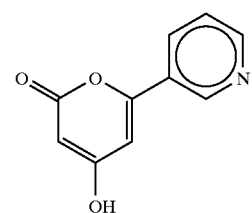

TABLE 2-continued

Compounds Tested for Antitumor Activity

5B

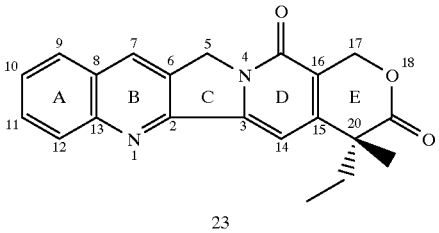

23

Compound 23, 20(S)-camptothecin (CPT), a known anti-cancer drug, which inhibits topoisomerase I activity and exhibits a broad spectrum of antitumor activity, was also tested for purposes of comparison, as was compound 22, tri(deacetyl)pyripyropene A (Tomoda, H., et al. (1994), "Relative and Absolute Stereochemistry of Pyripyropene A, A Potent, Bioavailable Inhibitor of Acyl-CoA:Cholesterol Acyltransferase (ACAT),"J. Am. Chem. Soc. 116:12097–12098), Obata, R. et al. (1996), "Chemical modification and structure-activity relationships of pyripyropenes. 1. Modification at the four hydroxyl group,"J. Antibiotics 49:1133–1148, a tetracyclic pyrone, and compound 5B (4-hydroxy-6-(3-pyridyl)-2-pyrone), a monocyclic pyrone. The most preferred compounds of this invention were more effective than compounds 22 and 5B in inhibiting DNA synthesis and tumor cell growth, and were somewhat less effective than CPT at the concentrations tested.

This invention also provides a new chemical reaction as shown in Scheme 1 involving the condensation of pyrones with cyclohexenecarboxaldehydes to synthesize the cancer-active tricyclic pyranes of this invention. For example, equivalent molar amounts of the aldehyde and pyrone in solution, e.g., in ethyl acetate and 0.5 equivalents of L-proline, are stirred together under argon for three days, increasing the temperature from about 25° C. the first day to about 60° C. the last day, followed by dilution, washing, drying and concentrating.

More specifically, a simple synthesis of tricyclic pyrones with the general structure as depicted in Formula 1 (Scheme 1) is provided using a coupling reaction of 1-cyclohexenecarboxaldehydes (4) and 6-substituted 4-hydroxy-2-pyrones (5). For example, treatment of 1-cyclohexenecarboxaldehyde (4A) with one equivalent of 4-hydroxy-6-methyl-2-pyrone (5A) and 0.5 equivalent of L-proline in ethyl acetate at 70° C under argon for 12 hours provided an 80% yield (based on reacted pyrone 5A) of 1A (Scheme 2). The structure of 1A was determined by $^{1}H$ and 13C NMR, mass spectrometry, IR, elemental analysis, and single-crystal X-ray analysis.

Scheme 1

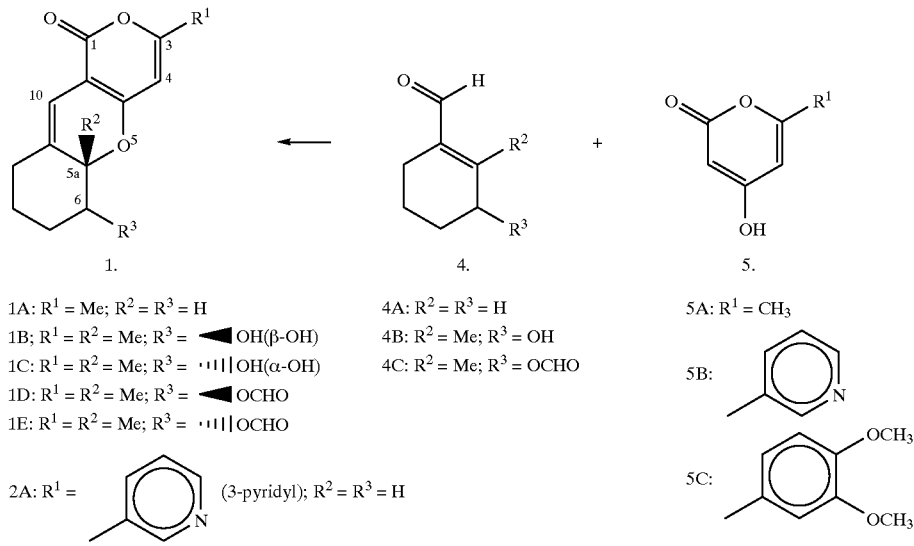

1A: $R^1$ = Me; $R^2 = R^3$ = H
1B: $R^1 = R^2$ = Me; $R^3$ = ◀ OH(β-OH)
1C: $R^1 = R^2$ = Me; $R^3$ = ⦀OH(α-OH)
1D: $R^1 = R^2$ = Me; $R^3$ = ◀ OCHO
1E: $R^1 = R^2$ = Me; $R^3$ = ⦀OCHO

2A: $R^1$ = (3-pyridyl); $R^2 = R^3$ = H

4A: $R^2 = R^3$ = H
4B: $R^2$ = Me; $R^3$ = OH
4C: $R^2$ = Me; $R^3$ = OCHO

5A: $R^1$ = $CH_3$

5B:

5C:

-continued

2B: $R^1$ = (3-pyridyl); $R^2$ = Me; $R^3$ = ◂OH
2C: $R^1$ = (3-pyridyl); $R^2$ = Me; $R^3$ = ⋯OH
2D: $R^1$ = (3-pyridyl); $R^2$ = Me; $R^3$ = ◂OCHO
2E: $R^1$ = (3-pyridyl); $R^2$ = Me; $R^3$ = ⋯OCHO 3A: $R^1$ = 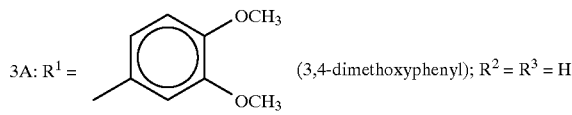 (3,4-dimethoxyphenyl); $R^2$ = $R^3$ = H 3B: $R^1$ = (3,4-dimethoxyphenyl); $R^2$ = Me; $R^3$ = ◂OH
3C: $R^1$ = (3,4-dimethoxyphenyl); $R^2$ = Me; $R^3$ = ⋯OH
3D: $R^1$ = (3,4-dimethoxyphenyl); $R^2$ = Me; $R^3$ = ◂OCHO
3E: $R^1$ = (3,4-dimethoxyphenyl); $R^2$ = Me; $R^3$ = ⋯OCHO Similarly, Pyrone 5A also condensed with carboxaldehydes 4B and 4C separately in the presence of 0.5 equivalent of L-proline or catalytic amount of piperidine and acetic acid in ethyl acetate at 60–80° C. to give a 72% yield of a mixture of 1B and 1C (in a ratio of 1.6:1; determined by 1H NMR spectrum) and a 62% yield of a mixture of 1D and 1E (in a ratio of 3:1), respectively (Scheme 2). Compounds 1B and 1C were not separated; however, oxidation of this mixture with 1,1,1-triacetoxy-1,1-dihydro-1,2-benziodoxol-3(1H)-one[1] in $CH_2Cl_2$ at room temperature gave the corresponding C-6 ketone 6. Reduction of ketone 6 with diisobutylaluminum hydride in THF provided pure cis-alcohol 1B. Pyranobenzopyrans 1D and 1E were separated by column chromatography and the structure of the cis-isomer, 1D, was unequivocally determined by a single-crystal X-ray analysis. Basic hydrolysis of pure 1D with $K_2CO_3$ in MeOH at room temperature gave pure alcohol 1B (Scheme 3).

-continued

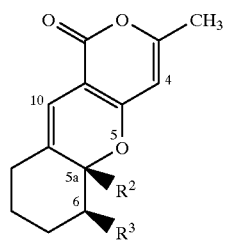

1B & 1C: $R^2$ = $CH_3$; $R^3$ = OH
(72% yield)
1D & 1E: $R^2$ = $CH_3$; $R^3$ = OCHO
(62% yield)

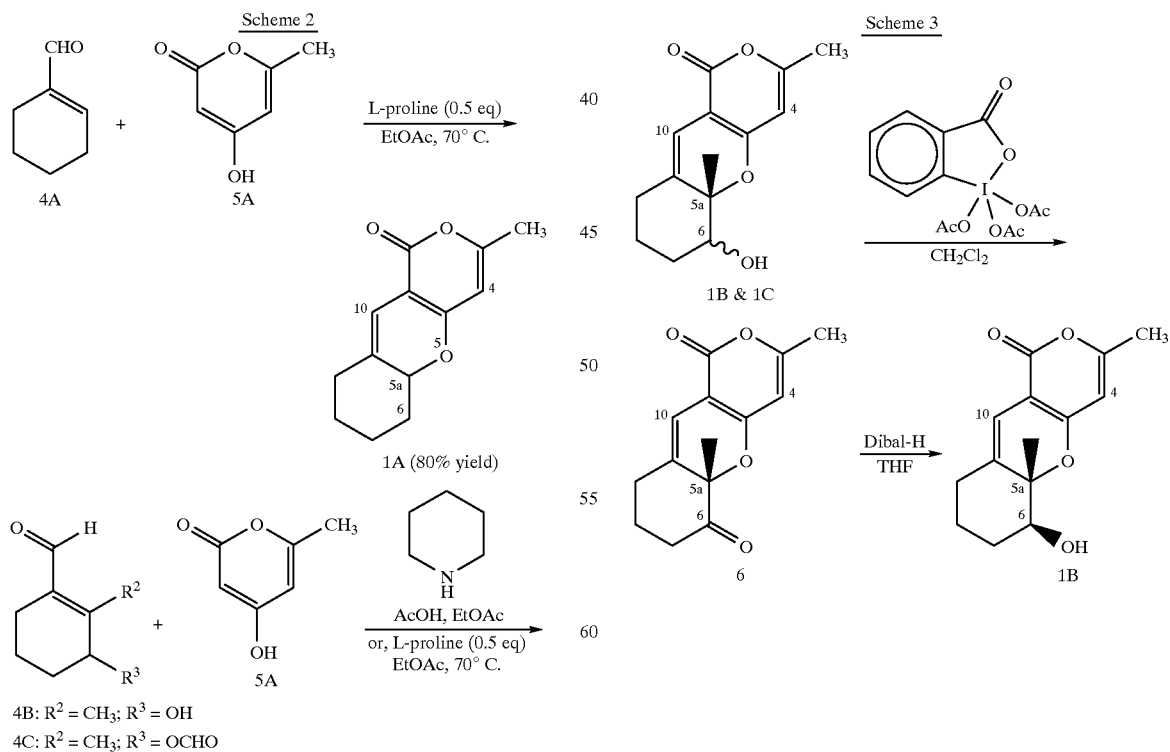

4B: $R^2$ = $CH_3$; $R^3$ = OH
4C: $R^2$ = $CH_3$; $R^3$ = OCHO

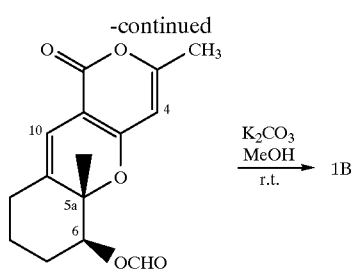

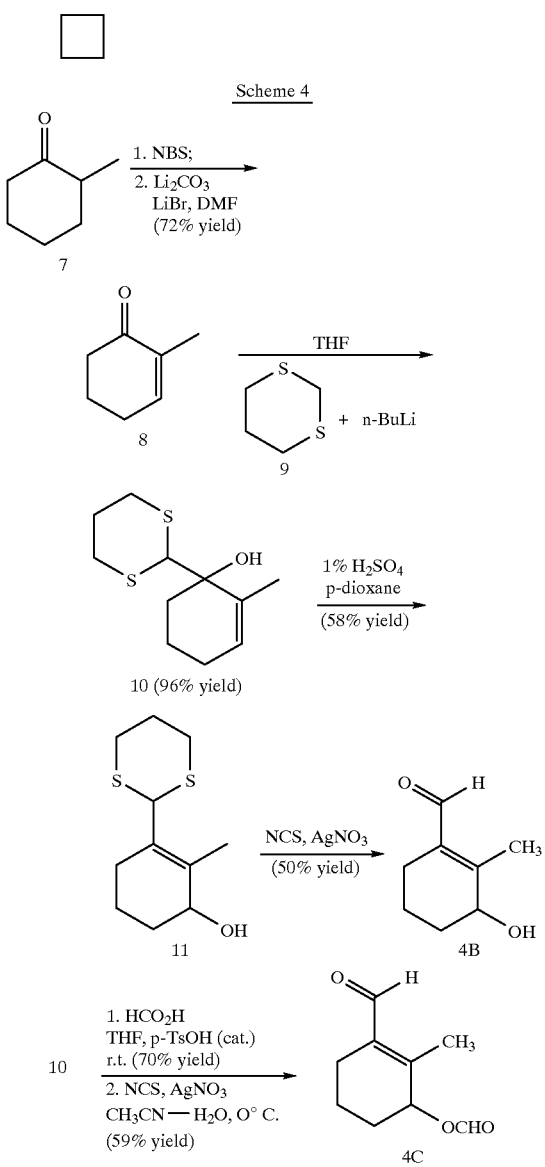

Aldehydes 4B and 4C were synthesized by a modification of the procedure reported by Corey and Erickson (Corey, E. J. and Erickson, B. W. (1971) "Oxidative hydrolysis of 1,3-dithiane derivatives to carbonyl compounds using N-halosuccimide reagent," J. Org. Chem. 36(3):553–560) which is depicted in Scheme 4. Bromination of 2-methylcyclohexanone (7) with 1 equivalent of N-bromosuccinimide (Rinne, W. W. et al., "New methods of preparation of 2-methylcyclohexen-1-one," J. Am. Chem. Soc. (1950) 72:5759–5760) in refluxing $CCl_4$ for 12 hours gave quantitative yield of 2-bromo-2-methylcyclohexanone. Dehydrobromination of this bromide with three equivalents of $Li_2CO_3$ and three equivalents of LiBr in N,N-dimethylformamide (DMF) (Stotter, P. L. and Hill, K. A., "α Halocarbonyl Compounds. E. A Position-Specific Preparation of α-Bromo Ketones by Bromination of Lithium Enolates. A Position-Specific Introduction of α, β-Unsaturation into Unsymmetrical Ketones,"J. Org. Chem. (1973) 38:2576–2578) at 130° C. for 3 h provided a 72% yield of 2-methyl-2-cyclohexen-1-one (8). A 1,2-addition reaction of 8 with 1.5 equivalents of lithiated 1,3-dithiane [generated from 1,3-dithiane (9) with n-BuLi in THF] in THF at −10° C. to give a 96% yield of the 1,2-adduct 10. Rearrangement of 10 with 1 % sulfuric acid in p-dioxane (52% yield) followed by removal of the dithiane protecting group of the resulting alcohol, 11, with N-chlorosuccinimide (NCS) and silver nitrate in acetonitrile-water gave aldehyde 4B (50% yield). Alcohol 4B is not a stable compound and decomposes upon standing at room temperature in a few days. A more stable material, 4C, was synthesized in a better yield from the rearrangement reaction of 10 in formic acid-THF in the presence of catalytic amount of p-toluenesulfonic acid (70% yield) followed by removal of the dithiane moiety with $NCS-AgNO_3$ (59% yield) (Scheme 4). In the formic acid rearrangement reaction, besides the desired product, 1-[2-(1,3-dithianyl)]-3-formyloxy-2-methyl-1-cyclohexene, 9% yield of 3-[2-(1,3-dithianyl)]-2-methyl-2-cyclohexen-1-ol (11) was also isolated.

To demonstrate the generality of the newly-developed condensation reaction (i.e., Scheme 2), other pyrones such as 5B and 5C were also prepared and used in the condensation reaction. Scheme 5 outlines the preparation of 5B and 5C by following a small modification of the reported procedure (only 5B was reported)(Narasimhan, N. S. and Ammanamanchi, R., "Mechanism of acylation of dilithium salts of β-ketoesters: an efficient synthesis of anibine,"J. Org. Chem (1983) 48:3945–3947). Treatment of ethyl acetoacetate in diethyl ether with 2.5 equivalents of lithium diisopropylamide (LDA) at 0° C. for 1 h followed by 1 equivalent of ethyl nicotinate (12A) gave an 87% yield of triketone 13A (Scheme 5). Cyclization of 13A at 150° C. under 3 mm Hg reduced pressure for 0.5 h gave an 89% yield (based on 10.9% of recovered starting triketone) of pyrone 5B. Similarly, pyrone 5C was synthesized from ethyl 3,4-dimethoxybenzoate (12B). However, during the work-up procedure of coupling reaction of ethyl acetoacetate and 12B, the corresponding carboxylic acid of 13B was isolated, which upon methylation with diazomethane in methylene chloride and diethyl ether afforded a 56% yield of methyl ester 13B. Intramolecular cyclization of 13B gave a 70.5% yield (based on 60% recovery of starting triketone 13B) of 5C.

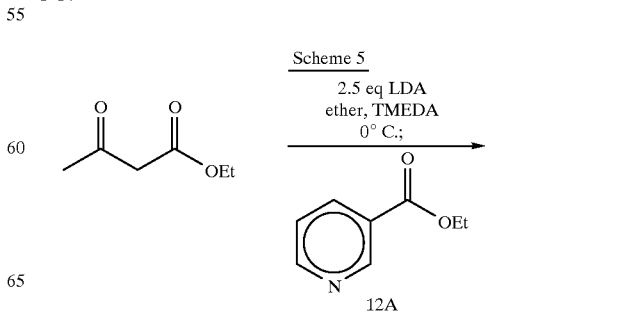

-continued

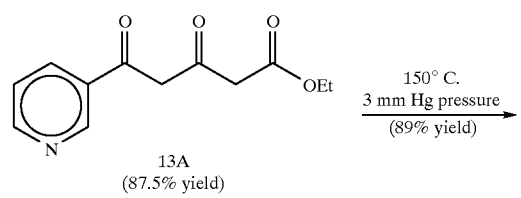
13A
(87.5% yield)

150° C.
3 mm Hg pressure
(89% yield)

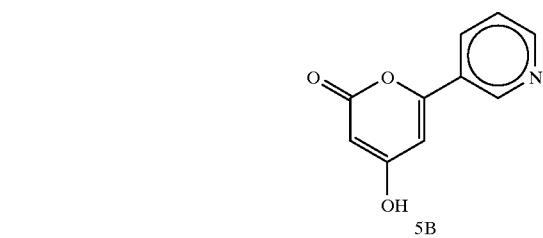
5B

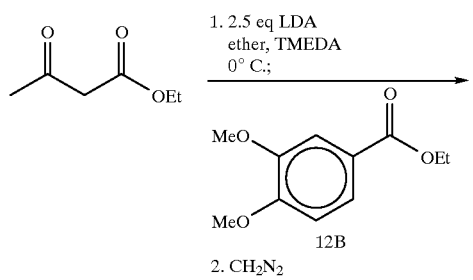
12B 1. 2.5 eq LDA
ether, TMEDA
0° C.;
2. CH₂N₂

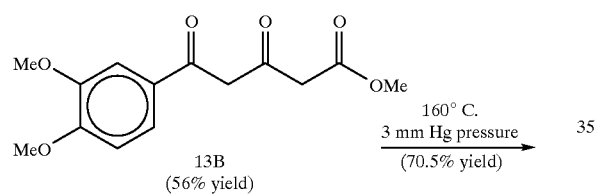
13B
(56% yield)

160° C.
3 mm Hg pressure
(70.5% yield)

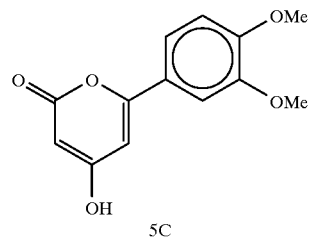
5C

Condensation of aldehyde 4A with pyrones 5B and 5C separately in the presence of 0.5 equivalent of L-proline in ethyl acetate at 70° C. generated pyranobenzopyrans 2A and 3A in 73% and 62% yield, respectively (Scheme 6). In the condensation of formyloxy aldehyde 4C, some of the formyloxy group was hydrolyzed to produce the corresponding alcohol. Hence, treatment of aldehyde 4C with pyrone 5B and 0.5 equivalent of L-proline in ethyl acetate at 70° C. afforded 39% yield of formates 2D and 2E (in a ratio of 2:1) and 11% yield of alcohols 2B and 2C (ratio of 2:1).

Scheme 6

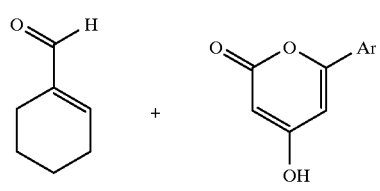

L-proline (0.5 eq)
EtOAc, 70° C.

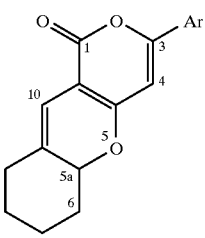

5B: Ar =  2A: Ar =  (73% yield)

5C: Ar =  3A: Ar =  (62% yield)

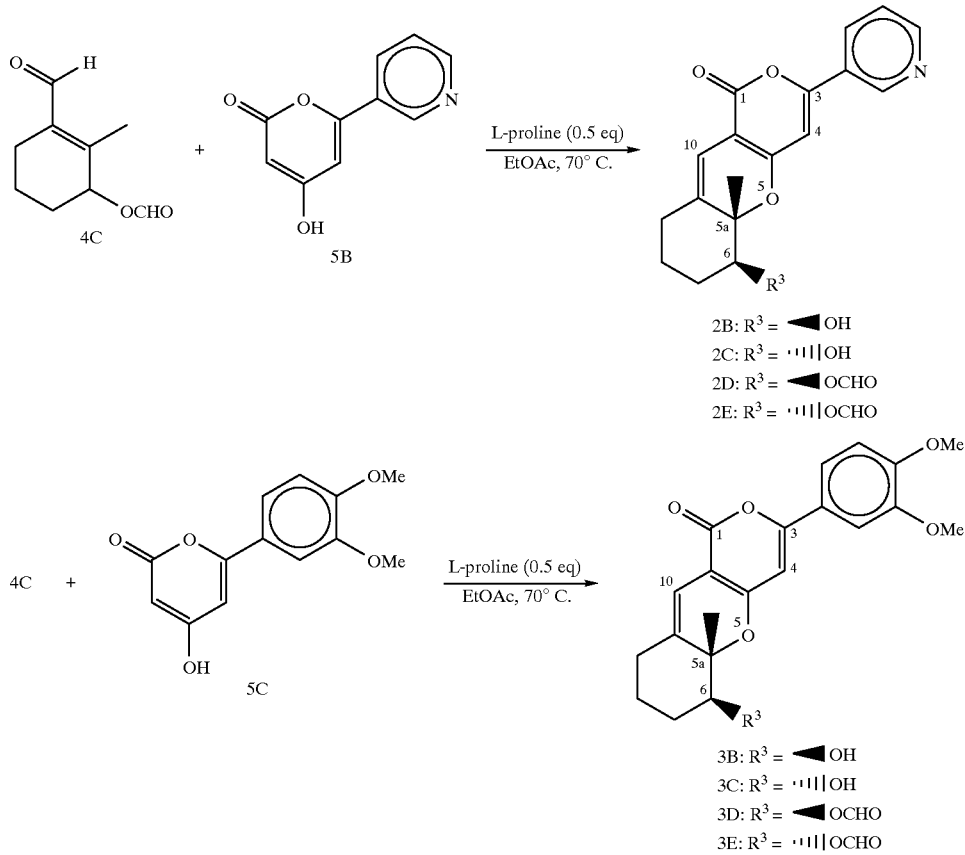

Similarly condensation of 4C and 5C gave a 48% yield of 3D and 3E (2:1) and a 24% yield of 3B and 3C (2:1). In general, these cis and trans isomers (such as 3D and 3E, etc.) are separable by silica gel column chromatography (see Experimental Section). Condensation of alcohol 4B with pyrone 5C also provides a mixture of 2:1 ratio of the cis and trans adducts 3B and 3C.

This condensation reaction apparently is a general reaction and therefore can be applied to nitrogen and sulfur analogs. Hence, general structures, 14 (Scheme 7), can be synthesized from this reaction and subsequent chemical conversion of compounds 1–3 and 14 will provide a large number of derivatives, some of which are outlined in Scheme 7, such as 15 and 16. In Scheme 7, the synthesis of nitrogen analogs, 14A and 14B, and a sulfur analog, 14C, are demonstrated. The precursor pyrone 20 is a known compound (Cervera, M. et al., "R-4-Amino-6-methyl-2H-pyran-2-one, Preparation and Reactions with Aromatic Aldehydes," Tetrahedron (1990) 46:7885–7892). We have already prepared this compound and the reactions are depicted in Scheme 7.

Additionally, a simple synthesis of nitrogen-containing tricyclic pyrones with general structure as depicted in Formulas IV and V is provided using a coupling reaction of 4-amino-pyrones and 1-cyclohexenecarboxaldehydes. Syntheses for the 5-nitrogen analogs 24 and 26 are shown in Scheme 8. It should be noted that nitrogen analog 14A was expected to be found from the reaction of 20 and 4A. However, 14A undergoes dehydrogenation under the reaction conditions to give compound 24. The synthesis of the 5-nitrogen analogs 24 and 26 were accomplished by heating 4-aminopyrone 20 with aldehyde 4A in the presence of a catalytic amount of (S)-(+)-10-camphorsulfonic acid in toluene at 85° C. to give 19% yield (based on unrecovered starting material) and 48% yield of the isomer 26 (Scheme 8b). The NMR spectra alone cannot determine the structures of 24 and 26. Single crystals of 24 and 26 were obtained (separately) and their structures were firmly established by single-crystal X-ray analyses.

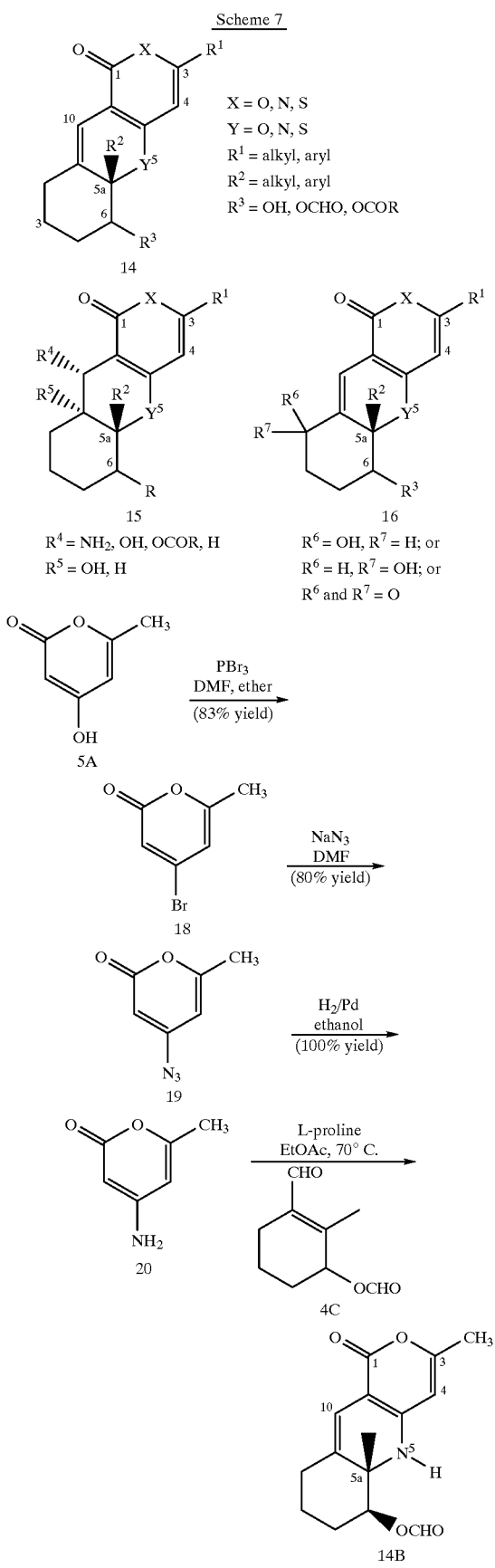

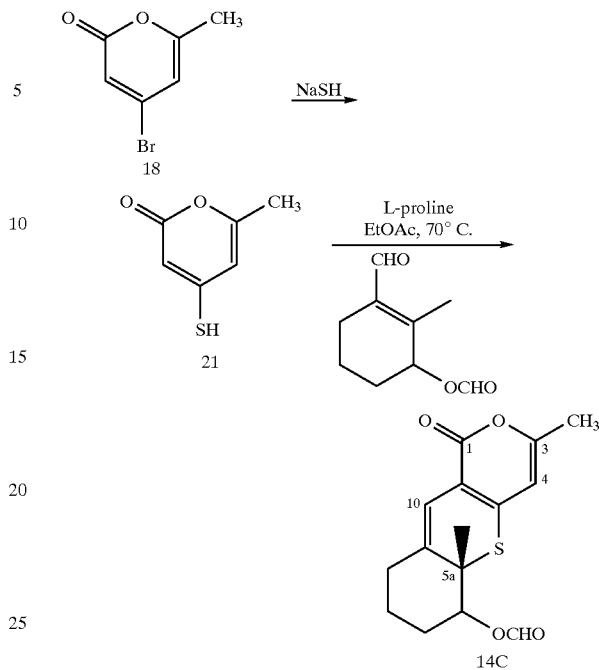

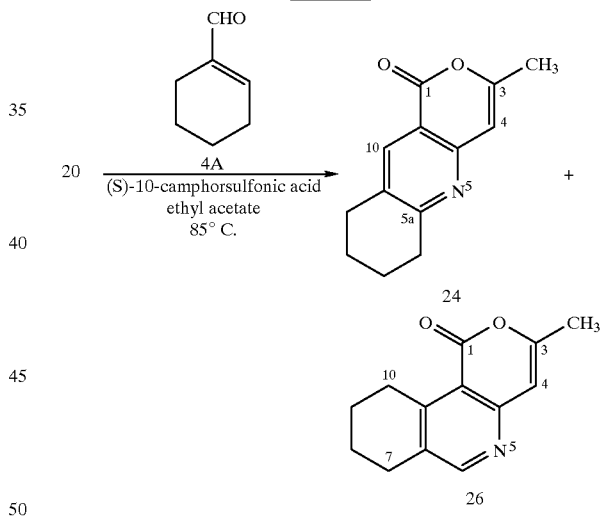

A remarkable asymmetric induction was also observed for the newly-developed condensation reaction from a C-4 stereogenic center in the carboxaldehyde, such as (S)-(-)-perillaldehyde (27). Treatment of (S)-27 with pyrone 5A, 5B, and 5C separately gave single diastereomers 28 (78% yield), 29 (65% yield), and 30 (63% yield), respectively (Scheme 9). The structure of 28 was firmly established by single-crystal X-ray analysis and the data from $^1$H NMR spectra also agrees with the same stereochemical assignment: 5aS and 7S: the C-5a proton (for example, in 28) resonates at δ 5.15 ppm as a doublet of a doublet with J=11.2 Hz and 5.2 Hz (axial-axial and axial-equatorial couplings), indicative of an axial hydrogen (at C-5a).

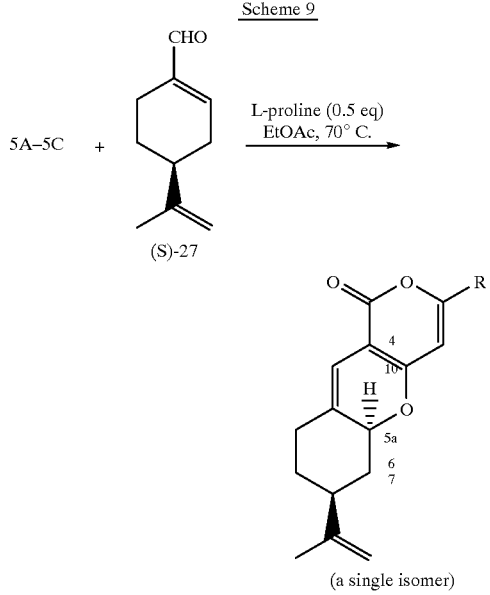

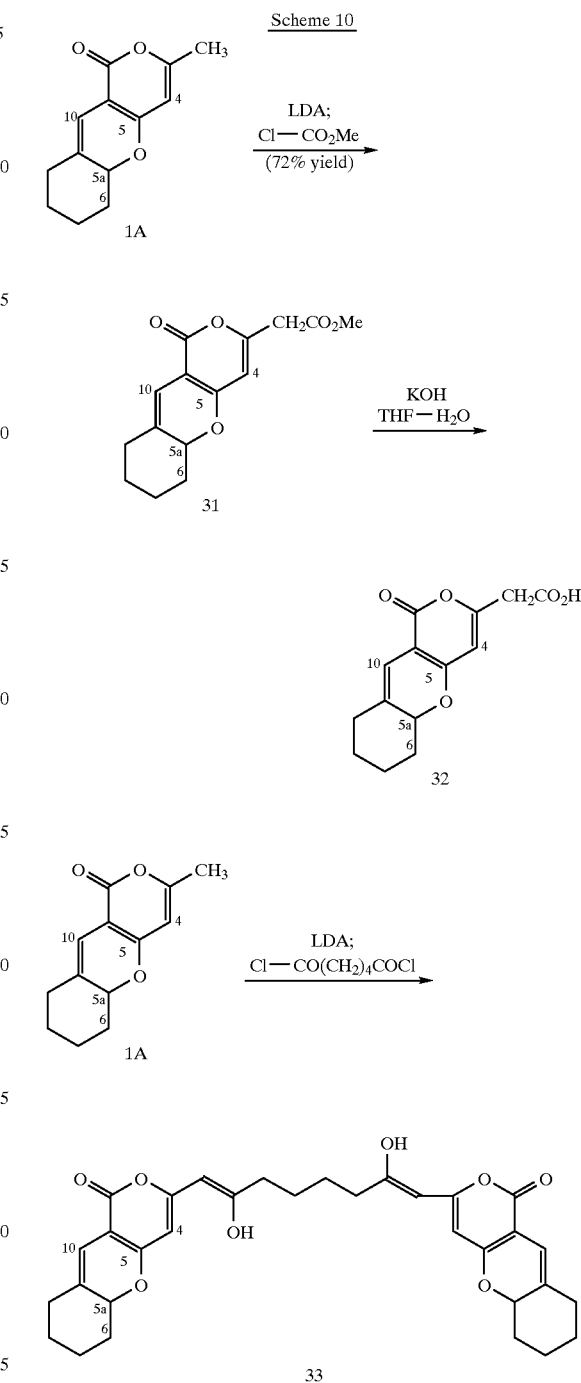

To demonstrate the possibility of preparing various substituted derivatives, several chemical manipulations were also performed on the newly-developed tricyclic pyrones. Scheme 10 summarizes these manipulations. Deprotonation of 1A with lithium diisopropylamide (LDA) in THF at −78° C. followed by methyl chloroformate gave a 72% yield of methyl ester 31. Basic hydrolysis of 31 with KOH in THF and $H_2O$ provided a good yield of the acid 32. The lithiated anion derived from 1A and LDA also reacted with 0.5 equivalent of dielectrophile, adipoyl chloride, to produce diketone 33 (which exists as the enol form). The isopropenyl group of C-7 substituted tricyclic pyrones such as 28 can be hydroxylated with 1 equivalent of borane-THF followed by NaOH-30% $H_2O_2$ to give primary alcohols 34 (69% yield; two inseparable diastereomers at C-12). Oxidation of alcohols 34 with 1,1,1-triacetoxy-1,1-dihydro-1,2-benziodoxol-3(1H)-one in methylene chloride gave an 87% yield of aldehydes 35.

When a greater than 1 equivalent of borane was used, both C-11 and C-9a double bonds can be oxidized to afford a mixture of diols such as 36 (2 diastereomers at C-11). Hence, hydroboration of pyrone 30 with excess of borane in THF followed by NaOH-30% $H_2O_2$ gave diol 36 as a 1:1 mixture of two diastereomers at C-11. Acylation of 36 with pyridine and valeryl chloride in methylene chloride gave good yield of ester 37. C-9a double bond of 2A was epoxidized with 1 equiv of HCl (to protonate the pyridine nitrogen) followed by 1 equiv of m-chloroperbenzoic acid (MCPBA) to give a 1:4.1 ratio of 38A and 38B.

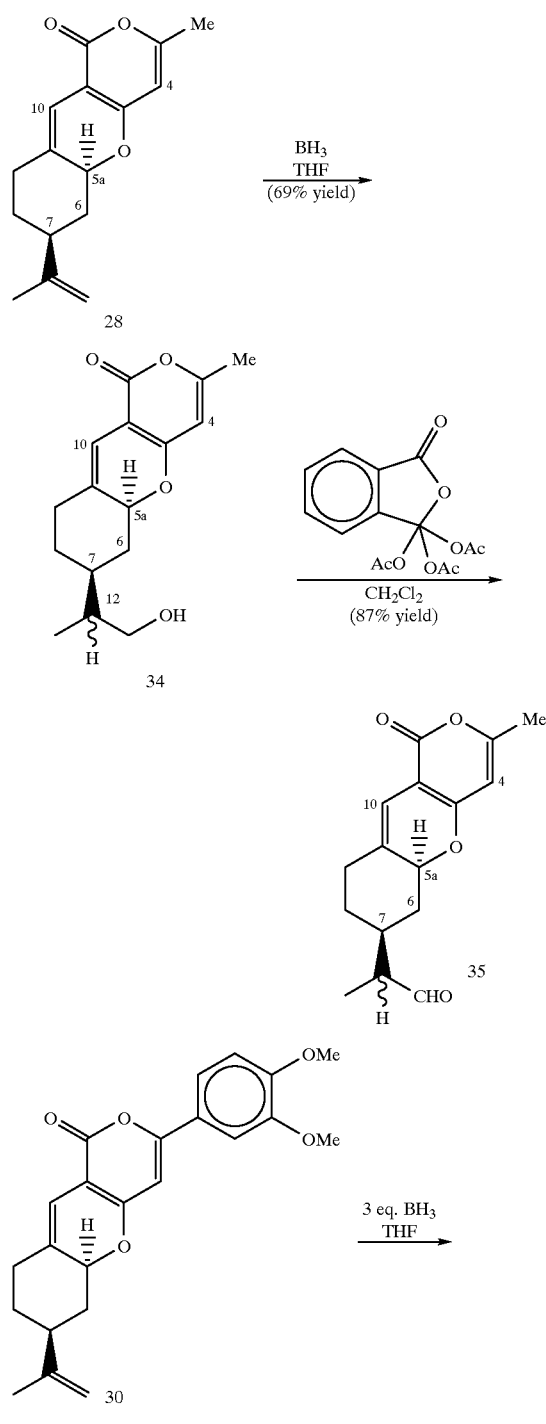
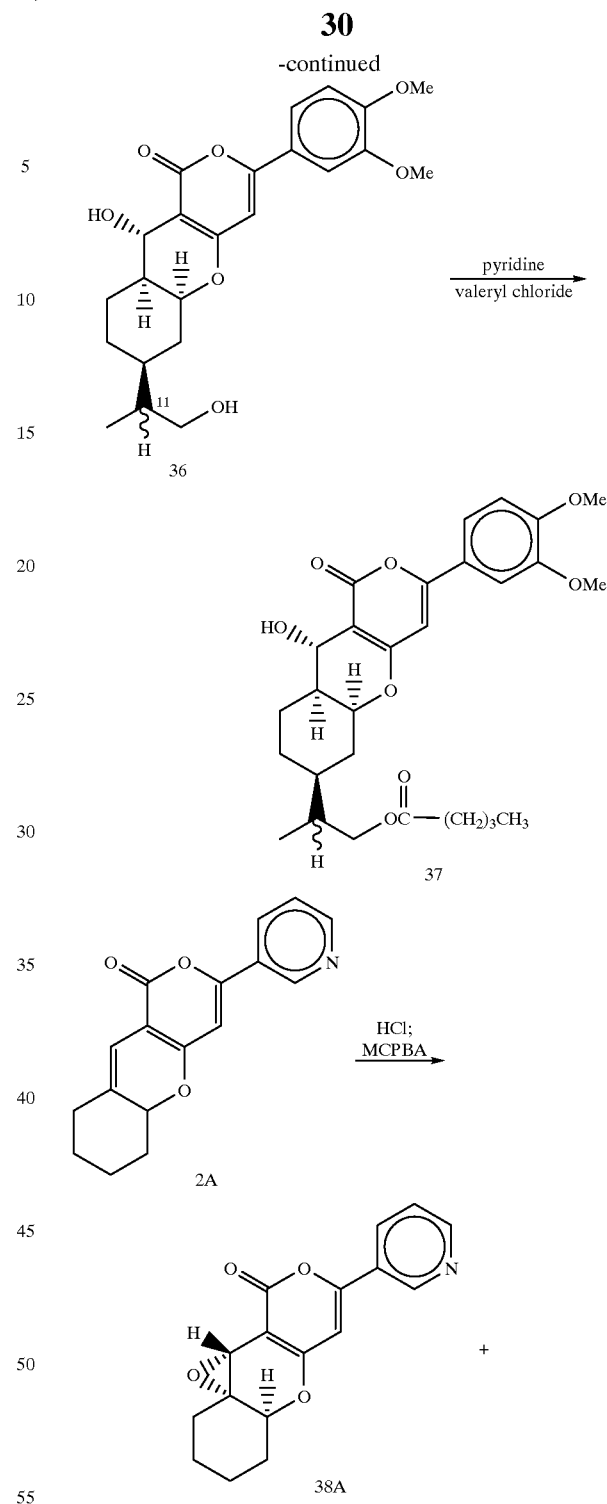

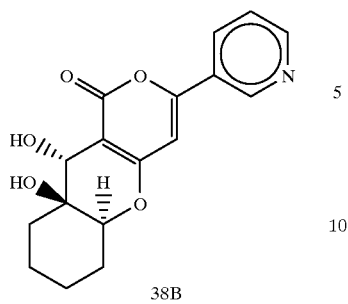

In addition to tricyclic pyrones, this invention provides a facile synthesis of tetracyclic pyrones (such as 46, Scheme 11). Treatment of (R)-carvone (39) with lithium diisopropylamide (LDA) in THF at −40° C. and MeI (−30° C.) gave an excellent yield of the corresponding C-6-monomethylated product. The regiospecific alkylation of carvone at C-6 is a known reaction (Gesson, J-P et al., "A New Annulation of Carvone to Chiral Trans and Cis Fused Bicyclic Ketones," Tetrahedron (1986) 27:4461–4464). Subsequently, alkylation of this methylated product with LDA in THF at 0° C., followed by I equivalent of hexamethyl-phosphoramide (HMPA), and cis-1-iodo-3-(methanesulfonyloxy)-1-propene (40) at 0° C. then room temperature gave a 73% yield of iodide 41 as a single diastereomer and 14% recovery of 6-monomnethylated carvone (Scheme 11). No other stereoisomer was detected. Cyclization of iodide 41 with palladium acetate, triphenylphosphine, silver carbonate, CO, and MeOH in DMF at 32° C. gave a 50% yield (isolated) of ester 42. Ester 42 was converted into its carboxylic acid 43 in 96% yield by the treatment with KOH in MeOH and water at 25° C. As far as we know, this is the shortest route for the synthesis of optically pure trans-decalinone derivatives, such as 42; in this synthesis, no protecting group is needed. Addition reaction of acid 43 with the lithiated anion of 9 in THF gave adduct 44 which can be converted into aldehyde 45. Condensation of 45 with pyrone 5B will give tetracyclic pyrone 46 (a new compound).

A 23% yield of the correspnding β-isomer, compound 47, was also isolated from the above palladiun-cyclization reaction. The stereochemistry of these compounds, 42 and 47, were firmly established by 2D NOESY spectroscopy and the results are depicted in structure 47 (Scheme 12). For example, in the 2D NOESY spectrum of the minor product, 47, NOE appears between C4a-H and C-10-methyl; and C-11-CH$_2$ and C-13-CH$_2$. The NMR signals of C-13 and C-10 methyls of 42 are close to each other, hence it is difficult to determine their NOE.

Scheme 11

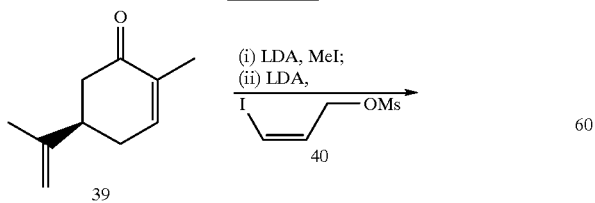

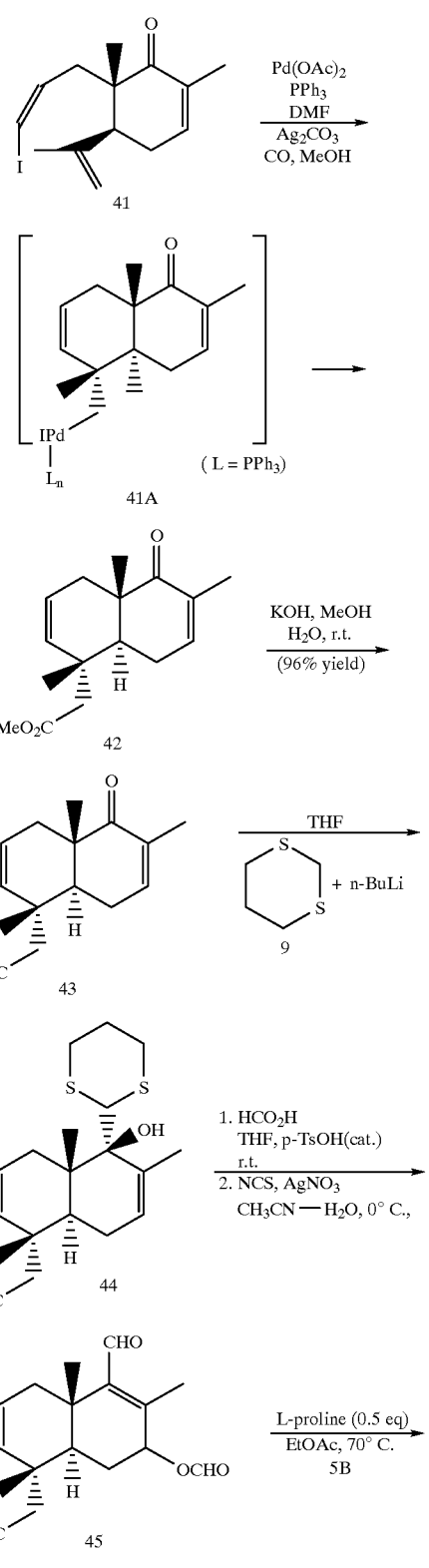

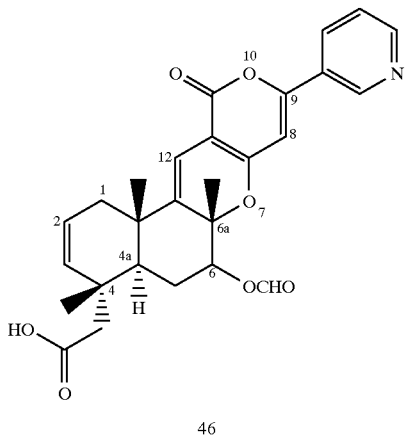

46

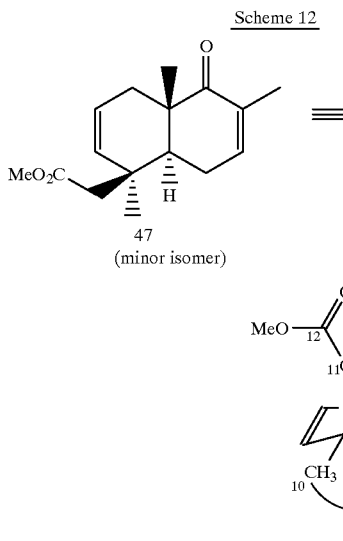

Scheme 12

47
(minor isomer)

NOE

Clearly, as will be appreciated by one skilled in the art, many other chemical manipulations can be carried out on the tricyclic and tetracyclic pyrones to produce various useful biologically active drugs. Additionally, the reactions illustrated in Schemes 1-11 can be modified to produce similar compounds, as will be appreciated by those skilled in the art.

The following examples illustrate the invention:

EXAMPLES

Compound Syntheses

General Methods. Nuclear magnetic resonance spectra were obtained at 400 MHz for $^1$H and 100 MHz for $^{13}$C in deuteriochloro-form, unless otherwise indicated. Infrared spectra are reported in wavenumbers ($cm^{-1}$). Mass spectra were taken from a Hewlett Packard 5890 Series II, GC-HPLC-MS. FAB spectra were taken by using Xe beam (8 KV) and m-nitrobenzyl alcohol as matrix. Davisil silica gel, grade 643 (200–425 mesh), was used for the flash column chromatographic separation. THF and diethyl ether were distilled over sodium and benzophenone before use. Methylene chloride was distilled over $CaH_2$ and toluene and benzene were distilled over $LiAlH_4$. Ethyl acetate was dried over $CaCl_2$ and filtered and distilled under argon atmosphere.

General Procedure for the Condensation of Pyrone and Enal

The following reaction procedures are representative of the condensation reactions of this invention.

cis- and trans-3,5a-Dimethyl-6-formyloxy-1H-5a,6,7,8 9-pentahydro-1-oxopyrano[4,3-b][1]benzopyran (1D and 1E)

A solution of 0.147 g (0.88 mmol) of aldehyde 4C, 0.11 g (0.88 mmol) of pyrone 5A, and 0.05 g (0.4 mmol) of L-proline in 10 mL of ethyl acetate was stirred under argon at 25° C. for 1 day, 40° C. (bath temperature) for 3 days, and 60° C. for 1 day. The mixture was diluted with 120 mL of methylene chloride, washed with 50 mL of saturated aqueous $NaHCO_3$, and then with 50 mL of brine, dried ($MgSO_4$), concentrated, and column chromatographed on silica gel using a gradient mixture of hexane and diethyl ether as eluant to give 0.1133 g (46.5% yield) of 1D and 0.0378 g (15.5% yield) of 1E. Compound 1D: mp 138–140° C. IR (Nujol) v 2980, 1720, 1690, 1630, 1550, 1110; $^1$H NMR δ 8.14 (d, J=1 Hz, 1 H, CHO), 6.18 (d, J=2.2 Hz, 1 H, C10 H), 5.73 (s, 1 H, C4 H), 5.31 (dd, J=11.6 Hz, 4.4 Hz, 1 H, C6 H, axial H), 2.39-2.33 (m, 1 H), 2.292.23 (m, 1 H), 2.19 (d, J=0.44 Hz, 3 H, Me), 2.12-2.05 (m, 1 H), 1.88-1.8 (m, 1 H), 1.7-1.5 (m, 2 H), 1.54 (s, 3 H, Me); $^{13}$C NMR δ 162.4 (s, C=O), 162.32 (s), 160.36 (s, 2C), 132.74 (s, C10a), 112.51 (d, C10), 100.08 (d, C4), 97.7 (s, C9a), 84.4 (s, C5a), 76.46 (d, C6), 31.3 (t), 29.26 (t), 23.12 (t), 20.31 (q, Me), 18.88 (q, Me); MS.FAB, m/z 277 (M+1, 100%), 230, 139, 91. Analysis calc for $C_{15}H_{16}O_5$: C, 65.21; H, 5.84. Found: C, 65.47; H, 5.61. Single crystals were obtained from the recrystallization in ether and the structure was unequivocally determined by an X-ray analysis.

Compound 1E: 1 H NMR δ 8.11 (d, J=0.92 Hz, 1 H, CHO), 6.23 (d, J=1.6 Hz, 1 H, C10 H), 5.72 (s, 1 H, C4 H), 2.44-2.28 (m, 2 H), 2.19 (d, J=0.6 Hz, 3 H, Me), 2.1-2.0 (m, 1 H), 1.9-1.64 (a series of m, 3 H), 1.57 (s, 3 H, Me); MS.FAB, m/z 277 (M+1, 100%). Basic hydrolysis of 1E with $K_2CO_3$ in MeOH gave the corresponding C6 alcohol having exact same NMR as the trans-alcohol obtained from the condensation of pyrone 5A and alcohol 4B.

3-Methyl-1H-5a,6,7,8,9-pentahydro-1-oxopyrano[4,3-b][1]benzopyran (1A).

A solution of 0.1 g (0.91 mmol) of cyclohexenecarboxaldehyde (4A), 0.115 g (0.91 mmol) of 4-hydroxy-6-methyl-2-pyrone (5A), and 0.052 g (0.455 mmol) of L-proline in 5 mL of ethyl acetate was heated at 70° C. under argon atmosphere for 24 h. The mixture was cooled to room temperature, diluted with 100 mL of methylene chloride, washed with saturated aqueous $NaHCO_3$ solution twice (30 mL each), with water (60 mL), and then with brine (60 mL), dried ($MgSO_4$), filtered, and concentrated to give 0.20 g of crude product. Column chromatography on silica gel of the crude product using a gradient mixture of hexane:ether as eluant gave 0.15 g (80% yield based on recovered starting pyrone) of 1A and 0.006 g (5% recovery) of 5A. Compound 1A: mp 110–112° C.; X-ray analysis was carried out on a single crystal obtained from the recrystallization from ether-hexane and the structure was solved. IR (Nujol) v 1710 (s, C=O), 1630 (C=C), 1560. $^1$H NMR δ6.07 (s, 1 H C10H), 5.7 (s, 1 H, C4H), 5.02 (dd, J=11, 5 Hz, 1H, C5aH), 2.41 (m, 1H, C9H), 2.18 (s, 3H, Me), 2.13 (m, 1H, C5aH), 2.02-1.88 (m, 2 H), 1.8-1.7 (m, 2H), 1.5-1.4 (m, 2H); $^{13}$C NMR δ 174 (s, C=O), 163.24 (s, C3), 161.38 (s, C4a), 133.06 (s, C10a), 109.17 (d, C10), 99.76 (d, C4), 97.33 (s, C9a), 79.69 (s, C5a), 35.15 (t, C9), 33.14 (t, C6), 26.89 (t, C7), 24.52 (t, C8), 20.06 (q, Me); MS (CI) m/z 219 (M+1). Analysis Calculated for $C_{13}H_{14}O_3$: C 71.54; H 6.47. Found: C, 71.39; H, 6.53.

Preparation of 2-methyl-2-cyclohexen-1-one (8)

A solution of 15 g (0.134 mol) of 2-methyl-1-cyclohexanone (7) and 23.84 g (0.134 mol) of N-bromosuccinimide in 150 mL of carbon tetrachloride was stirred and heated to reflux for 12 h under argon. The mixture was cooled to room temperature, filtered through Celite to remove succinimide and the filter cake was washed with 150 mL of ether. The filtrate was concentrated to give 25.6 g (100% yield) of 2-bromo-2-methyl-1-cyclohexanone. $^1$H NMR δ 3.21 (td, J=16 Hz, 8 Hz, 1 H, CH—CO), 2.36 (m, 2 H), 2.06 (m, 2 H), 1.82 (s, 3 H, Me), 1.77 (m, 2 H), 1.62 (m, 1 H).

A mixture of 25.6 g (0.134 mol) of the above 2-bromo-2-methylcyclohexanone, 29.7 (0.4 mol) of $Li_2CO_3$ and 34.9 g (0.4 mol) of LiBr in 300 mL of DMF was heated at 130° C. under argon for 3 h. The reaction mixture was cooled to room temperature, diluted with 400 mL of water, and extracted three times with ether (300 mL×2 and 200 mL). The combined extract was dried ($MgSO_4$), concentrated on a rotary evaporator to give 12.96 g of crude product which was subjected to vacuum distillation to give 10.6 g (72% yield) of 8, bp. 90–95° C./45 mm Hg; Lit. (Rinne, W. W. et al., "New Methods of Preparation of 2-methylcyclohexen-1-one," J. Am. Chem. Soc (1950) 72:5759–5760) 93–97° C./25 mm Hg; $^1$H NMR δ 6.75 (broad s, 1 H, =CH), 2.42 (dd, J=5.6 Hz, 5 Hz, 2 H), 2.33 (m, 2H), 1.95 (pent, J=8 Hz, 2 H), 1.78 (q, J=2 Hz, 3 H, Me); $^{13}$C NMR δ 199.88 (s, C=O), 145.61 (d, =CH), 135.65 (s, =C), 38.33 (t), 26.04 (t), 23.32 (t), 15.97 (t).

1-[2-(1,3-Dithianyl)]-2-methyl-2-cyclohexen-1-ol (10)

To a cold (−10° C.) solution of 6.71 g (55.9 mmol) of 1,3-dithiane (9; commercially available) in 50 mL of THF under argon was added 24.6 mL (55.9 mmol; from a 2.27 M solution in hexane) of n-BuLi dropwise via syringe over 35 minutes and the resulting solution was stirred for 2 hours. In a separate flask, a solution of 4.10 g (37.7 mmol) of 8 in 25 mL of THF was prepared and this solution was added via cannula into the above dithiane anion solution. The solution was stirred at −10C. for 1 h and kept in the refrigerator for 18 h, diluted with 100 mL of water, stirred for 10 minutes, and extracted three times with diethyl ether (100, 75, and 50 mL). The combined extract was washed twice with brine (2×100 mL), dried ($MgSO_4$), filtered, concentrated to give 13.147 g of crude product. Column chromatographic separation on silica gel using a gradient mixture of hexane:ether as eluant gave 8.208 g (96% yield) of 10 as an oil. $^1$H NMR δ 5.74 (t, J=4 Hz, 1 H, =CH), 4.42 (s, 1 H, CH—S), 3.0-2.8 (m, 4 H $CH_2$—S), 2.28 (s, 1 H, OH), 2.16–1.6 (series of m, 8 H), 1.82 (broad s, 3 H, Me); $^{13}$C NMR δ 133.81 (s, =C), 130.25 (d, =CH), 74.04(s, CO), 59.13 (d, CH—S), 33.88 (t, $CH_2S$), 31.78 (t, $CH_2S$), 31.33 (t, $CH_2$), 26.37 (t, $CH_2$), 25.61 (t, $CH_2$), 18.73 (t, $CH_2$), 17.75 (q, Me); MS (EI) m/z 230 (M$^+$).

3-[2-(1,3-Dithianyl)]-2-methyl-2-cyclohexen-1-ol (11)

A solution of 1.031 g (4.48 mmol) of alcohol 10 in 50 mL of p-dioxane and 75 mL of 1% aqueous solution of $H_2SO_4$ was stirred at 25° C. for 5.5 h, and then extracted three times with diethyl ether (100 mL each). The combined extract was washed with 80 mL of saturated aqueous $NaHCO_3$, twice with water (80 mL each) and 80 mL of brine, dried ($MgSO_4$), concentrated, and column chromatographed on silica gel using a gradient mixture of hexane and diethyl ether as solvent to give 0.533 g (58% yield based on recovered starting material 10) of 11 as an oil and 0.11 g (11% recovery) of 10. Compound 11: $^1$H NMR δ 5.09 (s, 1 H, CHS), 3.97 (broad s, 1 H, CHO), 3.04-2.95 (m, 2 H, $CH_2S$), 2.87-2.81 (m, 2 H, $CH_2S$), 2.32-2.24 (m, 1 H), 2.16-2.07 (m, 2 H), 1.91 (t, J=4 Hz, 3 H, Me), 1.89-1.58 (a series of m, 5 H); 13C NMR δ 132.89 (s, C=), 131.85 (s, =C), 69.6 (d, CO), 51.11 (d, CHS), 31.81 (t), 31.36 (2 C, t, $CH_2S$), 26.6 (t), 25.45 (t), 18.48 (t), 16.41 (q, Me); MS (EI) m/z 230 (M+). Analysis Calc. for $C_{11}H_{18}OS_2$: C, 57.35; H, 7.87. Found: C, 57.56; H, 8.10.

3-Hydroxy-2-methyl-1-cyclohexen-1-carboxaldehyde (4B)

To a flask containing a stirring bar, 0.197 g of $AgNO_3$ (1.16 mmol) and 0.139 g (1.04 mmol) were added and the content was dried under vacuum, maintained under argon atmosphere, and 6 mL of $CH_3CN$ and 2.5 mL of $H_2O$ were added. The flask was stirred and cooled over ice-water bath, and a solution of 0.059 g (0.26 mmol) of 11 in 5 mL of acetonitrile was added dropwise via cannula. The solution was stirred at 0° C. for 45 min, and 1 mL each of saturated aqueous $Na_2SO_3$ and $Na_2CO_3$ were added at 1 min interval, and then 20 mL of a 1:1 mixture of $CH_2Cl_2$ and petroleum ether was also added. The resulting mixture was filtered through Celite and the solid carefully washed with 120 mL of 1:1 mixture of $CH_2Cl_2$ and petroleum ether. The filtrate was transferred into a separatory funnel and the water layer was removed. The organic layer was washed with 10 mL of saturated aqueous $NAHCO_3$, dried ($MgSO_4$), concentrated to give 31.5 mg of the crude aldehyde 4B. The $^1$H NMR spectrum of the crude product indicated 18 mg (50% yield) of the desired aldehyde and 13 mg of succinimide. This material can be used directly in the next reaction without further purification. In a separated reaction, the mixture was separated on silica gel flash column chromatography and provided 18 mg (50% yield) of pure 4B. Aldehyde 4B is not a stable compound and elemental analysis was not performed. $^1$H NMR δ 10.18 (s, 1 H, CHO), 4.16 (broad s, 1 H, CH—O), 2.27 (s, 3 H, Me), 2.31-1.6 (a series of m, 6 H); $^{13}$C NMR δ 192.37 (s, C=O), 154.24 (s, C=), 134.96 (s, C=), 70.32 (d, C-O), 31.79 (t), 22.7 (t), 17.91 (t), 14.85 (q, Me); MS, FAB m/z 141 (M+1, 100%), 140 (M+).

3-Formyloxy-2-methyl-1-cyclohexen-1-carboxaldehyde (4C)

A solution of 0.494 g (2.15 mmol) of alcohol 10 and three crystals of p-toluenesulfonic acid (anhydrous) in 2.43 mL of formic acid and 15 mL of THF was stirred under argon at 25° C. for 16 h. The solution was diluted with 100 mL of diethyl ether, washed with 40 mL of saturated aqueous $NaHCO_3$, and 50 mL of brine, dried ($MgSO_4$), concentrated, and column chromatographed on silica gel using a gradient mixture of hexane and diethyl ether as eluant to give 0.388 g (70% yield) of 1-[2-(1,3-dithianyl)]-3-formyloxy-2-methyl-1-cyclohexene and 0.048 g (9% yield) of alcohol 11. 1-[2-(1,3-dithianyl)]-3-formyloxy-2-methyl-1-cyclohexene: $^1$H NMR δ 8.12 (s, 1 H, CHO), 5.36 (broad s, 1 CHO), 5.1 (s, 1 H, CHS), 3.05-2.95 (m, 2 H, $CH_2S$), 2.9-2.8 (m, 2 H, $CH_2S$), 2.4-2.3 (m, 1 H), 2.2-2.05 (m, 2 H), 1.94-1.6 (m, 5 H), 1.78 (s, 3 H, Me); $^{13}$C NMR δ 160.97 (s, C=O), 135.18 (s, C=), 128.43 (s, C=), 71.68 (d, C—)), 50.95 (d, CS), 31.34 (t, 2 C, CS), 28.7 (t), 26.43 (t), 25.42 (t), 18.55 (t), 16.31 (q, Me); MS, FAB m/z 259 (M+1), 258 (M+).

To a dried 100 mL-round-bottomed flask 1.19 g (7 mmol) of $AgNO_3$, 0.828 g (6.2 mmol) of N-chlorosuccinimide, 40 mL of $CH_3CN$ and 16 mL of $H_2O$ were added under argon, and the solution was stirred and cooled over ice-water bath. To it, a solution of 0.4 g (1.55 mmol) of 1-[2-(1,3-dithanyl)]-3-formyloxy-2-methyl-1-cyclohexene in 10 mL of $CH_3CN$ was added dropwise over 30 min. To the reaction solution, 2 mL saturated aqueous solution of $Na_2SO_3$, 2 mL of saturated aqueous NaCl solution, and 20 mL of a 1:1 mixture of $CH_2Cl_2$:petroleum ether were added sequentially at 1 minute intervals. The whole mixture was then filtered through Celite, washed with 100 mL of CH$_2$Cl$_2$ and petroleum ether. The filtrate was transferred into a separatory funnel, the water layer was separated and extracted with 40 mL of CH$_2$Cl$_2$. The combined organic layers were dried (MgSO$_4$), filtered, concentrated, and column chromatographed on silica gel using a gradient mixture of hexane and diethyl ether as eluant to give 0.154 g (59% yield) of pure 4C; IR (neat) ν 2750, 1720, 1680 (C=O); $^1$H NMR δ 10.2 (s, 1 H, CHO), 8.18 (d, J=0.8 Hz, 1 H, formyloxy CH), 5.53 (t, J=4.8 Hz, 1 H, CH—O), 2.39-2.3 (m, 1 H), 2.14 (s, 3 H, Me), 2.17-2.08 (m, 1 H), 1.94-1.6 (a series of m, 4 H); $^{13}$C NMR δ 191.59 (s, C=O aldehyde), 160.66 (s, C=O of formyloxy), 148.69 (s, C=), 137.36 (s, C=), 71.72 (d, CH—O), 28.57 (t), 22.48 (t), 17.89 (t), 14.76 (q, Me); MS, FAB m/z 169 (M+1), 168 (M+).

Ethyl 5-(3-pyridyl)-3,5-dioxopentanoate (13A)

To a cold (−10° C.) solution of 13.45 mL (96.2 mmol) of diisopropylamine in 150 mL of diethyl ether under argon was added 42.36 mL (96.2 mmol; 2.27 M solution in hexanes) of n-BuLi via syringe and the solution was stirred for 1 h. In a separated flask, 5 g (38.5 mmol) of freshly distilled ethyl acetoacetate and 60 mL of diethyl ether were added and the solution was cooled to −78° C. To it, the above LDA solution was added via cannula, then 5.8 mL (38.5 mmol) of N,N,N',N'-tetramethylethylenediamine (TMEDA) (distilled from LiAlH$_4$) was added via syringe, and the solution was stirred at 0° C. for 3 h. To this dianion solution, a solution of 5.81 g (38.5 mmol) of ethyl nicotinate (freshly distilled) in 60 mL of diethyl ether was added via cannula and the reaction solution was warmed to room temperature and stirred for 30 h. To the solution, 5.5 mL of acetic acid was added and stirred for 10 min, filtered through fritted funnel, and the solid (desired product; exists as a protonated salt) was washed with 200 mL of diethyl ether. The filtrate was concentrated to give 1.691 g of material and the NMR spectrum indicated that it is a mixture of starting material and some unidentified components. The solid was transferred into a beaker and dissolved in 160 mL of distilled water and 60 mL of 1 N HCl, and extracted three times with methylene chloride (120 mL each). The combined extract was washed with 100 mL of brine, dried (MgSO$_4$), concentrated to give 7.921 g (87.5% yield) of the desired product 13A. $^1$H NMR spectrum of this material indicated it is sufficiently pure and can be used in the next reaction without purification. Mp 38.5-39° C.; $^1$H NMR δ 9.07 (s, 1 H, C-2' H, pyr.), 8.74 (d, J=4.6 Hz, 1H, C6'H, pyr.), 8.16 (d, J=8 Hz, C4'H), 7.41 (dd, J=8 Hz, 4.6 Hz, C5'H), 6.32 (s, 1 H, =CH of enol; the compound completely exists as enol form at C4), 4.22 (q, J=7.2 Hz, 2 H, OCH$_2$), 3.5 (s, 2 H, CH$_2$—C=O), 1.3 (t, J=7.2 Hz, 3 H, Me); $^{13}$C NMR δ 189.93 (s, C=O, C3), 179.97 (s, O—C=, C5), 167.11 (s, C=O ester), 152.74 (d, C2'), 148.13 (d, C6'), 134.3 (d, C4'), 129.7 (s, C3'), 123.41 (d, C5'), 97.18 (d, =CH, C4), 61.39 (t, OCH$_2$), 45.66 (t, CH$_2$), 13.93 (q, Me); MS.FAB, m/z 236 (M+1), 235 (M+).

4-Hydroxy-6-(3-pyridyl)-2-pyrone-(5B)

To a flask equipped with an adaptor connecting to a manifold, 0.594 g (2.53 mmol) of ester 13A was added while the flask was maintained under argon. The flask was then connected to a vacuum set at 3 mm Hg pressure and heated over an oil bath at 150° C. The flask was kept at this temperature for 0.5 h and then cooled to room temperature. Diethyl ether was added to the crude product and filtered, washed with diethyl ether. The solid after drying under vacuum gave 0.38 g (89% yield based on recovered starting ester 13A) of 5B. The filtrate was concentrated and column chromatographed to give 0.065 g (10.9% recovery) of starting ester 13A. Compound 5B: mp 187–189° C.; Lit. (Narashimhan, N. S. and Ammanamanchi, R., "Mechanism of acylation of dilithium salts of β-ketoesters: an efficient synthesis of anibine," J. Org. Chem. (1983) 48:3945–3947) 254–255° C.; $^1$H NMR(CDCl$_3$ and DMSO-d6) δ 9.03 (s, 1 H, C2'H), 8.67 (d, J=5.2 Hz, 1 H, C6'H) pyr ring), 8.13 (d, J=8 Hz, 1 H, C4'H), 7.41 (dd, J=8 Hz, 5.2 Hz, 1 H, C5'H), 6.56 (d, J=1.6 Hz, 1 H, C3 H), 5.62 (d, J=1.6 Hz, 1 H, C5 H); MS.FAB, m/z 190 (M+1), 189 (M+).

Methyl 5-(3,4-dimethoxyphenyl)-3,5-dioxopentanoate (13B)

To a cold (−20° C.) solution of 8.9 mL (63.7 mmol) of diisopropylamine in 100 mL of diethyl ether under argon was added 28.1 mL (63.7 mmol; 2.27 M solution in hexanes) of n-BuLi via syringe and the solution was stirred at 0° C. for 45 min. In a separated flask, 3.315 g (25.5 mmol) of freshly distilled ethyl acetoacetate and 50 mL of diethyl ether were added and the solution was cooled to −78° C. To it, the above LDA solution was added via cannula, then 3.84 mL (25.5 mmol) of N,N,N',N'-tetramethylethylenediamine (TMEDA) (distilled from LiAlH$_4$) was added via syringe, and the solution was stirred at 0° C. for 3 h. To this dianion solution, a solution of 5.0 g (25.5 mmol) of methyl 3,4-dimethoxybenzoate in 50 mL of diethyl ether was added via cannula and the reaction solution was warmed to room temperature and stirred for 40 h. The reaction mixture was filtered through fritted funnel, and the solid (desired product) was saved. The organic filtrate from the above filtration was washed with a solution of 50 mL of 1N HCl and 50 mL of distilled water, and then with 80 mL of brine, dried (MgSO$_4$), and concentrated to give the desired product, 5-(3,4-dimethoxyphenyl)-3,5-dioxopentanoic acid. The solid obtained above was dissolved in 80 mL of distilled water and 10 mL of 1N HCl solution, and washed twice with methylene chloride (100 mL each). The water layer was further acidified with 100 mL of 1N HCl, extracted twice with methylene chloride (50 mL each). The combined methylene chloride extract was washed with 80 mL of brine, dried (MgSO$_4$), concentrated to give the desired carboxylic acid [5-(3,4-dimethoxyphenyl)-3,5-dioxopentanoic acid]. This acid and the above acid from the filtrate were combined and dissolved in 50 mL of CH$_2$Cl$_2$, cooled over ice-water bath, and a solution of diazomethane in diethyl ether was added dropwise until the carboxylic acid was no longer present. The solution was concentrated on a rotary evaporator and dried under vacuum, and column chromatographed on silica gel using a gradient mixture of hexane and ethyl acetate as eluant to give 3.798 g (56% yield) of pure 13B. $^1$H NMR δ 7.51 (dd, J=8.5 Hz, 2 Hz, 1 H, C5' H, Ar), 7.45 (d, J=2 Hz, 1 H, C2' H), 6.9 (d, J=8.5 Hz, 1 H, C6' H), 6.24 (s, 1 H, =CH of enol at C4& 5), 3.95 (s, 6 H, 2 OMe on Ar ring), 3.77 (s, 3 H, MeO), 3.47 (s, 2 H, CH$_2$); $^{13}$C NMR δ 186.18 (s, C3 C=O), 184.05 (s, C5=C—O), 168.21 (s, C=O ester), 153.16 (s, C4' Ar), 149.07 (s, C3' Ar), 127.04 (s, Cl' Ar), 121.49 (d, C2'), 110.56 (d, C5'), 109.66 (d, C6'), 96.17 (d, C4 =CH), 56.06 (q, OMe), 56.0 (q, OMe), 52.32 (q, OMe of ester), 44.89 (t, CH$_2$); MS.FAB, m/z 281 (M+1), 280 (M+).

4-Hydroxy-6-(3,4-dimethoxyphenyl)-2-pyrone (5C)

A flask containing the methyl ester 13B (2.2 g; 7.86 mmol) was connected into a vacuum system to provide −3 mmHg pressure and heated over an oil bath to 160° C. over a one hour period. The reaction was kept at this temperature for another one hour, cooled to room temperature, diluted with a small amount of ether and filtered to collect the yellow solids, washed with ether, and the solids were dried under vacuum to give 1.04 g (70.5% yield based on recovered starting material 13B) of pyrone 5C and 0.534 g (24% recovery) of starting ester 13B. Compound 5C: mp 210–212° C., $^1$H NMR δ 7.40 (dd, J=8.3 Hz, 2 Hz, 1 H, C6' of the phenyl ring), 7.33 (d, J=2 Hz, 1 H, C2' of Ph ring), 6.91 (d, J=8.3 Hz, 1 H, C5'), 6.40 (s, C3 H), 5.55 (s, 1 H, C5 H), 3.95 (s, 3 H, OMe), 3.94 (s, 3 H, OMe); MS.FAB, m/z 249 (M+1), 248 (M+).

cis- and trans-3,5a-Dimethyl-6-hydroxy-1H-5a,6,7,8,9-pentahydro-1-oxopyrano[4,3-b][1]-benzopyran (1B and 1C)

From 0.024 g (0.188 mmol) of aldehyde 4B and 23.7 mg (0.188 mmol) of pyrone 5A, heating with 3 mL of ethyl acetate and 3 drops (~15 mg) of piperidine and 3 drops of acetic acid at 80° C. for 18 h, 0.033 g (72% yield) of a mixture of 1B and 1C in a ratio of 1.6:1 (obtained from $^1$H NMR spectrum) was obtained. Compound 1B: $^1$H NMR δ 6.13 (d, J=2 Hz, 1 H, C10 H), 5.77 (s, 1 H, C4 H), 4.07 (dd, J=8.4 Hz, 3.4 Hz, 1 H, C5a H), 2.36–2.16 (a series of m, 2 H), 2.21 (s, 3 H, C3 Me), 2.14 (broad s, 1 H, OH), 1.98-2.04 (m, 1 H), 1.83–1.76 (m, 1 H), 1.56-1.42 (m, 2 H), 1.47 (s, 3 H, C5a Me); $^{13}$C NMR δ 162.42 (s, C1), 162.08 (s, C4a), 158 (s, C3), 134.17 (s, C10a), 111.67 (d, C10), 100.13 (d, C4), 98.08 (s, C9a), 87.07 (s, C5a), 76.16 (d, C6),31.59 (t), 30.94 (t), 23.20 (t), 20.36 (q, Me), 17.52 (q, Me); MS.FAB, m/z 249 (M+1), 248 (M+). Compound IC: $^1$H NMR δ 6.23 (d, J=3 Hz, 1 H, C10 H), 5.80 (s, 1 H, C4 H), 3.87 (t, J=1 Hz, 1 H, CSa H), 2.21 (s, 3 H, C3 Me), 1.44 (s, 3 H, C5a Me), 2.4-1.5 (a series of m, 6 H); MS.FAB, m/z 249 (M+1), 248 (M+).

3-(3-Pyridyl)-1H-5a,6,7,8,9-pentahydro-1-oxopyrano[4,3-b][1]benzopyran (2A)

From 0.344 g (1.82 mmol) of pyrone 5B and 0.2 g (1.82 mmnol) of aldehyde 4A, 0.373 g (73% yield) of 2A was obtained after column chromatographic separation. IR (Nujol) v3070, 1690, 1620, 1540, 1200, 1060, 1020. $^1$H NMR δ 8.99 (d, J=2 Hz, 1 H, Pyr.), 8.65 (dd, J=4.9 Hz, 2 Hz, 1 H, C6'H), 8.1 (dt, J=8 Hz, 2 Hz, 1 H, C4'H), 7.38 (dd, J=8 Hz, 4.9 Hz, 1 H, C5'H), 6.44 (s, 1 H, C10H), 6.14 (s, 1 H, C4 H), 5.14 (dd, J=11 Hz, 5 Hz, 1 H, C5a H), 2.47 (m, 1H, C9 H), 2.19 (m, 1 H, C9 H), 2.03 (m, 1 H), 1.94 (m, 1 H), 1.86-1.76 (m, 2 H), 1.5 (dt, J=13 Hz, 3.4 Hz, 1 H), 1.37 (dt, J=13 Hz, 3.4 Hz, 1 H); $^{13}$C NMR δ 162.63 (s, C1), 161.44 (s, C4a), 156.51 (s, C3), 151.22 (d, C2'), 146.73 (d, C6'), 134.94 (s, C3'), 132.84 (d, C4'), 127.56 (s, C10a), 123.73 (d, C5'), 109.22 (d, C10), 99.84 (s, C9a), 98.57 (d, C4), 80.08 (d, C5a), 35.34 (t, C9), 33.38 (t, C6), 27.01 (t, C7), 24.62 (t, C8); MS.FAB, m/z 282 (M+1, 100%), 281 (M+), 252, 202, 148, 136, 106. Anal. Calc. for $C_{17}H_{15}NO_3$: C, 72.58; H, 5.37. Found: C, 72.33; H, 5.42.

3-(3,4-Dimethoxyphenyl)-1H-5a,6,7,8,9-pentahydro-1-oxopyrano[4,3b]-[1]benzopyran (3A)

From 0.2 g (0. 81 mmol) of 5C and 0.135 g (0.81 mmol) of aldehyde 4A, 0.20 g (62% yield) of 3A was obtained after column chroinatographic separation. Mp. 137–138° C.; IR (Nujol) v 3010, 3050, 1700, 1650, 1630, 1560, 1520, 1280, 1240, 1150; $^1$H NMR δ 7.37 (dd, J=8.5 Hz, 2 Hz, 1 H, C6'H, Ph ring), 7.28 (d, J=2 Hz, 1 H, C2'H), 6.9 (d, J=8.5 Hz, 1 H, C5'H), 6.29 (s, 1 H, C10 H), 6.14 (s, 1 H, C4 H), 5.07 (dd, J=11.4 Hz, 5.2 Hz, 1 H, C5a H), 3.94 (s, 3 H, OMe), 3.93 (s, 3 H, OMe), 2.45 (d, J=14 Hz, 1 H, C9 H), 2.18 (m, 1 H), 2.02 (m, 1 H), 1.92(m, 1H), 1.78 (m, 2 H), 1.54-1.34 (m, 2 H); $^{13}$C NMR δ 163.44 (s, C1), 161.95 (s, C4a), 159.28(s, C3), 151.3 (s, C4', Ph ring), 149.16 (s, C3'), 133.61 (s, C1'), 124.13 (s, C10a), 118.89 (d, C2'), 111.05 (d, CS'), 109.38 (d, C10), 108.12 (d, C6'), 98.05 (s, C9a), 96.1 (d, C4), 79.75 (d, C5a), 56.12 (q, OMe), 56.04 (q, OMe), 35.25 (t, C9), 33.25 (t, C6), 26.95 (t, C7), 24.58 (t, C8); MS.FAB, m/z 341 (M+1, 100%), 340 (M+), 307, 289, 261, 235, 219. Anal. Calc. for $C_{20}H_{20}O_5$: C,70.58; H, 5.92. Found: C,70.31; H, 6.11.

cis- and trans-3-(3-Pyridyl)-5a-methyl-6-hydroxy-1H-5a,6,7,8,9-pentahydro-1-oxopyrano[4,3-b][1]-benzopyran (2B and 2C) and cis- and trans-3-(3-pyridyl)-5a-methyl-6-formyloxy-1H-5a,6,7,8,9-pentahydro-1-oxopyrano[4,3-b][1]-benzopyran (2D and 2E):

Condensation of 0.073 g (0.39 mmol) of pyrone 5 B and 0.065 g (0.39 mmol) of aldehyde 4C in the presence of 0.023 g (0.19 ininol) of L-proline in 5 mL of ethyl acetate under argon at 70° C. was carried out for 3 days and then 3 mL of N,N-dimethylformamide (DMF) was added and the reaction mixture was heated at the same temperature for another 3 days. After aqueous work-up as described in the general procedure, 0.131 g of crude product was obtained. Column chromatographic separation of this material afforded 39% yield of formates 2D and 2E (in a ratio of 2:1) and 11% yield of alcohols 2B and 2C (ratio of 2:1). Compounds 2D and 2E, and 2B and 2C are separable by a careful silica-gel column chromatography to give 34 mg (26% yield) of 2D, 17 mg (13% yield) of 2E, 9 mg (7.3% yield) of 2B, and 4 mg (3.7% yield) of 2C. Compounds 2B and 2C were probably formed from the hydrolytic reaction with trace amount of $H_2O$ contained in DMF.

Compound 2D: Mp. 160–161° C.; $^1$H NMR δ 9.0 (d, J=2 Hz, 1 H, C2' H, pyr.), 8.66 (dd, J=5 Hz, 2 Hz, 1 H, C6'H), 8.18 (s, 1 H, CHO), 8.09 (dt, J=8 Hz, 2 Hz, 1 H, C4'H), 7.39 (dd, J=8 Hz, 5 Hz, 1 H, C5'H), 6.46 (s, 1 H, C10H), 6.26 (s, 1 H, C4H), 5.38 (dd, J=12 Hz, 5 Hz, 1 H, C6H), 2.42 (m, 1 H, C9H), 2.3 (m, 1 H, C9H), 2.12 (m, 1 H), 1.88 (m, 1 H), 1.7-1.52 (m, 2 H), 1.60 (s, 3 H, Me); $^{13}$C NMR δ 161.5 (s, C1), 160.14 (d, s, 2 C, CHO & C4a), 157.12 (s, C3), 151.33 (d, C2', pyr.), 146.72 (d, C4'), 134.2 (d, C3'), 132.8 (d, C4'), 127.31 (s, C10a), 123.6 (d, C5'), 112.25 (d, C10), 99.82 (s, C9a), 98.5 (d, C4), 84.61 (s, C5a), 76.18 (d, C6), 31.25 (t, C9), 29.07 (t, C7), 22.85 (t, C8), 18.85 (q, Me); MS.FAB, m/z 340 (M+1, 100%), 293, 278, 266, 240, 202, 173. Anal. Calc. for $C_{19}H_{17}NO_5$: C, 67.25; H, 5.05. Found: C, 67.07; H, 5.29.

Compound 2E: $^1$H NMR δ 9.0 (d, J=2 Hz, 1 H, C2'H, pyr.), 8.66 (dd, J=5 Hz, 2 Hz, 1 H, C6'H), 8.14 (s, 1 H, CHO), 8.10 (dt, J=8 Hz, 2 Hz, 1 H, C4'H), 7.39 (dd, J=8 Hz, 5 Hz, 1 H, C5'H), 6.45 (s, 1 H, C10H), 6.31 (s, 1 H, C4H), 5.28 (broad s, 1 H, C6H), 2.46-1.5 (a series of m, 6 H), 1.64 (s, 3 H, Me); MS.FAB, m/z 340 (M+1, 100%).

Compound 2B: $^1$ H NMR δ 9.0 (d, J=2 Hz, 1 H, C2'H, pyr.), 8.66 (d, J=4 Hz, 1 H, C6'H), 8.10 (dt, J=8 Hz, 2 Hz, 1 H, C4'H), 7.39 (dd, J=8 Hz, 4 Hz, 1 H, C5'H), 6.51 (s, 1 H, C10H), 6.20 (d, J=2 Hz, 1 H, C4H), 4.14 (dd, J=12 Hz, 4.4 Hz, 1 H, C6H), 2.42-1.4 (a series of m, 6 H), 1.54 (s, 3 H, Me); Anal. Calc. for $C_{18}H_{17}NO_4$: C, 69.44; H, 5.50. Found: C, 69.17; H, 5.21.

Compound 2C: $^1$H NMR δ 9.0 (d, J=2 Hz, 1 H, C2'H, pyr.), 8.66 (d, J=4 Hz, 1 H, C6'H), 8.10 (dt, J=8 Hz, 2 Hz, 1 H, C4'H), 7.39 (dd, J=8 Hz, 4 Hz, 1 H, C5'H), 6.32 (s, 1 H, C10H), 6.20 (d, J=2 Hz, 1 H, C4H), 3.94 (broad s, 1 H, C6H), 2.42-1.4 (a series of m, 6 H), 1.51 (s, 3 H, Me); MS.FAB, m/z 312 (M+1, 100%).

cis- and trans-3-(3,4-Dimethoxyphenyl)-5a-methyl-6-hydroxy-1H-5a,6,7,8,9-pentahydro-1-oxopyrano[4,3b][1]-benzopyran (3B and 3C)

Condensation of 0.103 g (0.41 mmol) of pyrone SC and 0.058 g (0.41 mmol) of hydroxy aldehyde 4B gave 3B and 3C in a ratio of 2:1. Column chromnatographic separation gave pure 3B and 3C.

Compound 3B: $^1$H NMR δ 7.39 (dd, J=8 Hz, 2 Hz, 1 H, C6', Ph), 7.29 (d, J=2 Hz, C2'H), 6.9 (d, J=8 Hz, 1 H, C5'H), 6.37 (s, 1 H, C10H), 6.2 (d, J=2 Hz, 1 H, C4H), 4.12 (dd, J=12 Hz, 5 Hz, 1 H, C6H), 3.94 (s, 3 H, OMe), 3.93 (s, 3 H, OMe), 2.36 (m, 1 H), 2.26 (m, 1 H), 2.04 (m, 1 H), 1.82 (I, 1 H), 1.6-1.46 (m, 2 H), 1.51 (s, 3 H, Me); MS.FAB, m/z 371 (M+1, 100%), 370 (M+), 355, 325, 307, 261, 219, 207. Anal. Calc. for $C_{12}H_{22}O_6$: C, 68.10; H, 5.99. Found: C, 67.89; H, 5.73.

Compound 3C: $^1$H NMR δ 7.38 (dd, J=8 Hz, 2 Hz, 1 H, C6', Ph), 7.29 (d, J=2 Hz, C2'H), 6.9 (d, J=8 Hz, 1 H, C5'H), 6.37 (s, 1 H, C1OH), 6.31 (d, J=2 Hz, 1 H, C4H), 3.92 (m, 1 H, C6H), 3.94 (s, 3 H, OMe), 3.93 (s, 3 H, OMe), 2.53 (broad s, 1 H, OH), 2.42 (1 H), 2.3 (m, 1 H), 2.08 (m, 1 H), 1.88 (m, 1 H), 1.77 (m, 1 H), 1.58 (m, 1 H), 1.49 (s, 3 H, Me); $^{13}$C NMR δ 162.29(s, Cl), 161.6 (s, C4a), 159.52 (s, C3), 151.4 (C4', Ph), 149.19 (s, C3'), 133.87 (s, C1'), 124.01(s, C10a), 118.9 (d, C2'), 112.65 (d, C5'), 111.04 (d, C10), 108.17 (d, C6'), 99.07 (s, C9a), 96.18 (d, C4), 85.62 (s, C5a), 73.07 (d, C6), 56.10 (q, OMe), 55.99 (q, OMe), 31.21 (t, C9), 29.03 (t, C7), 22.62 (t, C8), 19.56 (q, Me); MS.FAB, m/z 371 (M+1, 100%), 370 (M+).

cis- and trans-3-(3,4-Dimethoxyphenyl)-6-formyloxy-5a-methyl-1H-5a,6,7,8,9-pentahydro-1-oxopyrano[4,3-b][1]-benzopyran (3D and 3E)

From 0.062 g (0.25 mmol) of pyrone 5C and 0.042 g (0.25 mmol) of aldehyde 4C, 48 mg (48% yield) of a 2:1 mixture of formyloxy derivatives 3D and 3E, and 22 mg (24% yield) of a 2:1 mixture of alcohol 3B and 3C were obtained after column chromatographic separation.

Compound 3D: IR (Nujol) ν 3080, 1690 (s, C=O), 1640, 1610, 1595, 1535, 1485, 1310, 1255, 1170, 1130, 1010, 970, 955, 845, 790; $^1$H NMR δ 8.20 (s, 1H, CHO), 7.40 (dd, J=8 Hz, 2 Hz, 1 H, C6'H,Ph), 7.27 (d, J=2 Hz, 1 H, C2'H), 6.90 (d, J=8 Hz, 1 H, C5'H), 6.32 (s, 1 H, C1OH), 6.24 (d, J=2 Hz, 1 H, C4H), 5.34 (dd, J=12 Hz, 4.6 Hz, 1 H, C6H), 3.94 (s, 3 H, OMe), 3.92 (s, 3 H, OMe), 2.4-1.5 (a series of m, 6 H), 1.58 (q, Me); $^{13}$C NMR δ [from a 2:1 ratio of a mixture of 3D (c) and 3E (t)] 162.28 (Cl, t), 162.08 (C1,c), 161.33 (C4a, t), 161.23 (C4a, c), 160.09 (CHO, c), 159.98 (CHO, t), 159.65 (C3, c), 159.40 (C3, t), 151.19 (C4', c), 151.14 (C4', t), 148.88 (C3', c & t), 132.72 (C1', c), 131.79 (C1', t), 123.65 (C10a, c & t), 118.80 (C2', c), 118.73 (C2', t), 112.24 (C5', c), 112.12 (C5', t), 110.77 (C10, c & t), 107.84 (C6', c), 107.77 (C6', t), 97.87 (C9a, c), 97.45 (C9a, t), 95.85 (C4, c), 95.69 (C4, t), 83.98 (C5a, c), 82.67 (C5a, t), 76.23 (C6, c), 73.97 (C6, t), 56.83 (OMe, c & t), 55.74 (OMe, c & t), 30.91 (C9, c), 30.81 (C9, t), 28.82 (C7, c), 27.67 (C7, t), 22.65 (C8, c), 20.36 (C8, t), 18.46 (Me, c & t); MS.FAB, m/z 399 (M+1, 80%), 398 (M+), 352 (90%), 261, 165 (100%), 136.

Compound 3E (pure): $^1$H NMR δ 8.15 (s, 1 H, CHO), 7.40 (dd, J=8 Hz, 2 Hz, 1 H, C6'H, Ph), 7.27 (d, J=2 Hz, 1 H, C2'H), 6.90 (d, J=8 Hz, 1 H, C5'H), 6.32 (s, 1 H, C1OH), 6.29 (s, 1 H, C4H), 5.28 (s, 1 H, C6H), 3.94 (s, 3 H, OMe), 3.92 (s, 3 H, OMe), 2.4-1.5 (a series of m, 6 H), 1.62(q, Me); MS.FAB, m/z 399 (M+1, 80%), 398 M+).

Synthesis of 1H-6,7,8,9-tetrahydro-1-oxopyrano[4,3-b]quinoline (24) and 1H-7,8,9,10-tetrahydro-1-oxopyrano[4,3-c]isoquinoline (26) by Scheme 8.

A mixture of 0.190 g (1.52 mmol) of pyrone 20, 250 mg (2.28 mmol) of aldehyde 4A, and 35 mg (0.15 mmol) of (S)-(+)-10-cainphorsulfonic acid in 12 mL of toluene was heated at 85° C. for 3 days under argon atmosphere. The mixture was cooled to room temperature, filtered, and washed with 20 mL of ethyl acetate. The filtrate was diluted with 100 mL of methylene chloride, washed with 50 mL of water, and 50 mL of brine, dried (MgSO$_4$), concentrated, and column chromatographed on silica gel using ethyl acetate-:hexane (2:1) as eluant to give 13.3 mg (19% yield; based on unrecovered starting material) of 24, 33 mg (48% yield) of 26, and 150 mg (79% recovery) of pyrone 20. Pyrone 20 can be reused under similar reaction conditions to provide more materials of 24 and 26.

Compound 24: white solids, mp 71–72° C.; $^1$H NMR (CDCl$_3$) δ 8.15 (s, 1 H, CO H), 6.44 (s, 1 H, C4 H), 3.01 (t, J=7 Hz, 2 H, CH$_2$), 2.88 (t, J=7 Hz, 2 H, CH$_2$), 2.31 (s, 3 H, Me), 1.95 (m, 2 H, CH$_2$), 1.86 (m, 2 H, CH$_2$); $^{13}$C NMR (CDCl$_3$) δ 168 (s, Cl), 165.71 (s, C5 a), 157.69 (s, C4a), 152.22 (s, C3), 137.2 (d, C10), 132.34 (s, C10a), 114.0 (s, C9a), 105.48 (d, C4), 33.34 (t, CH$_2$), 28.69 (t, CH$_2$), 22.59 (t, CH$_2$), 22.32 (t, CH$_2$), 19.89 (q, Me); MS (FAB) 216 (M+1). The structure was unequivocally determined by a single-crystal X-ray analysis.

Compound 26: white solids, mp 73–74° C.; $^1$H NMR (CDCl$_3$) δ 8.50 (s, 1 H, C10 H), 6.43 (s, 1 H, C4 H), 3.35 (t, J=6 Hz, 2 H, CH$_2$), 2.82 (t, J=6 Hz, 2 H, CH$_2$), 2.29 (s, 3 H, Me), 1.90-1.80 (m, 4 H, CH$_2$); $^{13}$C NMR (CDCl$_3$) δ 162.5 (s, Cl), 157.4 (s), 156.4 (d, C6), 154.4 (s), 151.4 (s), 132.7 (s), 114.6 (s), 106.5 (d, C4), 28.6 (t, CH$_2$), 27.6 (t, CH2), 22.6 (t, CH$_2$), 21.7 (t, CH$_2$), 19.8 (q, Me); MS (FAB) 216 (M+1), 215, 188, 154, 136. The structure was unequivocally determined by a single-crystal X-ray analysis.

(5aS, 7S)-7-Isopropenyl-3-methyl-1H-5a,6,7,8,9-pentahydyro-1-oxopyrano[4,3-b][1]benzopyran (28)

From 1.000 g (7.93 mmol) of 5A and 1.191 g (7.93 mmol) of aldehyde (S)-27, 1.596 g (78% yield) of 28 was obtained after column chromatographic separation; yellow solids, mp 140–141° C. $[α]_D^{22}$=+31.9° (c 0.75, CHCl$_3$); $^1$H NMR δ 6.1 (s, 1 H, C10H), 5.72 (s, 1 H, C4 H), 5.1 (dd, J=11 Hz, 5 Hz, 1 H, C5a H), 4.75 (m, 1 H, =CH), 4.73 (m, 1 H, =CH), 2.48 (ddd, J=14 Hz, 2.4 Hz, 1 H), 2.22-2.02 (series of m, 3 H), 2.19 (s, 3 H, C4-Me), 1.88-1.72 (series of m, 2 H), 1.74 (s, 3 H, Me—C=), 1.31 (ddd, J=25 Hz, 12.8 Hz, 4 Hz, 1 H); $^{13}$C NMR δ 163.4 (s, C=O), 162.6 (s, C3), 161.7 (s, C4a), 147.9 (s, C10a), 132.3 (s, =C), 109.8 (d, C10), 109.6 (t, =CH$_2$), 99.9 (d, C4), 97.5 (s, C9a), 79.4 (s, C5a), 43.6 (d, C7), 40.0 (t), 32.5 (t), 32.1 (t), 20.9 (q, Me), 20.3 (q, Me); MS. FAB, m/z 259 (M+1; 70%), 258, 257, 215, 189, 139 (100%); Anal. Calc. for $C_{16}H_{18}O_3$: C, 74.40; H, 7.02. Found: C, 74.17; H, 7.33.

(5aS,7S)-7-Isopropenyl-3-(3-pyridyl)-1H-5a,6,7,8,9-pentahydro-1-oxopyrano[4,3-b][1]benzopvran (29).

From 0.200 g (1.06 mmol) of 5B and 0.160 g (1.06 mmol) of aldehyde (S)-27, 0.221 g (65% yield) of 29 was obtained after column chromatographic separation; yellow solids, mp 99–100° C. $[α]_D^{22}$=+100.6° (c 0.77, CH$_2$Cl$_2$); $^1$H NMR δ 8.98 (d, J=2 Hz, 1 H, C2' H, Pyr.), 8.65 (dd, J=4.8 Hz, 2 Hz, 1 H, C6'H), 8.07 (dt, J=8 Hz, 2 Hz, 1 H, C4'H), 7.38 (dd, J=8 Hz, 4.8 Hz, 1 H, C5'H), 6.44 (s, 1H, C10 H), 6.15 (s, 1 H, C4 H), 5.17 (dd, J=11.6 Hz, 5.2 Hz, 1 H, C5a H), 4.74 (In, 2 H, =CH$_2$), 2.52 (m, 1 H), 2.26-1.75 (a series of m, 5 H), 1.75 (s, 3 H, Me), 1.3 (m, 1 H); $^{13}$C NMR δ 162.5 (s, Cl), 161.3 (s, C4a), 156.6 (s, C3), 151.2 (d, C2'), 147.6 (d, C6'), 146.7 (s, C=), 133.9 (s, C3'), 132.7 (d, C4'), 127.4 (s, C10a), 123.7 (d, C5'), 109.9 (d, C10), 109.4 (t, =CH$_2$), 99.8 (s, C9a), 98.4 (d, C4), 79.6 (d, C5a), 43.4 (d, C7), 39.9 (t), 32.5 (t), 31.9 (t), 20.8 (q, Me); MS. FAB, m/z 322 (M+1, 100%), 278 (M+), 252, 202, 148, 106. Anal. Calc. for $C_{20}H_{19}NO_3$: C, 74.75; H, 5.96. Found: C, 74.48; H, 6.12.

(5aS,7S)-7-Isopropenyl-3-(3,4-dimethoxyphenyl)-1H-5a,6,7,8,9-pentahydro-1-oxopyrano[4,3b][1]benzopyran (30)

From 0.200 g (0.81 mmol) of 5C and 0.121 g (0.81 mmol) of aldehyde (S)-27, 0.193 g (63% yield) of 30 was obtained after colulmn chromatographic separation; yellow solids, mp 119–120° C. $[α]_D^{22}$=+90.4° (c 0.76, CHCl$_3$); $^1$H NMR δ 7.37 (dd, J=8.8 Hz, 2.4 Hz, 1 H, C6' H, Ph ring), 7.28 (d, J=2.4 Hz, 1 H, C2' H), 6.89 (d, J=8.8 Hz, 1 H, C5' H), 6.29 (s, 1 H, C10 H), 6.17 (s, 1 H, C4 H), 5.15 (dd, J=11 Hz, 5Hz, 1 H, C5a H), 4.75 (m, 2H, =CH$_2$), 3.94 (s, 3 H, OMe), 3.92 (s, 3 H, OMe), 2.52 (ddd, J=13 Hz, 6 Hz, 3.6 Hz, 1 H), 2.26-2.24 (a series of in, 3 H), 1.88-1.76 (m, 2 H), 1.75 (s, 3 H, Me), 1.34 (m, 1 H); $^{13}$C NMR δ 163.6 (s, Cl), 162.1 (s, C4a), 159.7 (s, C3), 151.6 (s, C4'), 149.4 (s, C3'), 148.0 (s, =C), 132.8 (s, Cl'), 124.3 (s, C10a), 119.1 (d, C2'), 111.3 (d, C5'), 109.9 (d, =CH$_2$), 109.9 (d, C10), 108.4 (d, C6'), 98.3 (s, C9a), 96.2 (d, C4), 79.5 (d, C5a), 56.3 (q, OMe), 56.2 (q, OMe), 43.6 (d, C7), 40.1 (t), 32.6 (t), 32.1 (t), 20.9 (q, Me); MS. FAB, m/z 381 (M+1, 100%), 380 (M+). Anal. Calc. for C$_{23}$H$_{24}$O$_5$: C, 72.61; H, 6.36. Found: C, 72.43; H, 6.17.

3-(Methoxycarbonylmethyl)-1H-5a,6,7,8,9-pentahydro-1-oxopyrano[4,3-b][1]benzopyran (31)

To a cold (−78° C.) solution of 0.4 g (1.83 mmol) of pyrone 1A in 10 mL of THF under argon was added a cold (0° C.) solution of LDA [freshly prepared from 0.31 mL (2.2 mmol) of diisopropylanine and 1.4 mL (2.2 mmol; 1.6 M in hexane) of n-BuLi in 10 mL of ether under argon at −10° C. for 1 h]. To the reaction solution, 0.32 mL (1.83 mmol) of HMPA (hexamethylphosphoramide) was added, the resulting solution was stirred at −78° C. for 3 h, and then 0.14 mL (1.83 mmol) of methyl chloroformate was added. After the solution was stirred at room temperature for 16 h, it was diluted with 20 mL of water, and extracted with 50 mL of methylene chloride. The methylene chloride extract was dried (MgSO$_4$), concentrated, and column chromatographed on silica gel using a gradient mixture of hexane and ether as eluant to give 0.215 g (72% yield; based on recovered starting material) of 31 and 0.165 g (41% recovery) of pyrone 1A. Compound 31: $^1$H NMR δ 6.1 (s, 1 H, C4 H), 6.06 (s, 1 H, C10 H), 5.06 (dd, J=11, 5 Hz, 1 H, C5a H), 3.81 (s, 2 H, CH$_2$), 3.80 (s, 3 H, OMe), 2.43 (m, 1 H), 1.98-1.74 (m, 5 H), 1.54-1.3 (m, 2 H); $^{13}$C NMR δ 165.2 (s, C=O), 162.3 (s, C=O), 161.4 (s, C3), 153.8 (s, C4a), 134.7 (s, C10a), 108.9 (d, C10), 102.6 (d, C4), 99.5 (s, C9a), 80.1 (s, C5a), 56.0 (q, OMe), 53.6 (t, CH$_2$), 35.3 (t), 33.3 (t), 27.0 (t), 24.5 (t).

3-(Carboxylmethyl)-1H-5a,6,7,8,9-pentahydro-1-oxopyrano[4,3-b][1]benzopyran (32)

A solution of 0.08 g (0.29 mmol) of ester 31 and 0.033 g (0.58 mmol) of KOH in 4 mL of THF-H$_2$O (1:3) was stirred at 40° C. for 30 h, cooled to room temperature, diluted with 30 mL of distilled water, and extracted with 40 mL of diethyl ether and then with 40 mL of methylene chloride. The combined extracts were washed with 30 mL of water, and with 30 mL of brine, dried (MgSO$_4$), concentrated to give 20.5 mg (26% recovery) of starting material 31. The combined aqueous layers were acidified with 1N HCl, and extracted three times with 50 mL-portion of methylene chloride. The combined extract was washed twice with water (40 mL each), with 40 mL of brine, dried (MgSO$_4$), concentrated to give 32.5 mg OH (58% yield; based on recovered starting material) of 32. $^1$H NMR δ 6.8 (broad s, 1 H, OH), 6.04 (s, 1 H, C10H), 5.96 (s, 1 H, C4 H), 5.07 (dd, J=11, 5 Hz, 1 H, C5a H), 3.51 (s, 2 H, CH$_2$), 2.42 (dd, J=14 Hz, 2 Hz, 1 H), 2.2-1.7 (m, 5H), 1.5-1.2 (m, 2 H).

1,8-Di-{3-[1H-5a,6,7,8,9-pentahydro-1-oxopyrano4,3-b][1]benzopyranyl]}-2,7-octanedione (33)

The reaction conditions are similar to those of the preparation of 31. From 0.40 g (1.83 mmol) of pyrone 1A, 2.2 mmol of LDA, 1.83 mmol of HMPA, and 0.13 mL (0.5 equiv.; 0.9 mmol) of adipoyl chloride in 10 mL of THF and 10 mL of ether gave 0.091 g (38% yield; based on recovered starting material) of 33 and 0.18 g (45% recovery) of starting material 1A after column chromatography. Compound 33: Mp. 161–162° C.; $^1$H NMR δ 6.39 (s, 2 H, =CH of enol of the side chain), 6.07 (s, 2 H, C10H), 5.64 (s, 2 H, C4 H), 5.04 (dd, J=11, 5 Hz, 2 H, C5a H), 2.6-1.3 (m, 24 H); $^{13}$C NMR δ 170.4 (s, C—O of enol), 162.9 (s, C=O), 161.6 (s, C3), 156.1 (d, =CH of enol), 154.7 (s, C4a), 134.6 (s, C10a), 109.3 an 109.2 (d, C10), 102.3 (d, C4), 99.4 (s, C9a), 79.8 (s, C5a), 35.3 (t), 34.6 (t), 33.3 (t), 28.9 (t), 27.0 (t), 24.6 (t), 22.8 (t).

(5aS,7S)-7-[2-(1-Hydroxypropyl)]-3-methyl-1H-5a,6,7,8,9-pentahydro-1-oxopyrano[4,3-b][1]benzopyran (34)

To a cold (−20° C.) solution of 0.10 g (0.39 mmol) of pyrone 28 in 3 mL of THF under argon was added a solution of 0.39 mL (0.39 mmol) of BH$_3$.THF (1.0M in THF). After the solution was stirred at −20° C. for 1 h, and −15° C. for 1 h, 2 mL of 1% aqueous NaOH and 1.5 mL of 30% H$_2$O$_2$ were added, and resulting solution was stirred at 25° C. for 3 h. The reaction mixture was diluted with 20 mL of distilled water, extracted three times with methylene chloride (40, 30, and 20 mL), and the combined extracts were washed with 30 mL of brine, dried (MgSO$_4$), concentrated, and column chromatographed on silica gel using a gradient mixture of hexane and ether as eluant to give 0.074 g (69% yield) of alcohols 34 as a 1:1 mixture of two diastereomers at C-12: $^1$H NMR δ 6.05 (s, 1 H, C10 H), 5.72 (s, 1 H, C4 H), 5.07 (m, 1 H, C5a H), 3.58 (ddd, J=11 Hz, 6 Hz, 3 Hz, 1 H, CHO), 3.54 (dd, J=11 Hz, 6 Hz, 1 H, CHO), 2.46 (d, J=12 Hz, 1 H), 2.19 (s, 3 H, Me), 2.18-1.3 (series of m, 7 H), 0.906 (d, J=6.8 Hz, 3 H, Me), 0.902 (d, J=6.8 Hz, 3 H, Me); $^{13}$C NMR δ 163.5 (s, C=O), 162.8 (s, C3), 161.6 (s, C4a), 133.0 (s, C10a), 109.1 (d, C10), 100.0 (d, C4), 97.5 (s, C9a), 79.8 and 79.7 (s, C5a; 2 isomers), 65.71 and 65.69 (t, CH$_2$O, 2 isomers), 40.1 and 39.4 (t), 37.4, 37.3, 37.0, 32.5, 32.4, 31.2, 28.6, 20.2 (q, Me), 13.3 and 13.2 (q, Me).

(5aS,7S)-7-[1-(Formyl)ethyl)]-3-methyl-1H-5a,6,7,8,9-pentahydro-1-oxopyrano[4,3-b][1]benzopyran (35)

A solution of 0.07 g (0.25 mmol) of alcohols 34 and 0.16 g (0.38 mmol) of 1,1,1-triacetoxy-1,1-dihydro-1,2-benziodoxol-3(1H)-one in 4 mL of methylene chloride was stirred at 25° C. under argon for 48 h. The mixture was filtered through Celite, washed with 50 mL of methylene chloride, and the filtrate was concentrated and column chromatographed on silica gel using a gradient mixture of hexane and ether as eluant to give 0.060 g (87% yield) of the desired aldehyde 35 as a mixture of two diastereomers; 1:1 (indicated by proton and carbon NMR spectra). $^1$H NMR δ 9.68 (d, J=0.8 Hz, 1 H, CHO), 6.09 (s, 1 H, C10 H), 5.71 (s, 1 H, C4 H), 5.1 (m, 1 H, C5a H), 2.47 (d, J=12 Hz, 1 H), 2.35 (m, 1 H, C12 H), 2.19 (s, 3 H, Me), 2.18-1.2 (series of m, 6 H), 1.10 (d, J=6.8 Hz, 3 H, Me); $^{13}$C NMR δ 204.14 and 204.1 (d, CHO), 163.29 and 163.27 (s, C=O), 162.5 (s, C3), 161.8 (s, C4a), 141.7 (s, C10a), 109.9 (d, C10), 99.8 (d, C4), 97.4 (s, C9a), 79.03 and 78.9 (s, C5a; 2 isomers), 50.79 and 50.73, 39.2 (t), 37.3, 36.3 and 36.2, 32.2 and 32.1, 31.2, 29.2, 20.2 (q, Me), 10.2 and 10.1 (q, Me).

(5aS,7S,10S)-7-[2-(1-Hydroxypropyl)]-10-hydroxy-3-(3,4-dimethoxyphenyl)-1H-5a,6,7,8,9,9a,10-heptahydro-1-oxopyrano[4,3-b][1]benzopyran (36)

To a cold (−20° C.) solution of 0.120 g (0.31 mmol) of pyrone 30 in 5 mL of THF under argon was added 1 mL (1 mol) of BH$_3$.THF (1 M in THF). After the solution was stirred at −20° C. for 30 min., 0° C. for 2 h, and 25° C. for 12, h, 2 mL of 1% NaOH and 2 mL of 30% H$_2$O$_2$ were added, and the resulting solution was stirred at room temperature for 3 h. The reaction solution was diluted with 20 mL of distilled water, extracted three times with methylene chloride (40, 30 and 20 mL), and the combined extract was washed with 40 mL of brine, dried (MgSO$_4$), concentrated, and column chromatographed on silica gel using hexane, ether, and ethyl acetate as eluants to give 0.021 g (16% yield) of diol 36 as a 1:1 mixture of two diastereomers at C11: $[\alpha]_D^{22}$=−7.4° (c=0.68, CHCl$_3$); $^1$H NMR δ 7.39 (dd, J=8.8 Hz, 2.4 Hz, 1 H, C6'H, Ph ring), 7.28 (d, J=2.4 Hz, 1 H, C2'H), 6.91 (d, J=8.8 Hz, 1 H, C5' H), 6.33 and 6.328 (two s, 1 H, C10 H; 2 isomers), 4.73 (dd, J=9 Hz, 3.3 Hz, 1 H, C5a H), 4.5 (m, 1 H, C10 H), 4.34 (broad s, 1 H, OH), 3.95 (s, 3 H, OMe), 3.93 (s, 3 H, OMe), 3.6 (m, 2H, CH$_2$O), 2.3-2.17 (m, 2 H), 1.85-1.3 (a series of m, 7 H), 0.92 and 0.91 (2 d, J=7 Hz, 3 H, Me; 2 diastereomers); $^{13}$C NMR δ 165.0 (s, C1), 164.5 (s, C4a), 151.8 (s, C3), 149.5 (s, C4'), 142 (s, C3'), 124.0 (s, C1'), 119.3 (s, C10a), 111.3 (d, C2'), 108.5 (d, C5'), 100.3 (d, C6'), 97.1 (d, C4), 66.1, 66.1, 56.4 (q, OMe), 56.3 (q, OMe), 39.7, 38.3, 38.2, 31.9, 24.6, 13.8 (q, Me).

(5aS,7S,10S)-7-[2-(1-Pentanoyloxypropyl)]-10-hydroxy-3-(3,4-dimethoxyphenyl)-1H-5a,6,7,8,9,9a, 10-heptahydro-1-oxopyrano[4,3-b][1]benzopyran (37)

A solution of 0.014 g (0.034 mmol) of alcohol 36, 4 mg (0.034 mmol) of valeryl chloride, and 0.03 mL (0.34 mmol) of pyridine in 1 mL of methylene chloride was stirred under argon at room temperature for 14 h. A solution of 7 mg of valeryl chloride in 0.2 mL of methylene chloride was added and the solution was stirred at 50° C. for 20 h. The progress of the reaction was monitored by TLC, and 0.015 g of veleryl chloride was added. After 10 min of stirring, the reaction was quenched by adding 20 mL of methylene chloride, washed with 15 mL of saturated aqueous NaHCO$_3$. The aqueous layer was extracted twice with methylene chloride (15 and 10 mL). The combined extracts were washed with 20 mL of brine, dried (MgSO$_4$), concentrated and column chromatographed on silica gel using a gradient mixture of hexane and ether as eluant to give 9 mg (53% yield) of ester 37 as a 1:1 mixture of 2 diastereomers at C11 (A & B); $^1$H NMR δ 7.44 (dd, J=8.4 Hz, 2 Hz, 1 H, C6' H, Ph ring; isomer A), 7.41 (dd, J=8.4 Hz, 2 Hz, 1 H, C6' H, Ph ring; isomer B), 7.32 (d, J=8.4 Hz, 1 H, C5' H), 6.39 and 6.27 (two s, 1 H, C10 H; 2 isomers), 5.84 (broad s, 1 H, OH of A), 5.75 (broad s, 1 H, OH of B), 4.45 (m, 1 H, C5a H), 4.32 (m, 1 H, C10 H), 4.06-3.99 (m, 2 H, CH$_2$O), 3.96 (s, 3 H, OMe of A), 3.95 (s, 3 H, OMe of B), 3.94 (s, 6 H, 2 OMe of A & B), 2.4-1.0 (a series of m, 15 H), 0.96-0.90 (t & d, 6 H, 2 Me; 2 diastereomers).

(5aS*,9aS*,10S*)-9a, 10-Epoxy-3-(3-pyridyl)-1H-5a.6,7,8,9,9a, 10-heptahydro-1-oxopyrano[4,3-b][1]benzopyran (38A) and (5aS*,9aR*,10R*)-9a,10-Dihydroxy-3-(3-pyridyl)-1H-5a,6,7,8.9,9a, 10-heptahydro-1-oxopyrano[4,3-b][1]benzopyran (38B)

To a cold (0° C.) solution of 90 mg (0.3 mmol) of pyrone 2A in 5 mL of methylene chloride under argon was added 0.3 mL (0.3 mmol) of a solution of HCl in ether (1 M). The solution was stirred for 10 min., warmed to room temperature and 0.102 g (0.32 mmol) of m-chloroperbenzoic acid (MCPBA; 55% pure) was added. After two hours of stirring, the mixture was neutralized with 1 M aqueous NaOH, and extracted with 20 mL of CH$_2$Cl$_2$. The extract was dried (MgSO$_4$), concentrated and column chromatographed on silica gel using ether as eluant to give 7 mg (7% yield) of epoxide 38A and 29 mg (30% yield) of dihydroxide 38B.

Compound 38A: $^1$H NMR δ 9.03 (s, 1 H, C2'H, Pyr.), 8.7 (s, 1 H, C6' H), 8.13 (dt, J=8 Hz, 2 Hz, 1 H, C4' H), 7.42 (dd, J=8 Hz, 4.9 Hz, 1 H, C5' H), 6.51 (s, 1 H, C4 H), 5.11 (s, 1 H, C10 H), 4.52 (dd, J=12 Hz, 5 Hz, 1 H, C5a H), 2.43 (m, 1 H), 2.15-1.4 (a series of m, 7 H).

Compound 38B: $^1$H NMR δ 9.03 (s, 1 H, C2' H, Pyr.), 8.72 (s, 1 H, C6' H), 8.14 (dt, J=8 Hz, 2 Hz, 1 H, C4' H), 7.42 (dd, J=8 Hz, 4.9 Hz, 1 H, C5' H), 6.51 (s, 1 H, C4 H), 5.04 (s, 1 H, C10 H), 4.81 (s, 1 H, C5a H), 2.3-1.2 (a series of m, 8 H). MS (FAB) m/z: 316 (M+1).

(5R,6S)-2,6-dimethyl-6-(cis-3-iodo-2-propenyl)-5-isopropenyl-2-cyclohexen-1-one (41)

To a cold (−40° C.) solution of 46 mL (21 mmol) of LDA (prepared as mentioned above from 2.9 mL of diisopropylamine and 13 mL of n-BuLi in 30 mL of THF) under argon was added a solution of 1.69 g (10.3 mmol) of (5R,6S)-2, 6-dimethyl-5-isopropenyl-2-cyclohexen-1-one in 30 mL of ether was added via cannula, an the resulting solution was stirred at 0° C. for 45 min. To it, 1.8 mL (10 mmol) of HMPA was added, stirred at the same temperature for 4 hours, and a solution of 5.68 g (22 mmol) of (cis-3-iodo-2-propenyl) methanesulfonate (40)$^2$ in 30 mL of ether was added. After stirring at room temperature for 12 hours, the reaction mixture was poured into an aqueous solution of NaHCO$_3$, extracted three times with ether, and the combined extracts were washed with brine, dried (MgSO$_4$), and concentrated. The residue was column chromatographed on silica gel using a hexane:methylene chloride (3:2) as eluant to give 2.48 g (73% yield) of 41 and 0.237 g (14% recovery) of the starting material.

Compound 41: $[\alpha]_D^{22}$=−31.9° (c=1.5, CHCl$_3$); $^1$H NMR δ 6.63 (m, 1 H, C3 H), 6.3 (dt, J=8 Hz, 1.6 Hz, 1 H, =CH—I), 6.12 (dt, J=8 Hz, 6.4 Hz, 1 H, =CH), 4.83 (s, 1 H, =CH$_2$), 4.74 (s, 1 H, =CH$_2$), 2.7-2.3 (a series of m, 5 H), 1.79 (s, 3 H, =C-Me), 1.65 (s, 3 H, =C—Me), 1.09 (s, 3 H, Me); $^{13}$C NMR δ 203.4 (s, C1), 145.8 (s, =C), 142.4 (d, =CH), 137.7 (d, =CH), 134.2 (s, =C), 114.8 (t, =CH$_2$), 84.9 (d, CH-I), 50.5 (d, C5), 48.0 (s, C6), 42.8 (t), 29.2 (t), 22.5 (q, Me), 19.3 (q, Me), 16.6 (q, Me).

(4aS,5R,8aS)-Methyl-(1 H)-1-Oxo-4,4a,5,8,8a-pentahydro-2,5,8a-trimethylnaphthalene-5-acetate (42) and (4aS,5S, 8aS)-Methyl-(1H)-1-Oxo-4,4a5,8,8a-pentahydro-2,5,8a-trimethylnaphthalene-5-acetate (47)

A mixture of 0.387 g (1.72 mmol) of Pd(OAc)$_2$ and 0.904 g (3.44 mmol of Ph$_3$P in 10 mL of DMF under argon was stirred at room temperature for one hour. To it, a solution of 0.569 g (1.72 mmol) of iodide 41 in 10 mL of DMF was added via cannula, and the mixture was stirred at 32° C. for 30 min. After 10 mL of MeOH was added, the mixture was maintained under 1 atmosphere of CO (a CO balloon was used), and 0.476 g (1.72 mmol) of Ag$_2$CO$_3$ was added. After stirring at 32° C. for 15 hours, the mixture was cooled to room temperature, filtered, washed the solids with methylene chloride, and the filtrate was concentrated. The residue was dissolved in either and washed with brined, dried (MsSO$_4$), concentrated, and column chromatographed on silica gel using a hexane:ether (10:1) as eluant to give 0.332 g (73% yield) of a mixture of 2.2:1 of 42 and 47.

Pure compound 47: $^1$H NMR δ 6.77 (m, 1 H, C3 H), 5.68 (ddd, J=10 Hz, 5.6 Hz, 2 Hz, 1 H, C7 H), 5.56 (dd, J=10 Hz, 2 Hz, 1 H, C6 H), 3.67 (s, 3 H, OMe), 2.62 (d, J=13 Hz, 1 H, CH$_2$CO$_2$), 2.36 (m, 1 H), 2.31 (d, J=13 Hz, 1 H, CH$_2$CO$_2$), 2.28 (m, 2 H), 2.14 (d, J=18 Hz, 1 H, C8 H), 2.02 (dd, J=11 Hz, 5 Hz, 1 H, C4a H), 1.77 (s, 3H, =C—Me), 1.21 (s, 3 H, C5—Me), 1.10 (s, 3 H, C8a—Me).

Compound 42 [from a mixture of 42 (major) and 47 (minor)]: $^1$H NMR δ 6.77 (m, 1 H, C3 H), 5.68 (m, 1 H, C7 H), 5.53 (dd, J=10 Hz, 2 Hz, 1 H, C6 H), 3.62 (s, 3 H, OMe), 2.62 (d, J=13 Hz, 1 H, CH$_2$CO$_2$), 238-2.26 (a series of m, 4 H), 2.12 (d, J=18 Hz, 1 H, C8 H), 2.01 (dd, J=11 Hz, 5 Hz, 1 H, C4a H), 1.77 (s, 3 H, =C—Me), 1.12 (s, 3 H, C5—Me), 1.07 (s, 3 H, C8a—Me); $^{13}$C NMR δ [a mixture of 42 (designated as A) and 47 (designated as B) 204.5 (s, C1, A), 204.47 (s, C1, B), 172.5 (s, C2, A), 171.8 (s, C2, B), 143.7 (d), 134.8 (s), 133.8 (s), 133.7 (s), 133.4 (d, A), 132.5 (d, B), 123.7 (d, A), 123.5 (d, B), 51.5, 51.45, 48.0, 47.2, 46.9, 44.3, 44.1, 43.6, 41.7, 38.1, 36.7, 33.7, 33.1, 28.4, 24.3, 23.9, 23.8, 18.0, 17.99, 16.43 (q, A), 16.41 (q, B).

(4aS,8aS)-(1H)-1-Oxo-4,4a,5,8,8a-pentahydro-2,5,8a-trimethylnaphthalene-5-acetic acid (43); a mixture of 2.2:1 of 5R and 5S)

A solution of 0.127 g (0.48 mmol) of methyl esters 42 and 47 (2.2: 1) and 90 mg (1.6 mmol) of KOH in 0.5 mL of water and 2 mL of MeOH was stirred at room temperature for 22 hours. The solution was acidified with 1N aqueous HCl, extrated three times with $CH_2Cl_2$, and the combined extract was washed with brine, dried ($MgSO_4$), concentrated, and column chromatographed on silica gel using hexane:ether (1:1) as eluant to give 0.116 g (96% yield) of the acids 43 as a mixture of 2 isomers at C5.

Compounds 43: $^1$H NMR δ 6.79 (m, 1 H, C3 H), 5.74-5.6 (m, 1 H, C7 H), 5.57 (dd, J=10 Hz, 2 Hz, 1 H, C6 H), 2.64 (d, J=13 Hz, 1 H, $CH_2CO_2$), 2.42-2.2 (a series of m, 4 H), 2.16 (d, J=18 Hz, 1 H, C8 H), 2.05 (dd, J=11 Hz, 5 Hz, 1 H, C4a H), 1.77 (s, 3 H, =C—Me), 1.24 (s, 3 H, C5—Me of minor isomer), 1.15 (s, 3 H, C5—Me of major isomer), 1.11 (s, 3 H, C8a—Me of minor isomer), 1.08 (s, 3 H, C8a—Me of major isomer); $^{13}$C NMR δ [a mixture of the α-isomer (major) (designated as A) and β-isomer (minor) (designated as B) 204.75 (s, C1, A), 204.55 (s, C1, B), 178.4 (s, C2, B), 177.5 (s, C2, A), 143.9 (d, A), 143.84 (d, B), 133.9 (B), 133.8 (A), 133.0 (A), 132.2 (B), 124.2 (A), 123.9 (B), 48.1, 46.8, 44.4, 44.2, 43.6, 41.8, 38.2, 36.6, 33.8, 33.1, 28.4, 24.4, 24.0, 23.9, 18.1, 16.51 (q, A), 16.49 (q, B).

(1S,4aS,8aS)-(1H)-1-[2-(1,3-dithianyl)]-1-hydroxy-4,4a,5,8,8a-pentahydro-2,5,8a-trimethylnaphthalene-5-acetic acid (44)

To a cold (0° C.) solution of 0.116 g of 1,3-dithiane (9) in 4 mL of THF under argon was added 0.6 mL (0.97 mmol) of n-BuLi (1.6M in hexane). After the solution was stirred at −10° C. for two hours, a solution of 0.080 g (0.32 mmol) of enone 43 in 1 mL of THF was added via cannula. The solution was stirred at room temperature for 16 hours, diluted with 20 mL of water and 5 mL of 6N HCl, and extracted three times with 40 mL portion of methylene chloride. The combined extract was washed with 30 mL of water, and 30 mL of brined, dried ($MgSO_4$), concentrated and column chromatographed on silica gel using a gradient mixture of hexane and diethyl ether as eluant to give a good yield of 44. $^1$H NMR ($CDCl_3$) δ 5.75 (m, 1 H, C7 H), 5.6 (broad s, 1 H, C3 H), 5.58 (dd, J=10 Hz, 2 Hz, 1 H, C6 H), 4.57 (s, 1 H, CH—S), 2.9-2.6 (m, 4 H, $CH_2S$), 2.41 (d, J=14 Hz, 1 H, $CH_2CO_2H$), 2.25 (d, J=14 Hz, 1 H, $CH_2CO_2H$), 2.3-1.2 (a series of m, 7 H), 1.83 (s, 3 H, =$CCH_3$), 1.08 (s, 3 H, Me), 1.01 (s, 3 H, Me).

Biological Studies

Acetylcholinesterase Assay and Inhibition Kinetics: Tricyclic pyrones of this invention were tested for inhibition of AChE. The activities of electric eel acetylcholinesterase (EC 3.1.1.7, Sigma Chemical Co., St. Louis, Mo.), and fetal bovine serum acetylcholinesterase (Ralston, J. S. et al. (1985), "Acetylcholinesterase from Fetal Bovine Serum," J. Biol. Chem. 260:4312–4318) were determined colorimetrically by the method of Ellman (Ellman, G. L. et al. (1961), "A new and rapid colorimetric determination of acetylcholinesterase activity," Biochem. Pharmacol. 7:88–95) as described by Main et al. (Main, A. R. et al. (1974), "Purification of cholinesterase from horse serum," Biochem. J. (1974) 143:733–744). Reactions were carried out at 30° C. in 0.1M sodium phosphate buffer at pH 8.0 in the presence of $10^{-3}$ acetylthiocholine and $3.3 \times 10^{-4}$ M 3-carboxy-4-nitrophenyl disulfide. Aliquots of incubating mixtures containing enzyme alone, or enzyme in the presence of each carbamate, were withdrawn at selected time intervals and assayed for enzyme activity in order to obtain kinetic data. From the kinetic data, inhibition and bimolecular rate constants were calculated by the equation:

$$\frac{1}{k_{app}} = \frac{1}{k_3} + \frac{K_T}{k_3} \cdot \frac{1}{[I]}$$

in which $k_{app}$ is the pseudo-first-order rate constant. The bimolecular rate constant ($k_3'$) is equal to $k_3/K_T$. All the tricyclic pyrones are inactive against butyrylcholinesterase (BChE). BChE does not affect the formation of Aβ. The AChE inhibitory data of various tricyclic pyrones are summarized in Table 3. The inhibition of Ki of the tricyclic pyrones are in the μM range; while tacrine, an art-known AChE inhibitor, is in the nM range.

TABLE 3

The AChE inhibition constant Ki of various tricyclic pyrones

| Tricyclic Pyrones | Ki(μM) ± std. error |
| --- | --- |
| 1A | 7 ± 1.2 |
| 1B | 20 ± 5.8 |
| 1D | 5 ± 1.7 |
| 2B | 8 ± 2.3 |
| 2D | 26 ± 2.3 |
| 3A | 23 ± 3.5 |
| 3B | 4 ± 0.6 |
| 3D | 15 ± 5.8 |
| tacrine | 1 nM |

Inhibition of liver and intestinal microsomal ACAT activity: Several synthesized tricyclic pyrones were tested for their inhibition of liver and intestinal microsomal ACAT along with pyripyropene A and CP-113,818 (as control) (Marzetta, C. A. et al. (1994), "Pharmacological properties of a novel ACAT inhibitor (CP-113,818) in cholesterol-fed rats, hamsters, rabbits, and monkeys," J. Lipid Res. 35:1829–1838). Microsomes were prepared from liver and intestinal mucosal scrapings by sequential centrifugation and in vitro ACAT activity assays were done according to the method of Billheimer (Billheimer, J. T. (1985), "Cholesterol acyltransferase," In Methods in Enzymology 111:286–293). Briefly, 100 μg microsomal protein, 22 μg BSA, and 52 nmol cholesterol and the synthesized drug in 5 μL DMSO were preincubated for 30 minutes at 37° C. in a phosphate buffer (200 μL total volume). After 30 minutes, 1 nmol [$^{14}$C]oleoyl-CoA was added as substrate and incubated for an additional 20 minutes. The reaction was stopped with the addition of 1 mL ethanol and lipids were extracted with hexane. Cholesteryl [$^{14}$C]oleate formation was quantified by thin-layer chromatography and data are expressed as percent inhibition of ACAT activity (pmol/μg protein per minute) compared to a control sample incubated with no drug. All samples were run in duplicate. Using the literature $IC_{50}$ value of pyripyropene of 58 nM as standard, it was found that $IC_{50}$ values for 2A, 3A, and 1D are 50 μM, 63 μM, and 52 μM, respectively.

TABLE 4

The Inhibition of ACAT by tricyclic pyrones and CP-113,818.

| Compound | Concentration | % Inhibition |
| --- | --- | --- |
| 24 | 100 μM | 3.3 |
|  | 50 μM | 1.9 |
| 26 | 100 μM | 13.7 |

TABLE 4-continued

The Inhibition of ACAT by tricyclic pyrones and CP-113,818.

| Compound | Concentration | % Inhibition |
|---|---|---|
| | 50 µM | 2.7 |
| 38B | 100 µM | 11.4 |
| | 50 µM | 9.7 |
| 37 | 100 µM | 52.4 |
| | 50 µM | 36.8 |
| 30 | 100 µM | 21.9 |
| | 50 µM | 13.3 |
| 29 | 100 µM | 39 |
| | 50 µM | 21 |
| 28 | 100 µM | 30 |
| | 50 µM | 17 |
| 32 | 100 µM | 7.9 |
| | 50 µM | 10.3 |
| 33 | 100 µM | 76 |
| | 50 µM | 57 |
| CP-113,818 | 44 nM | 42.5 |

Inhibition of DNA Synthesis: Tricyclic pyrone derivatives of this invention were tested for their ability to prevent L1210 leukemic cells from synthesizing DNA and growing in vitro. At 50 µM, a pyripyropene analog, 22, has no effect, whereas four pentahydro-3-aryl-1-oxopyrano[4,3-b][1]benzopyrans all inhibit DNA synthesis by 79–91% and tumor cell growth by 93–100%. These inhibitory effects are concentration-dependent with $IC_{50}$ around 8.5 µM for DNA synthesis at 2 h and 1.1 µM for tumor cell growth at 4 days. The aryl groups of the antitumor agents tested are either 3,4-dimethoxyphenyl or 3-pyridyl. Introduction of a methyl group at C5a and a formyloxy or hydroxy group at C6 does not alter the antitumor effects of the 3,4-dimethoxyphenyl benzopyrans but reduces those of the 3-pyridyl benzopyrans, which, at 50 µM inhibit DNA synthesis by only 32–49% and fail to alter tumor cell growth. The 4-hydroxy-6-(3-pyridyl)-2-pyrone (5B) has no effect and the tricyclic pyrones lacking aryl groups (e.g., 1A–1E) have less inhibitory effect on DNA synthesis, suggesting that a greater conjugation is required for the antitumor activity. The tricyclic pyrones also inhibit to a similar degree other macromolecule synthesis, e.g., RNA and protein synthesis. The 3,4-dimethoxyphenyl substituted tricyclic pyrone 3A being a more potent inhibitor of macromolecule synthesis than the 3-pyridyl substituted tricyclic pyrone 2A. Additionally, the tricyclic pyrones inhibit the growth of EMT6 mammary carcinoma cells and MCF-7 human breast cancer cells. However, in both these systems, tricyclic pyrone 2A has a greater inhibitory effect than tricyclic pyrone 3A. This lack of correlation between the ability of tricyclic pyrones to inhibit tumor cell growth and macromolecular synthesis suggests that other macromolecular targets may be involved in the antitumor action of these drugs.

Inhibition of Tubulin Polymerization

Tricyclic pyrone derivatives of this invention were tested for their ability to prevent tubulin polymerization. It was found that 2A completely inhibits tubulin polymerization and, therefore, works as a novel microtubule (MT) de-stabilizing drug. The ability of 2A to disrupt MT dynamics suggests that the anticancer activity of tricyclic pyrones may be cell cycle-specific. These anticancer drugs are therefore useful for arresting mammalian cells in mitosis. Tricyclic pyrones that can selectively disrupt MT dynamics and block the M-phase of the cell cycle have great therapeutic value.

Tubulin is a labile protein, which is unstable below 80 mM PIPES, should not be exposed to pH values less than 6.8 or greater than 7.0, and will not polymerize in the presence of $Ca^{2+}$. GTP and $Mg^{2+}$ are necessary for tubulin nativity and glycerol stabilizes tubulin and lowers the initial concentration required to initiate polymerization.

The ability of 2A to alter the polymerization of pure tubulin in a cell-free system in vitro was analyzed using the assay kit purchased from Cytoskeleton (Denver, Co.). The polymerization reaction contained, in a final volume of 200 µl, tubulin protein from bovine brain (2.5 mg/ml), 80 mM PIPES buffer, pH 6.8, 1 mM $MgCl_2$, 1 mM EGTA, 1 mM GTP and 10% glycerol. Compound 2A was added in 2 µl of DMSO:tubulin buffer (40:60) to obtain a final concentration of 25 µM. This vehicle did not affect the rate of tubulin polymerization in drug-untreated control reactions. Samples were incubated at 35° C. in quartz microcells and the rate of tubulin polymerization was followed over 20 min by measuring the increased absorbance of the solution at OD340 nm, using a Shimadzu UV-160 spectrophotometer equipped with dual-beam optics and a thermostatically-controlled cell holder.

Figure 14:
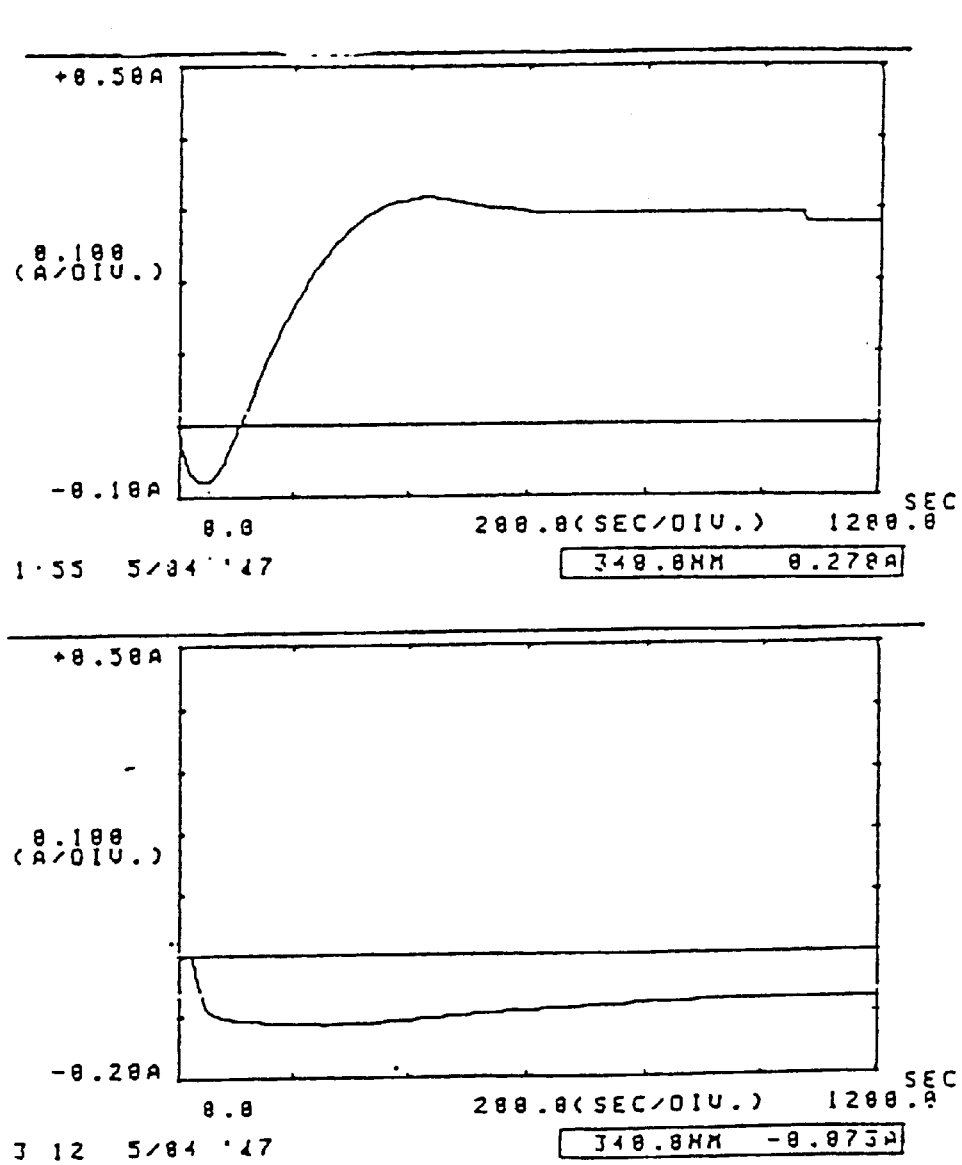
FIG. 14 shows the ability of the new tricyclic pyrone analog 2A to completely inhibit polymerization of pure tubulin in a cell-free system in vitro. In a final volume of 200 μl, a solution of 2.5 mg/ml tubulin protein from bovine brain, 80 mM PIPES buffer, pH 6.8, 1 mM $MgCl_2$, 1 mM EGTA, 1 mM GTP, and 10% glycerol was incubated at 35° C. for 20 minutes in the presence or absence (control) of 25 $\mu$M of compound 2A. The absorbance of the solution at $OD_{340}$ nm was measured to determine the rate of tubulin polymerization.

FIGS. 14A–B show the three typical phases of MT polymerization normally occurring in vehicle-treated control samples. The lag phase I is necessary to create nucleation sites (small tubulin oligomers) from which longer MT polymers can form. The growth phase II reflects the rapid increase in the ratio of MT assembly: disassembly occurring under those experimental conditions. And the steady phase III is established when the residual concentration of free tubulin heterodimer becomes equal to the critical concentration required to initiate polymerization. One unit of tubulin is defined as 5 mg of purified protein. When tubulin at a concentration of 1 unit (5 mg)/ml is incubated at 35° C. for 30 min. in the presence of 80 mM PIPES, pH 6.8, 1 mM $MgCl_2$, 1 mM EGTA, 1 mM GTP and 10% glycerol, the $OD_{340nm}$ increases from 0.0 to 1.0, which indicates that about 97% of tubulin has polymerized to form a total MT polymer mass of 4.8 mg/ml. An increase in OD of 0.2 is roughly equal to a MT polymer mass of 1 mg/ml. The kinetics of MT polymerization in FIG. 14A, therefore, appear consistent with the initial concentration of 2.5 mg tubulin/ml used in our control assay. In contrast, no significant MT polymerization can be detected in the presence of 25 µM of 2A in FIG. 14B.

Materials and Methods

All solutions of tricyclic pyrone analogs were dissolved and diluted in 100% ethanol (ETOH), whereas CPT (Sigma Chemical Co., St. Louis, Mo.) solutions were prepared in 100% dimethyl sulfoxide (DMSO). Murine L1210 lymphoblastic leukemia cells, obtained from the American Type Culture Collection (Rockville, Md.), were maintained in continuous exponential growth by twice-a-week passage in RPMI 1640 medium supplemented with 7.5% fortified bovine calf serum (HyClone Laboratories, Inc., Logan, Utah). The cultures were incubated at 37° C. in a humidified atmosphere containing 5% $CO_2$. All drugs were supplemented to the culture medium in 1- or 2 µl aliquots. The concentration of vehicle in the final incubation volume never exceeded 0.2–0.4%. Such low concentrations of EtOH or DMSO do not affect the rates of DNA synthesis and growth in L1210 cells. Control cells incubated in the absence of drugs were similarly treated with vehicle only and, in every experiment, all incubates received the same volume of solvent.

For DNA synthesis, L1210 cells were resuspended in fresh serum-free RPMI 1640 medium at a density of about $2.5 \times 10^6$ cells/0.5 ml. The cells were incubated at 37° C. for 90 min in the presence or absence of drugs and then pulse-labeled for an additional 30 min with 1 μCi of [methyl-$^3$H]thymidine (51 Ci/mmol; Amersham Corp., Arlington Heights, Ill.). The incubations were terminated by the addition of 0.5 ml of 10% trichloroacetic acid (TCA). After holding on ice for 15 min, the acid-insoluble material was recovered over Whatman GF/A glass microfibre filters and washed thrice with 2 ml of 5% TCA and twice with 2 ml of 100% EtOH. After drying the filters, the radioactivity bound to the acid-precipitable material was determined by liquid scintillation counting in 10 ml of Bio-Safe NA (Research Products International Corp., Mount Prospect, Ill.).

For tumor cell growth, L1210 cells were resuspended in fresh serum-containing RPMI 1640 medium, plated at an initial density of $1 \times 10^4$ cells/0.5 ml, and incubated in 48-well Costar cell culture plates (Costar, Cambridge, Mass.). Cells were grown for 4 days in the presence or absence of drugs and their density was monitored every 24 h using a Coulter counter (Coulter Electronics, Ltd., Luton Beds, England). Data of all in vitro experiments were analyzed using Student's t-test with the level of significance set at $P<0.05$.

Figure 2:
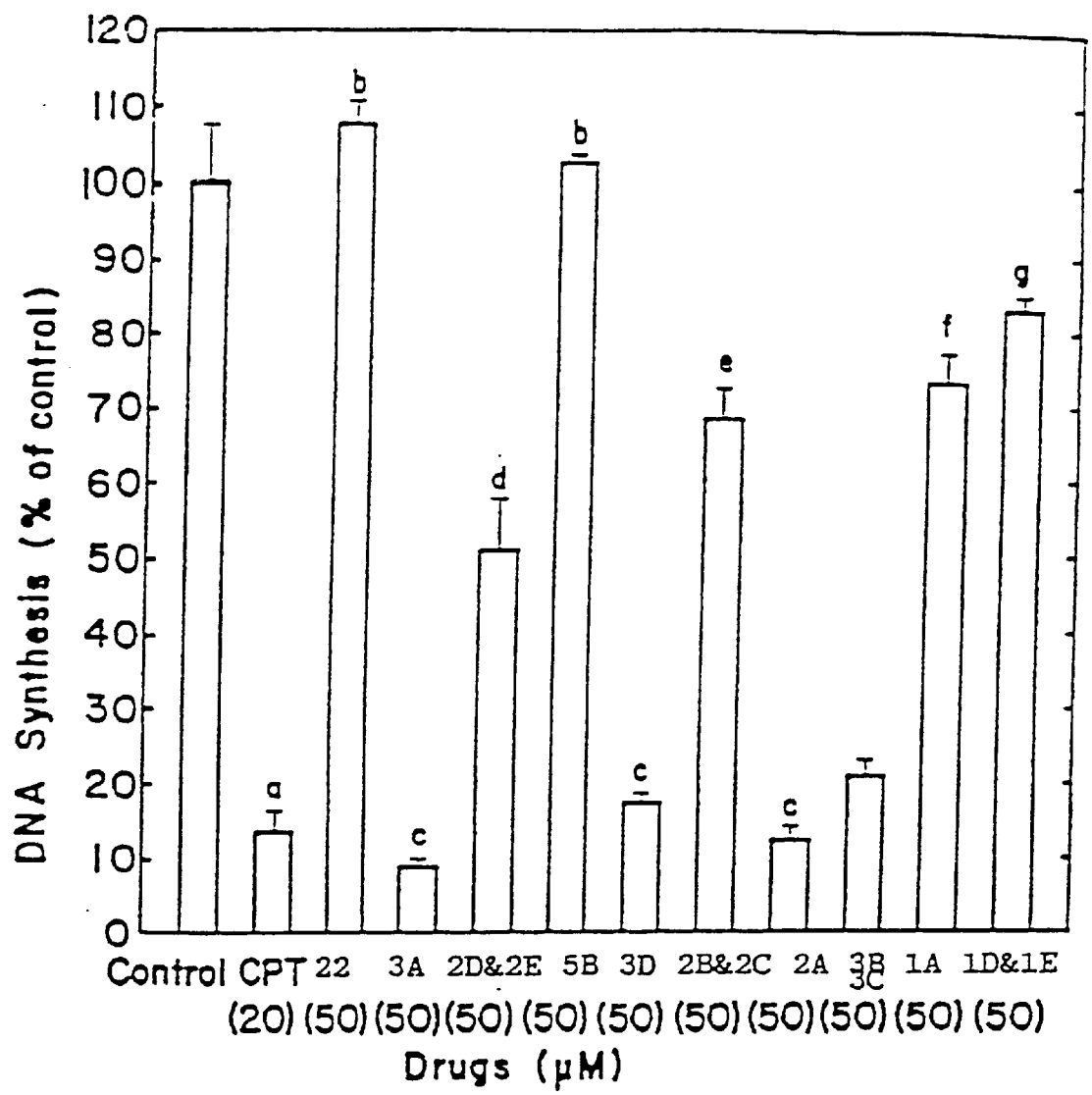
FIG. 2 shows a comparison of the effects of 10 new tricyclic pyrone derivatives and CPT on DNA synthesis in L1210 cells in vitro. The protocol of the experiment was identical to that of FIG. 1, except that the cell density was 2.64×10$^6$ cells/0.5 ml. DNA synthesis in vehicle-treated control cells was 60,998±4,636 cpm (100±8%). The blank value (1,297±182 cpm) for cells pulse-labeled for 0 minutes with 1 μCi of $^3$H-thymidine has been subtracted from the results. Bars: means±SD (n=3). $^a$P<0.025, significantly smaller than 3B & 3C; $^b$not significantly different from control; $^c$not different from CPT (20 μM); $^d$P<0.025, smaller than 2B & 2C; $^e$not different from 1A; $^f$P<0.025, smaller than 1D & 1E; $^g$P<0.025, smaller than control.

The known anticancer drug CPT inhibits the incorporation of $^1$H-thymidine into DNA in a concentration-dependent manner (FIG. 1). When tested at 25 μM, the new agent 3A inhibits DNA synthesis in L1210 cells by 62% but 22, 2D & 2E and 5B have no significant effects (FIG. 1). However, 2D & 2E can inhibit DNA synthesis by 49% at 50 μM (FIG. 2). In contrast, 22 and 5B remain ineffective even at this higher concentration (FIG. 2). Overall, four of the newly synthesized compounds can prevent leukemic cells from synthesizing DNA. Indeed, 50 μM 3A, 3D & 3E, 2A and 3B & 3C inhibit DNA synthesis in L1210 cells by 79–91%, an effect comparable to that of 20 μM CPT (FIG. 2). Besides 2D & 2E, which is a moderate inhibitor, the three remaining new compounds tested have very weak inhibitory in effects on DNA synthesis in L1210 cells. At 50 μM, 2B & 2C, 1A, and 1D & 1E inhibit this DNA response by only 17–32% (FIG. 2).

Figure 3:
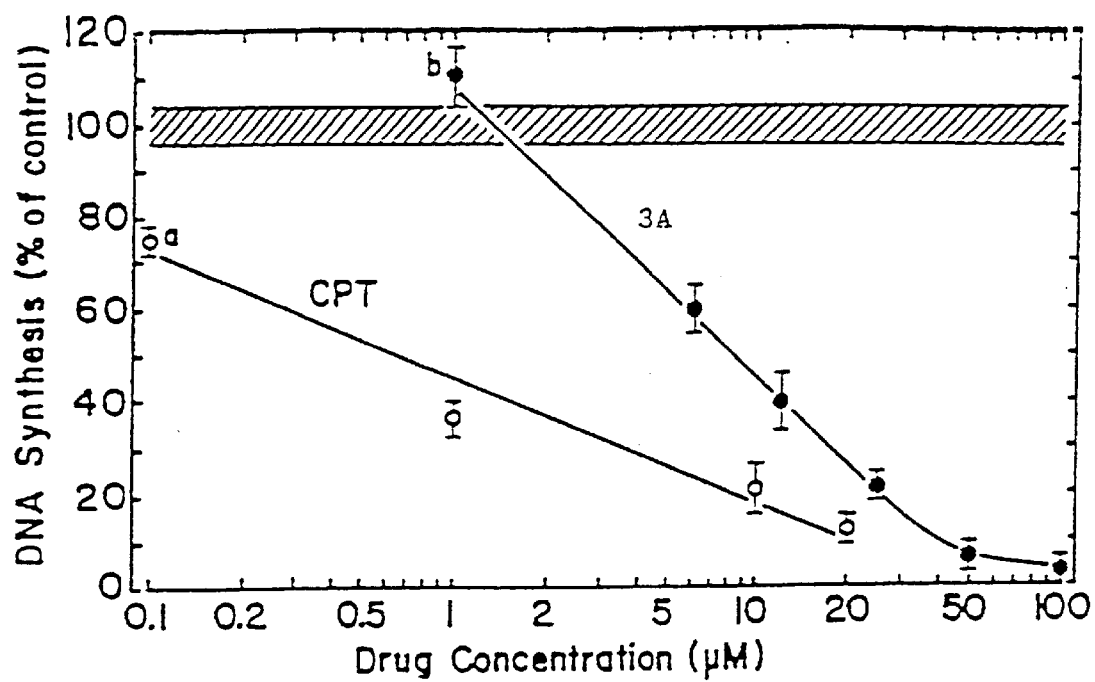
FIG. 3 illustrates the concentration-dependent inhibition of DNA synthesis by the new tricyclic pyrone analog 3A (●) and CPT (○) in L1210 cells in vitro. The protocol of the experiment was identical to that of FIG. 1, except that the cell density was 2.07×10$^6$ cells/0.5 ml. DNA synthesis in vehicle-treated control cells was 29,813±1,282 cpm (100±4%; striped area). The blank value (954±238 cpm) for cells pulse-labeled for 0 minutes with 1 μCi of $^3$H-thymidine has been subtracted from the results. The concentrations of drugs are plotted on a logarithmic scale. Bars: means±SD (n=3). $^a$P<0.005, significantly smaller than control; $^b$not significantly different from control.
Figure 4:
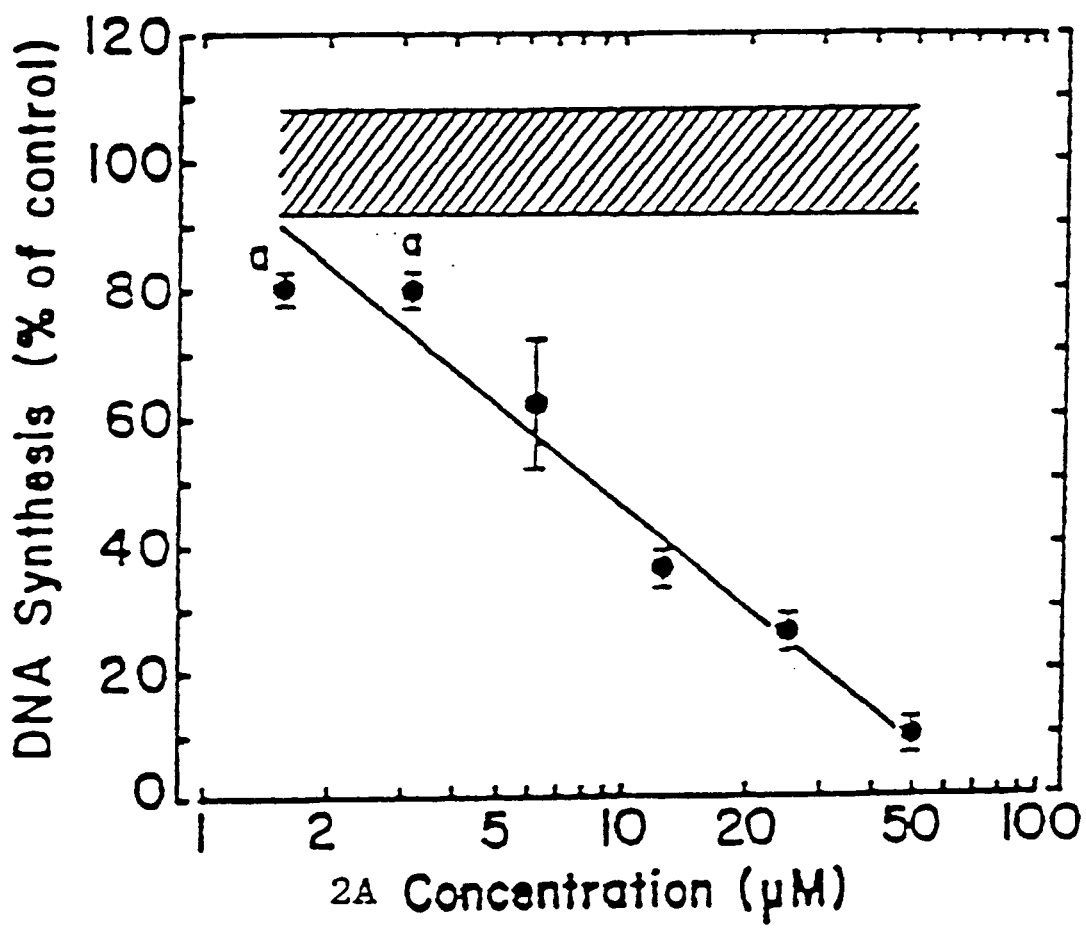
FIG. 4 shows the concentration-dependent inhibition of DNA synthesis by the new tricyclic pyrone analog 2A (●) in L1210 cells in vitro. The protocol of the experiment was identical to that of FIG. 1, except that the cell density was 2.83×10$^6$ cells/0.5 ml. DNA synthesis in vehicle-treated control cells was 94,547±7,564 cpm (100±8%; striped area). The blank value (1,580±92 cpm) for cells pulse-labeled for 0 minutes with 1 μCi of $^3$H-thymidine has been subtracted from the results. The concentrations of drugs are plotted on a logarithmic scale. Bars: means±SD (n=3). $^a$P<0.025, significantly smaller than control.

Although less potent than CPT, 3A and 2A both inhibit the DNA response of L1210 cells in the same concentration-dependent manner (FIGS. 3 and 4). In this L1210 system in vitro, the concentration of 3A or 2A that inhibits DNA synthesis by 50% ($IC_{50}$) is about 8.5 μM, whereas that of CPT is about 0.65 μM (FIGS. 3 and 4).

Figure 5:
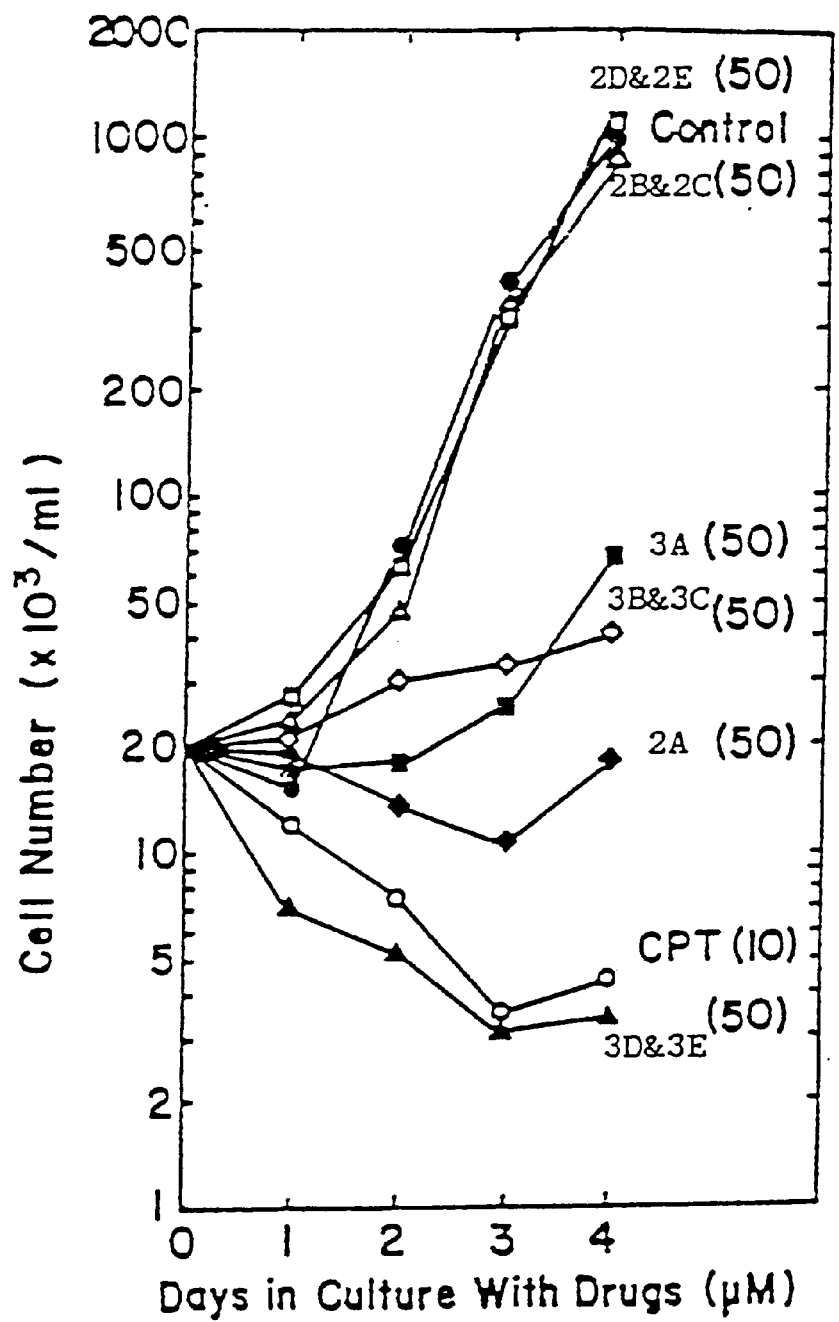
FIG. 5 shows a comparison of the effects of six new tricyclic pyrone analogs and CPT on the growth of L1210 cells in vitro. Cells were plated at an initial density of 1×10$^4$ cells/0.5 ml/well in RPMI 1640 medium, containing 7.5% fortified bovine calf serum, and grown at 37° C. for 4 days in a humidified incubator in 5% $CO_2$ in air. Cells were incubated in the presence or absence (●, control) of 50 μM 3A (■), 2D & 2E (□), 3D & 3E (▲), 2B & 2C (Δ) 2A (◆), 3B & 3C (◇), or 10 μM CPT (○) and their density was monitored in triplicate every 24 h using a Coulter counter. Cells numbers are plotted on a logarithmic scale.
Figure 6:
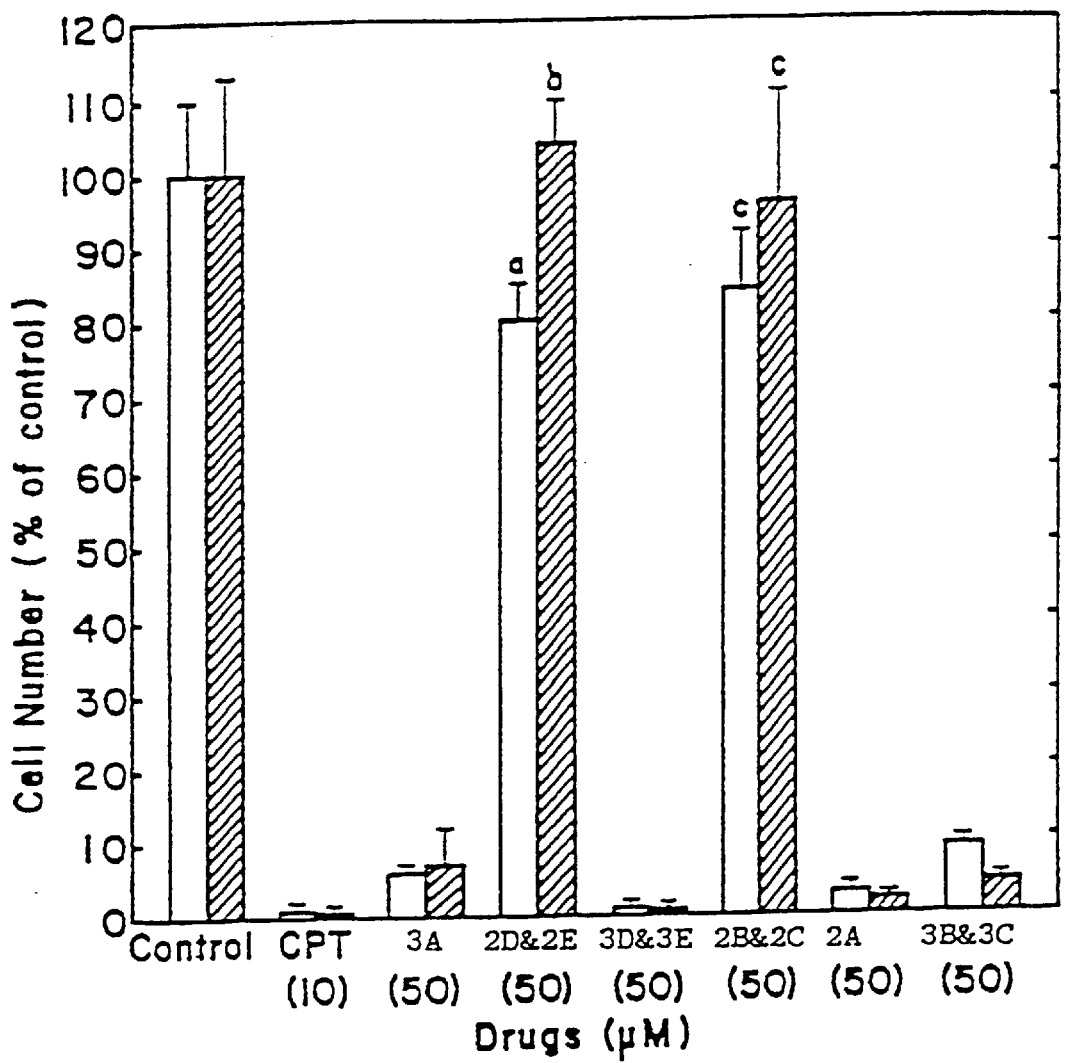
In FIG. 6, the abilities of the drugs tested in FIG. 5 to inhibit the growth of L1210 cells in vitro are compared at days 3 (open) and 4 (striped). The results are expressed as % of the numbers of vehicle-treated control cells after 3 (396,200±38,431 cells/ml; 100±10%; open) and 4 days in culture (991,907±129,245 cells/ml; 100±13% striped). Bars: means±SD (n=3). $^a$P<0.05, significantly smaller than control; $^b$not significantly different from control; $^c$not different from control or 2D & 2E.

The ability of several of the new tricyclic pyrone analogs to inhibit the growth of L1210 cells in culture was assessed and compared to that of CPT (FIGS. 5 and 6). Over a 4-day period, there is a 50-fold increase in the number of control cells grown in the absence of drugs (FIG. 5). Since 22 and 5B fail to inhibit DNA synthesis (FIG. 2), their ability to alter L1210 cell growth has not been tested. It should be noted that 50 μM 2D and 2E and 2B and 2C, which inhibit the DNA response of L1210 cells by 31–49% (FIG. 2), cannot inhibit the growth of these leukemic cells over a 4-day period (FIG. 5). The effects of 1A and 1D and 1E on L1210 cell growth, therefore, are not worth testing. Since these compounds inhibit DNA synthesis to a lesser degree than 2D and 2E and 2B and 2C (FIG. 2), they are very unlikely to significantly decrease tumor cell growth in vitro. In contrast, the same four new compounds shown to inhibit DNA synthesis by 79% or more (FIG. 2) also dramatically block the growth of L1210 cells in vitro (FIG. 5). At 50 μM, 3A, 3D and 3E, 2A and 3B and 3C all mimic the inhibition of L1210 cell growth caused by 10 μM CPT (FIG. 5). The similar magnitude of these inhibitory effects is more evident on a non-logarithmic scale. Indeed, 50 μM 3A, 3D and 3E, 2A and 3B and 3C all reduce the increasing numbers of untreated L1210 cells observed in control wells after 3 and 4 days in culture by 91–100% (FIG. 6).

Figure 7:
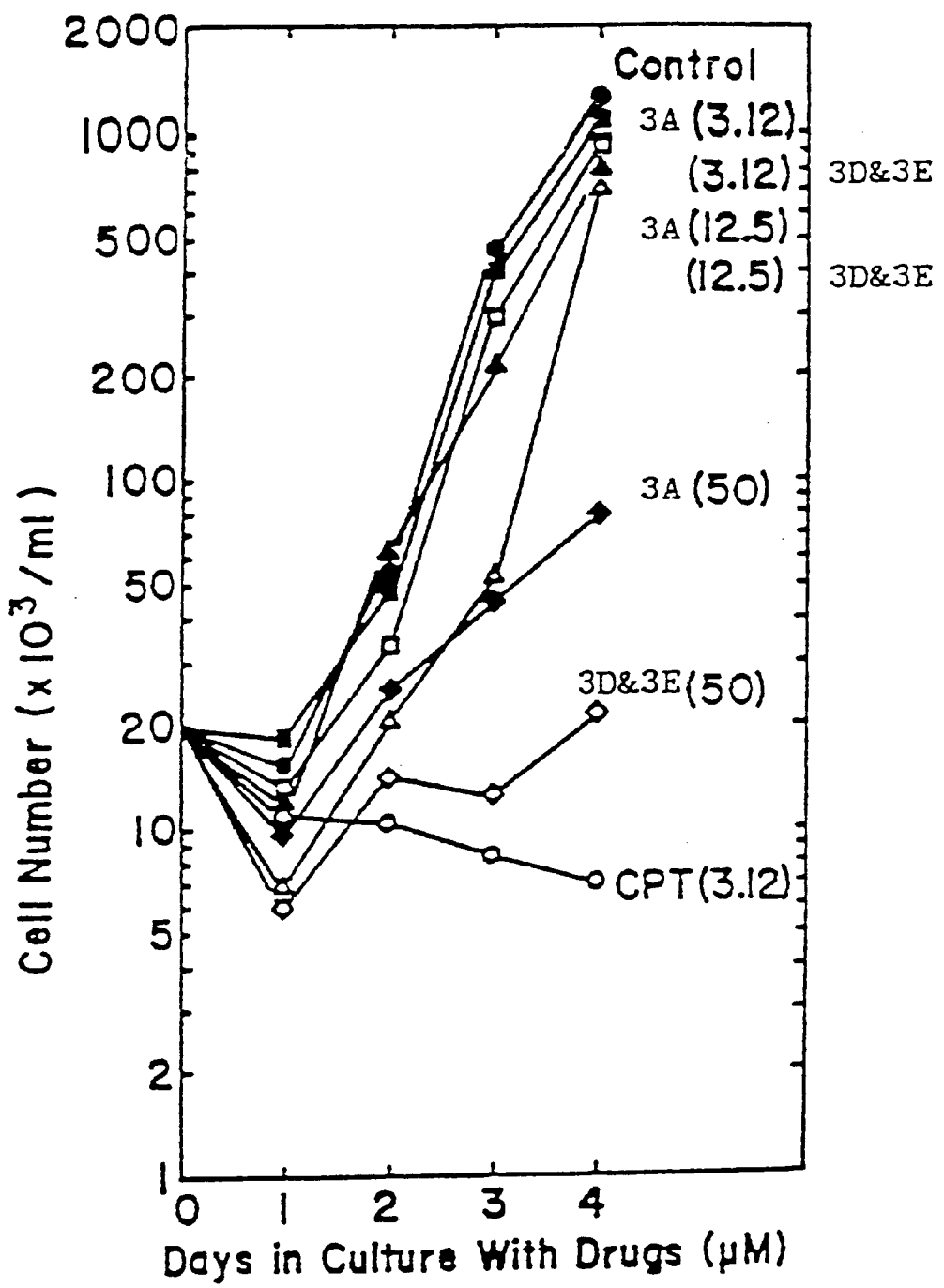
FIG. 7 shows the concentration-dependent inhibition of the growth of L1210 cells in vitro by the new tricyclic pyrone analogs 3A and 3D & 3E. The protocol of the experiment was identical to that of FIG. 5. Cells were incubated in the presence or absence (●, control) of 3.12 μM 3A (■), 3D & 3E (□) and CPT (○), 12.5 μM 3A (▲) and 3D & 3E (Δ), or 50 μM 3A (◆) and 3D & 3E (◇), and their density was monitored in triplicate every 24 hours. Cell numbers are plotted on a logarithmic scale.
Figure 8:
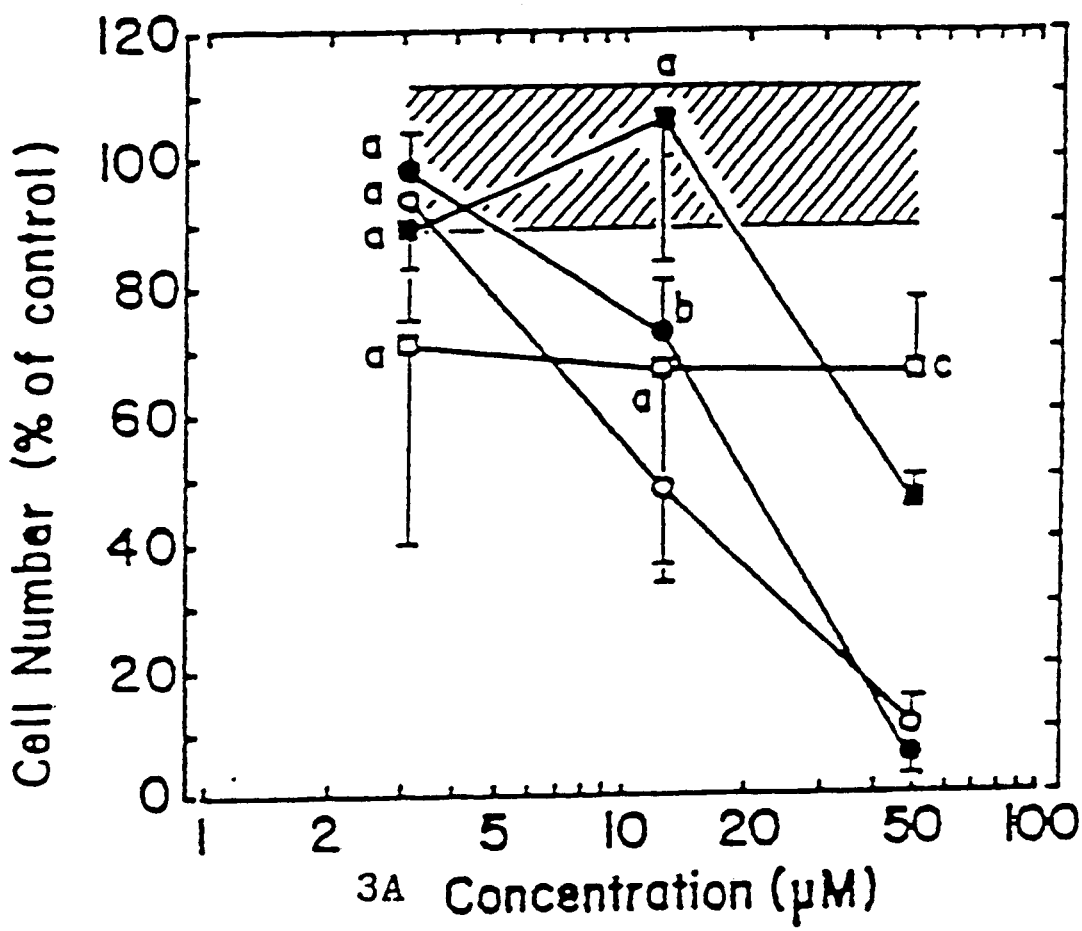
In FIG. 8 the abilities of the concentrations of 3A tested in FIG. 7 to inhibit the growth of L1210 cells in vitro are compared at days 1 (□), 2 (■), 3 (○) and 4 (●). The results are expressed as % of the numbers of vehicle-treated control cells after 1 (15,387±1,723 cells/ml), 2 (54,880±6,256 cells/ml), 3 (458,280±52,244 cells/ml), and 4 (1,185,000±125,610 cells/ml) days in culture (100±11 %; striped area). The concentrations of 3A are plotted on a logarithmic scale. Bars: means±SD (n=3). $^a$Not significantly different from control; $^b$P<0.025 and $^c$P<0.05, significantly smaller than control.
Figure 9:
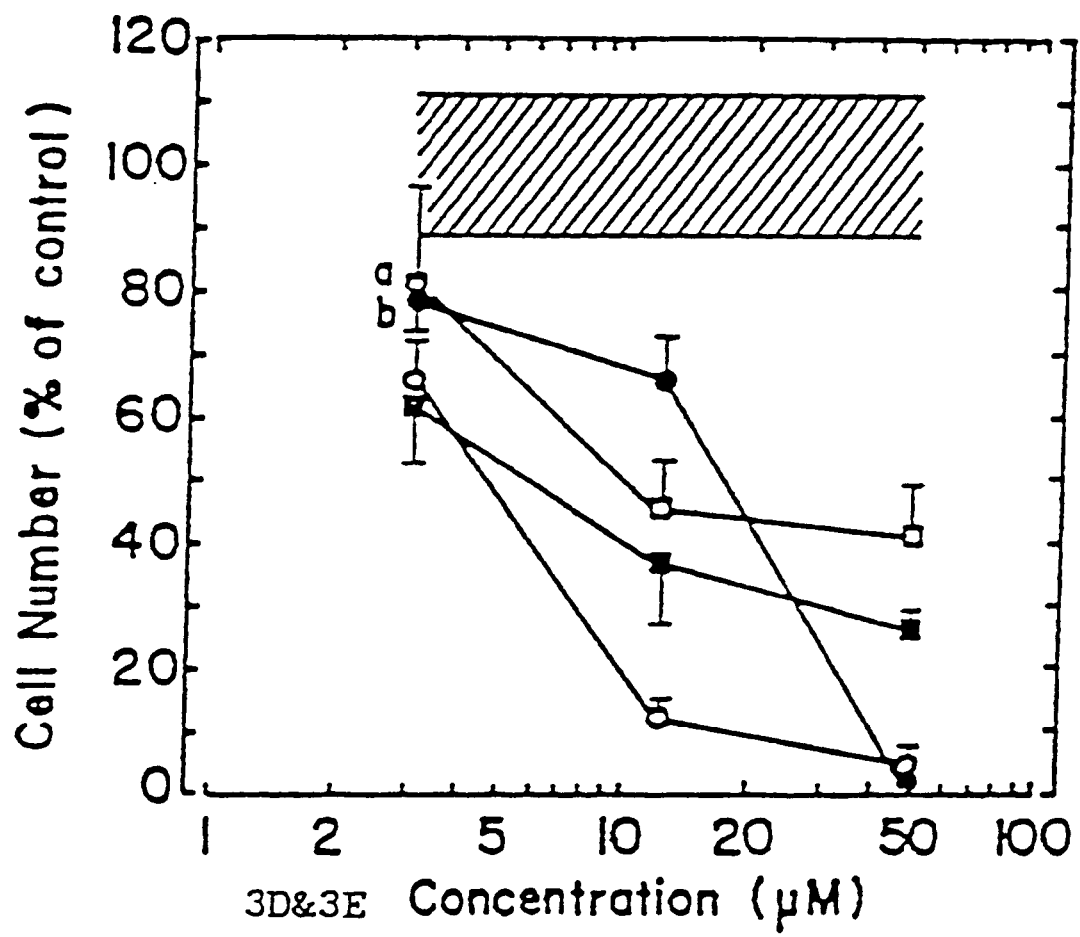
In FIG. 9, the abilities of the concentrations of 3D & 3E tested in FIG. 7 to inhibit the growth of L1210 cells in vitro are compared at days 1 (□), 2 (■), 3 (○) and 4 (●). The determination of the results was identical to that of FIG. 8. The concentrations of 3D & 3E are plotted on a logarithmic scale. Bars: means±SD (n=3). $^a$Not significantly different from control; $^b$P<0.05, significantly smaller than control.

The ability of 3A and 3D and 3E to inhibit the growth of L1210 cells in vitro is clearly concentration-dependent between 3.12 and 50 μM (FIGS. 7–9). On an equal concentration basis, 3D and 3E are slightly more effective than 3A but 50 μM concentrations of these new agents are required to match the inhibitory effect of 3.12 μM CPT. When the inhibitory effects are expressed as % of the increasing numbers of untreated cells present each day in control culture wells, the magnitudes of inhibition for each concentration of 3A and 3D and 3E generally increase over a 4-day period (FIGS. 8 and 9). Because the drugs increasingly slow down or block the rate of tumor cell growth, the difference between the number of exponentially growing control cells and the reduced number of drug-treated cells keeps increasing with the number of days in culture. This effect is even more apparent with 2A (FIGS. 10 and 11).

Figure 10:
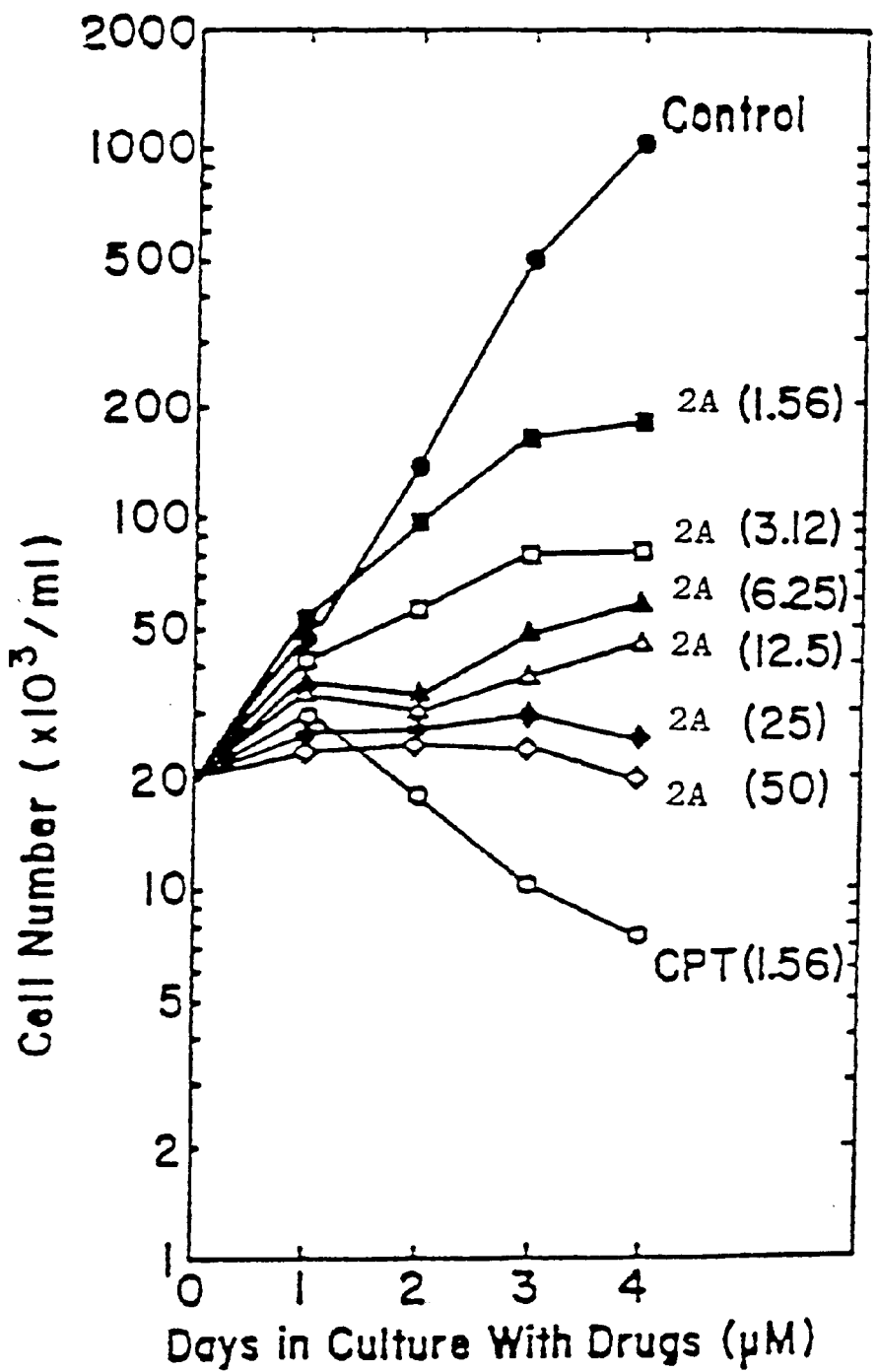
FIG. 10 shows the concentration-dependent inhibition of the growth of L1210 cells in vitro by the new tricyclic pyrone analog 2A. The protocol of the experiment was identical to that of FIG. 5. Cells were incubated in the presence or absence (●, control) of 1.56 (■), 3.12 (□), 6.25 (▲), 12.5 (Δ), 25 (◆) and 50 μM 2A (◇) or 1.56 μM CPT (○), and their density was monitored in triplicate every 24 hours. Cell numbers are plotted on a logarithmic scale.
Figure 11:
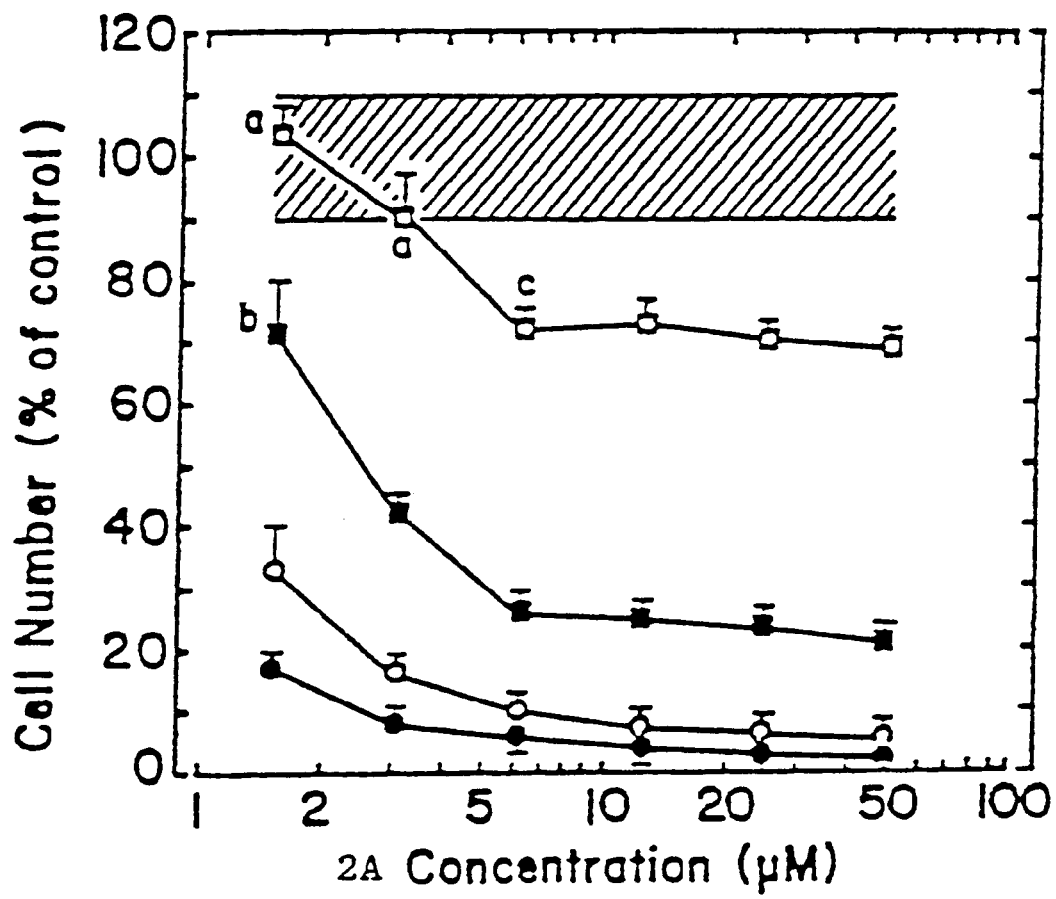
In FIG. 11, the abilities of the concentrations of 2A tested in FIG. 10 to inhibit the growth of L1210 cells in vitro are compared at days 1 (□), 2 (■), 3 (○) and 4 (●). The results are expressed as % of the numbers of vehicle-treated control cells after 1 (46,480±4,462 cells/ml), 2 (135,880±13,004 cells/mil), 3 (495,440±51,823 cells/ml), and 4 (1,009,520±103,476 cells/ml) days in culture (100±10%; striped area). The concentrations of 2A are plotted on a logarithmic scale. Bars: means±SD (n=3). $^a$Not significantly different from control; $^b$P<0.025 and $^c$P<0.005, significantly smaller than control.

The inhibition of tumor cell growth by 2A increases with the concentration tested (FIG. 10). And the effectiveness of each concentration increases with the time in culture (FIG. 11). But the shape of the concentration-response curve is similar at each time point tested. For instance, every day, the concentration-dependent inhibitory effect of 2A is maximal at 6.25 μM and plateaus thereafter (FIG. 11). However, the 6.25 μM concentration of 2A reduces the increasing numbers of untreated L1210 cells observed at 1, 2, 3 and 4 days in control wells by 28, 74, 90 and 94%, respectively (FIG. 11). These results, therefore, suggest that the effectiveness of 3A, 3D and 3E, 2A and 3B and 3C as inhibitors of tumor cell growth in vitro is a combination of drug concentration and duration of action. Obviously, concentrations of 2A much smaller than 1.56 μM should be tested since this level of drug has no effect after 24 h but inhibits tumor cell growth by 83% after 96 h (FIG. 11).

Figure 12:
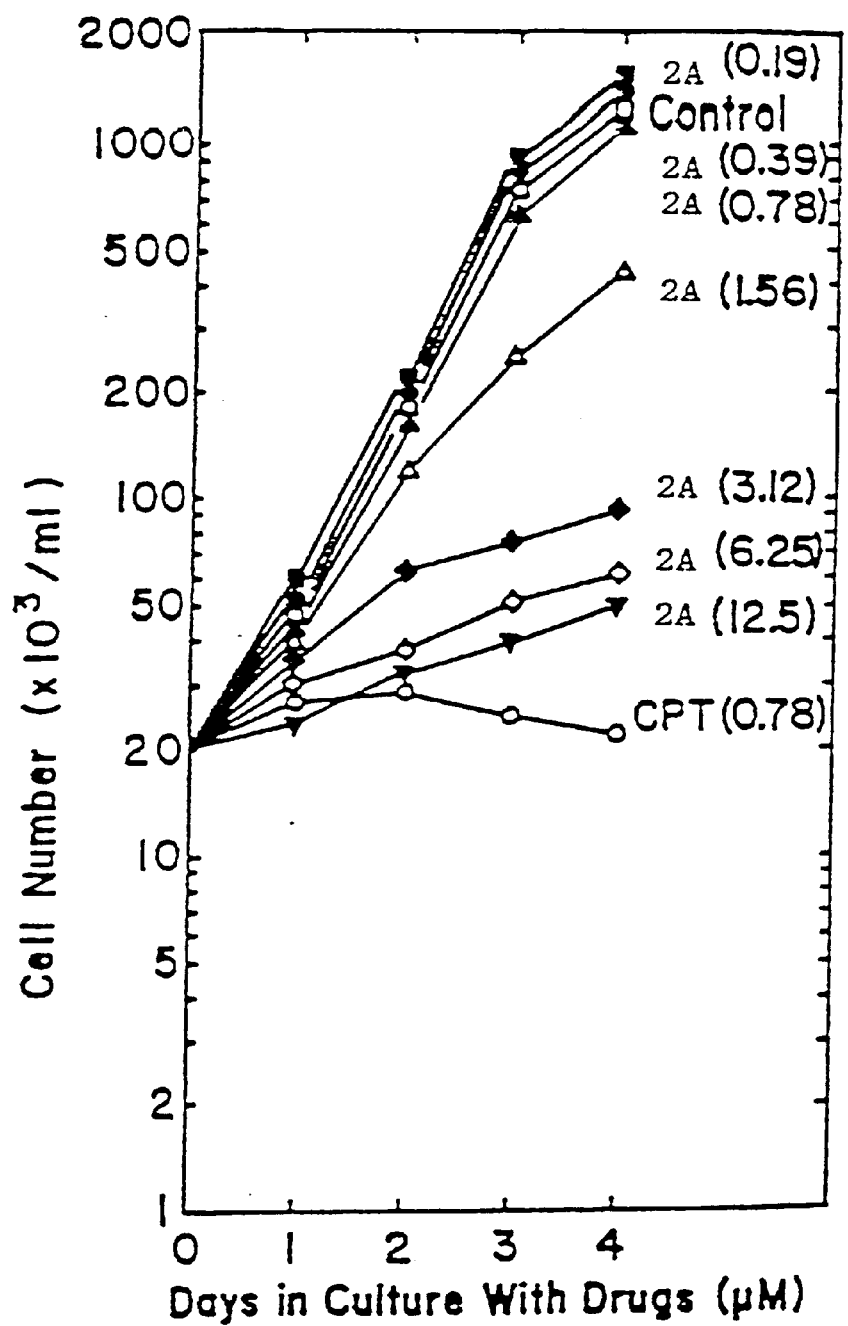
FIG. 12 shows the concentration-dependent inhibition of the growth of L1210 cells in vitro by the new tricyclic pyrone analog 2A. The protocol of the experiment was identical to that of FIG. 5. Cells were incubated in the presence or absence (●, control) of 0.19 (■), 0.39 (□), 0.78 (▲), 1.56 (Δ) 3.12 (◆), 6.25 (◇) and 12.5 μM 2A (▼) or 0.78 μM CPT (○), and their density was monitored in triplicate every 24 hours. Cell numbers are plotted on a logarithmic scale.
Figure 13:
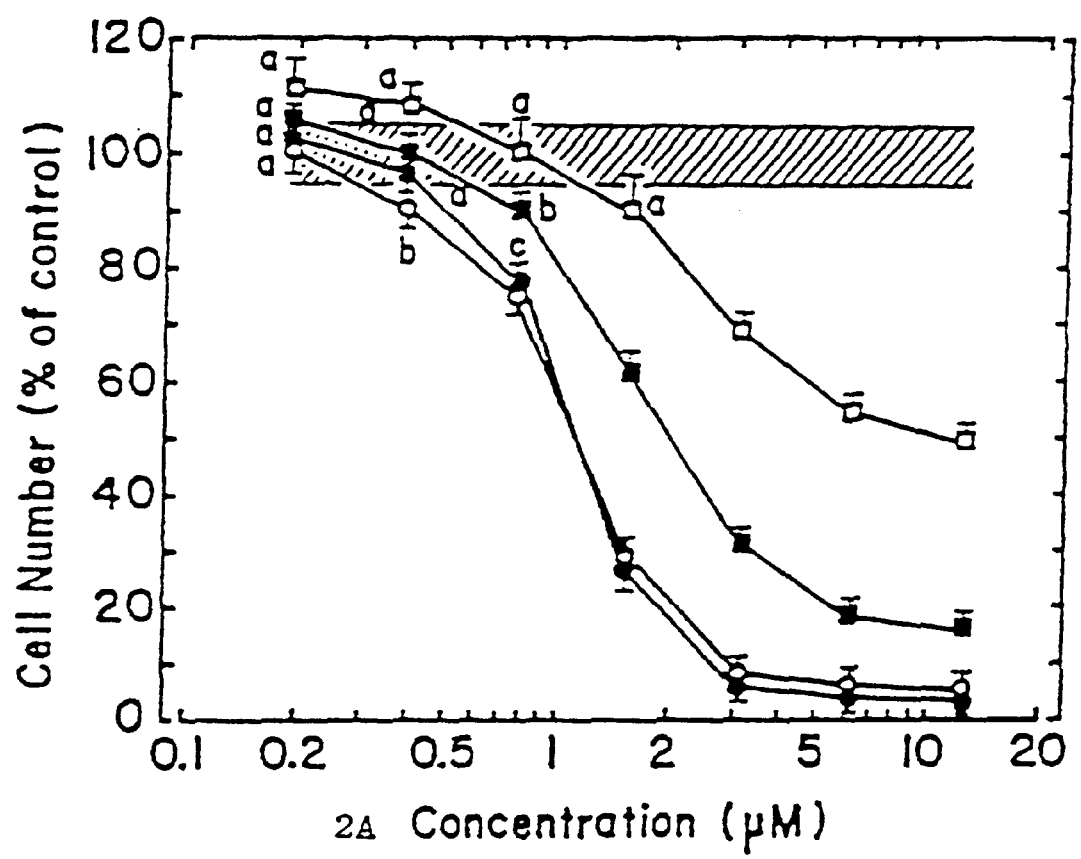
In FIG. 13, the abilities of the concentrations of 2A tested in FIG. 12 to inhibit the growth of L1210 cells in vitro are compared at days 1 (□), 2 (■), 3 (○) and 4 (●). The results are expressed as % of the numbers of vehicle-treated control cells after 1 (50,560±2,730 cells/ml), 2 (198,987±9,452 cells/ml), 3 (862,707±39,253 cells/ml) and 4 (1,655,240±86,900 cells/ml) days in culture (100±5%; striped area). The concentrations of 2A are plotted on a logarithmic scale. Bars: means±SD (n=3). $^a$Not significantly different from control; $^b$P<0.05 and $^c$P<0.005, significantly smaller than control.

Concentrations of 2A up to 8 times lower than 1.56 μM, therefore, were tested in another experiment for their ability to inhibit the growth of L1210 cells in vitro (FIGS. 12 and 13). Again, the concentration-dependent inhibitory effects of 2A (FIG. 12) clearly increase with the number of days in culture (FIG. 13). As a result, the concentrations of 2A that reduce by 50% ($lC_{50}$) the increasing numbers of untreated cells in control wells at 1, 2, 3 and 4 days are 11.0, 2.0, 1.1 and 1.1 μM, respectively (FIG. 13). Similarly, 0.78 μM CPT reduces the increasing numbers of untreated L1210 cells observed at 1, 2, 3 and 4 days in control wells by 46, 85, 97 and 99%, respectively (FIG. 13). The magnitude of this effect over a 4-day period is mimicked by 6.25 μM 2A, suggesting that this new tricyclic pyrone analog is about 8 times less potent than the anticancer drug CPT at inhibiting leukemic cell growth in vitro, an observation which is consistent with the respective potencies of 2A and CPT on DNA synthesis in the same L1210 system. The apparent discrepancy between the effects of 1.56 μM 2A on DNA synthesis (FIG. 4) and tumor cell growth (FIGS. 11 and 13) may simply be due to the fact that the incorporation of $^3$H-thymidine into DNA was determined after only 90 min of drug treatment. Longer periods of incubation prior to pulse labelling might be required to demonstrate the inhibitory effects of low concentrations of 3A, 3D & 3E, 2A and 3B & 3C on DNA synthesis.

This invention is described with reference to preferred embodiments; however, it will be apparent to those skilled in the art that additional equivalent procedures and compositions may be substituted in the practice of this invention for those disclosed herein within the scope and spirit of applicants' contribution to the art. The appended claims are to be interpreted to include all such modifications and equivalents.

We claim:

1. A compound selected from the group consisting of compounds of the formula:

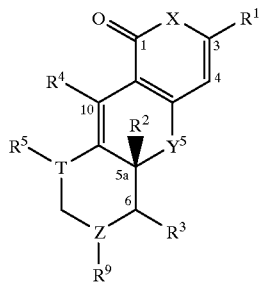

wherein:

T is independently CH, S or O;
X is independently O or S;
Y is independently O or S;
Z is independently CH, S or O;
$R^1$, $R^3$, $R^4$ and $R^5$ are, independently, H, alkyl, alkenyl, alkynyl,

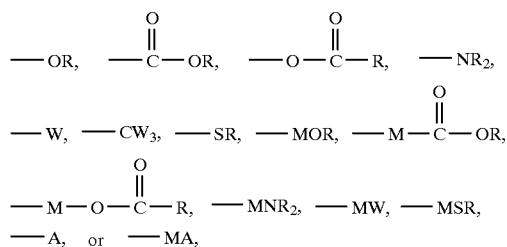

wherein R is independently H, alkyl, alkenyl or alkynyl, an aromatic ring system, amino, sulphydryl, or sulfonyl, M is a divalent alkyl, alkenyl or alkynyl, aromatic ring system, or sulfonyl, W is Cl, F, Br or OCl, and A is an aromatic ring system;

$R^2$ and $R^9$ are independently R as defined above; compounds of the formula:

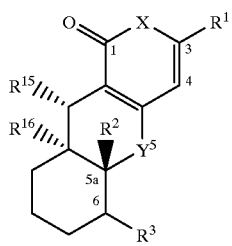

wherein:

X, Y and $R^1$–$R^3$ are as set forth above;
$R^{15}$ is independently $NH_2$, OH, or OCOR where R is H, alkyl, or aryl;
$R^{16}$ is independently OH or H; or
$R^{15}$ and $R^{16}$ taken together are O; and
compounds of the formula:

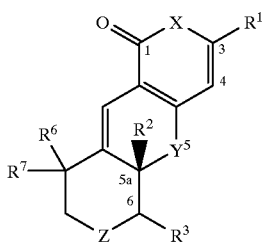

wherein:

X, Y, Z, $R^1$, $R^2$ and $R^3$ are as set forth above; and
$R^6$ is H when $R^7$ is OH, or $R^6$ is OH when $R^7$ is H, or $R^6$ and $R^7$ taken together are =O.

2. A compound of claim 1 having the formula:

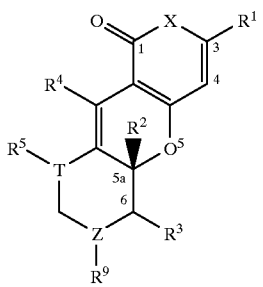

wherein:

$R^1$ is independently selected from the group consisting of R, 3-pyridyl, R-substituted 3-pyridyl, phenyl, R-substituted, di-substituted and tri-substituted phenyl, O-R-substituted, di-substituted and tri-substituted phenyl;

where R, $R^2$ and $R^9$ are, independently, H, alkyl, alkenyl or alkynyl, an aromatic ring system, amino, sulfhydryl or sulfonyl;

$R^3$ and $R^4$ and $R^5$ are independently selected from the group R, OCHO, and OR where R is as defined above; and T and Z are independently selected from the group consisting of CH, S and O.

3. A compound having the formula:

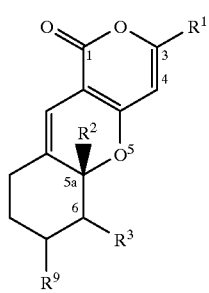

$R^1$ is independently selected from the group consisting of alkyl, 3-pyridyl and 3,4-dimethoxyphenyl;

$R^2$ is independently selected from the group consisting of H and $CH_3$;

$R^3$ is independently selected from the group of H, OH, and OCHO; and

R[9] is independently selected from the group of H and isopropenyl.

4. The compound of claim 3 wherein R[3] is an alpha substituent.

5. The compound of claim 3 wherein R[3] is a beta substituent.

6. The compound of claim 3 wherein R[1] is $CH_3$ and R[2], R[3] and R[9] are H.

7. The compound of claim 3 wherein R[1] and R[2] are $CH_3$, R[3] is selected from the group consisting of OH and OCHO, and R[9] is H.

8. The compound of claim 7 wherein R[3] is OH.

9. The compound of claim 7 wherein R[3] is OCHO.

10. The compound of claim 3 wherein R[1] is 3-pyridyl, R[2] is H or $CH_3$, and R[3] and R[9] are H.

11. The compound of claim 3 wherein R[1] is 3-pyridyl, R[2] is selected from the group consisting of H and $CH_3$, R[3] is selected from the group consisting of OH and OCHO, and R[9] is H.

12. The compound of claim 3 wherein R[1] is 3,4-dimethoxyphenyl, R[2] is selected from the group consisting of H and $CH_3$, R[3] is selected from the group consisting of OH and OCHO, and R[9] is H.

13. The compound of claim 3 wherein R[2] and R[3] are H, and R[9] is isopropenyl.

14. The compound of claim 13 wherein R[1] is $CH_3$.

15. The compound of claim 13 wherein R[1] is 3-pyridyl.

16. The compound of claim 13 wherein R[1] is 3,4 dimethoxyphenyl.

17. A compound selected from the group consisting of 3-(3-pyridyl)-1H-5a,6,7,8,9-pentahydro-1-oxopyrano[4,3-b]benzopyran; 3-(3,4-dimethoxyphenyl)-1H-5a,6,7,8,9-pentahydro-1-oxopyrano[4,3-b]benzopyran; cis- and trans-3-(3,4-dimethoxyphenyl)-5 a-methyl-6-formyloxy-1H-5a,6,7,8,9-pentahydro-1-oxopyrano[4,3-b]benzopyran; cis- and trans-3-(3-pyridyl)-5a-methyl-6-formyloxy-1H-5a,6,7,8,9-pentahydro-1-oxopyrano[4,3-b]benzopyran; cis- and trans-3-(3,4-dimethoxyphenyl)-5a-methyl-6-hydroxy-1H-5a,6,7,8,9-pentahydro-1-oxopyrano[4,3-b]benzopyran; 3-methyl-1H-5a,6,7,8,9-pentahydro-1-oxopyrano[4,3-b]benzopyran; cis- and trans-3-5a-dimethyl-6-formyloxy-1H-5a,6,7,8,9-pentahydro-1-oxopyrano[4,3-b]benzopyran; cis- and trans-3-(3-pyridyl)-5a-methyl-6-hydroxy-1H-5a,6,7,8,9-pentahydro-1-oxopyrano[4,3-b]benzopyran; 3-(Methoxycarbonylmethyl)-1H-5a,6,7,8,9-pentahydro-1-oxopyrano [4,3-b][1]benzopyran; 3-(Carboxymethyl)-1H-5a,6,7,8,9-pentahydro-1-oxopyrano [4,3-b][1]benzopyran; (5aS*, 9aS*, 10S*)-9a,10-Epoxy-3-(3-pyridyl)-1H-5a,6,7,8,9,a, 10-heptahydro-1-oxopyrano[4,3-b][1]benzopyran; and (5aS*,9aR*,10R*)-9a,10-Dihydroxy-3-(3-pyridyl)-1H-5a, 6,7,8,9,9a, 10-heptahydro-1-oxopyrano[4,3-b][1] benzopyran.

18. A compound selected from the group consisting of 3-(3-pyridyl)-1H-5a,6,7,8,9-pentahydro-1-oxopyrano[4,3-b]benzopyran; 3-(3,4-dimethoxyphenyl)-1H-5a,6,7,8,9-pentahydro-1-oxopyrano[4,3-b]benzopyran; cis- and trans-3-(3,4-dimethoxyphenyl)-5a-methyl-6-formyloxy-1H-5a,6,7,8,9-pentahydro-1-oxopyrano[4,3-b]benzopyran; cis- and trans-3-(3-pyridyl)-5a-methyl-6-formyloxy-1H-5a,6,7,8,9-pentahydro-1-oxopyrano[4,3 -b]benzopyran; cis- and trans-3-(3,4-dimethoxyphenyl)-5a-methyl-6-hydroxy-1H-5a,6,7,8,9-pentahydro-1-oxopyrano[4,3-b]benzopyran; and cis- and trans-3-(3-pyridyl)-5a-methyl-6-hydroxy-1H-5a,6,7,8,9-pentahydro-1-oxopyrano[4,3-b]benzopyran.

19. A compound selected from the group consisting of 3-(3-pyridyl)-1H-5a,6,7,8,9-pentahydro-1-oxopyrano[4,3-b]benzopyran; 3-(3,4-dimethoxyphenyl)-1H-5a,6,7,8,9-pentahydro-1-oxopyrano[4,3-b]benzopyran; cis- and trans-3-(3,4-dimethoxyphenyl)-5a-methyl-6-formyloxy-1H-5a,6,7,8,9-pentahydro-1-oxopyrano[4,3-b]benzopyran; and cis- and trans-3-(3-pyridyl)-5a-methyl-6-hydroxy-1H-5a,6,7,8,9-pentahydro-1-oxopyrano[4,3-b]benzopyran.

20. 1,8-Di-{3-[1H-5a,6,7,8,9-pentahydro-1-oxopyrano[4,3-b][1]benzopyranyl]}-2,7-octanedione.

21. A compound of claim 1 selected from the group consisting of (5aS, 7S)-7-Isopropenyl-3-methyl-1H-5a,6,7,8,9-pentahydro-1-oxopyrano [4,3-b][1] benzopyran; (5aS, 7S)-7-Isopropenyl-3-(3-pyridyl)-1H-5a,6,7,8,9-pentahydro-1-oxopyrano [4,3-b][1]benzopyran; (5aS, 7S)-7-Isopropenyl-3-(3,4-dimethoxyphenyl)-1H-5a,6,7,8,9-pentahydro-1-oxopyrano[4,3-b][1]benzopyran; (5aS,7S)-7-[2-(1-hydroxypropyl)]-3-methyl-1H-5a,6,7,8,9-pentahydro-1-oxopyrano [4,3-b][1]benzopyran; (5aS,7S)-7-[1-(Formyl)ethyl]-3-methyl-1H-5a,6,7,8,9-pentahydro-1-oxopyrano [4,3-b][1]benzopyran; (5aS, 7S)-7-[2-(1-Hydroxypropyl)]-10-hydroxy-3-(3,4-dimethoxyphenyl)-1H-Sa,6,7,8,9,9a,10-heptahydro-1-oxopyrano [4,3-b][1]benzopyran; and (5aS, 7S)-7-[2-(1-Pentanoyloxypropyl)]-10-hydroxy-3-(3,4-dimethoxyphenyl)-1H-5a,6,7,8,9,9a,10-heptahydro-1-oxopyrano [4,3-b][1]benzopyran.

22. A method of making a compound of claim 1 comprising contacting:

(a) a compound of the formula:

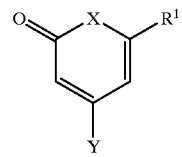

wherein X and R[1] are as defined in claim 1; and

Y is OH or SH; with (b) a compound having an aldehyde substituent of the formula:

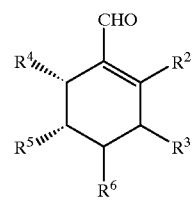

wherein:

R[2], R[3], R[4], and R[5] are as defined in claim 1 and R[6] is defined as R[1] in claim 1; and T and Z are independently selected from the group consisting of CH, S and O, under reaction conditions whereby a condensation reaction takes place between said compounds of paragraphs (a) and (b) whereby group Y reacts with said aldehyde substituent to form said compound of claim 1.

23. A method of making a compound of claim 2 comprising contacting:

(a) a compound of the formula:

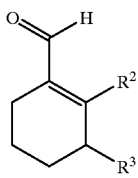

wherein:
R² is H, alkyl, alkenyl or alkynyl, an aromatic ring system, amino, sulfhydryl, or sulfonyl; and
R³ is independently selected from the group R, OCHO, and OR, where R is, independently, H, alkyl, alkenyl or alkynyl, an aromatic ring system, amino, sulfhydryl or sulfonyl;
with
(b) a compound of the formula:

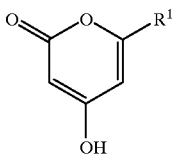

R¹ is as defined in claim 2.

24. A method of inhibiting macromolecule synthesis in cancer cells in a patient comprising administering to said patient an effective amount of a compound of claim 1.

25. A method of inhibiting macromolecule synthesis in cancer cells in a patient comprising administering to said patient an effective amount of a compound of claim 2.

26. A method of inhibiting macromolecule synthesis in cancer cells in a patient comprising administering to said patient an effective amount of a compound of claim 17.

27. A method of inhibiting tubulin polymerization in a patient comprising administering to said patient an effective amount of a compound of claim 1.

28. A method of inhibiting cancer cell growth in a patient having cancer comprising administering to said patient an effective amount of a compound of claim 1.

29. A method of inhibiting acetylcholinesterase in a patient suffering from Alzheimer's disease comprising administering to said patient an effective amount of a compound of claim 1.

30. A method of inhibiting cholesterol acetyltransferase in a patient suffering from atherosclerosis or hypercholesterolemia comprising administering to said patient an effective amount of a compound of claim 1.

* * * * *

UNITED STATES PATENT AND TRADEMARK OFFICE
CERTIFICATE OF CORRECTION

PATENT NO. : 5,958,970

DATED : Sep. 28, 1999

INVENTOR(S) : Hua et al.

It is certified that error appears in the above-identified patent and that said Letters Patent is hereby corrected as shown below:

At column 1, lines 16 and 22, both occurrences, please rewrite "Penicillium" as --*Penicillium*--.

At column 3, structure II, please replace

"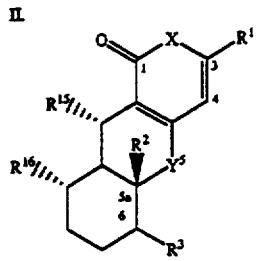"

with

-- II. 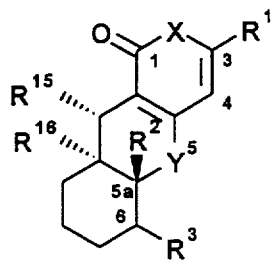 --

UNITED STATES PATENT AND TRADEMARK OFFICE
CERTIFICATE OF CORRECTION

PATENT NO. : 5,958,970

DATED : Sep. 28, 1999

INVENTOR(S) : Hua et al.

It is certified that error appears in the above-identified patent and that said Letters Patent is hereby corrected as shown below:

At column 6, line 9, please rewrite "1H-7,8,9,10-tetrahydro-1-oxopyrano[4,3-c]isoquinoline" as --1H-3-methyl-7,8,9,10-tetrahydropyrano[4,3-c]isoquinolin-1-one--.

At column 6, line 56, please rewrite "[4,3b]benzopyran" as --[4,3-b]benzopyran--.

At column 7, lines 13, and 14, please rewrite "1H-7,8,9,10-tetrahydro-1-oxopyrano[4,3-c]isoquinoline" as --1H-3-methyl-7,8,9,10-tetrahydropyrano[4,3-c]isoquinolin-1-one--.

At column 8, line 24, please rewrite "T÷#CH, Z÷CH, $R^4$÷H, or $R^5$÷H" as --T≠CH, Z≠CH, $R^4$≠H, or $R^5$≠H--.

At column 12, line 38, please rewrite "cells/mil)," as --cells/mL),--.

At column 14, last structure on the page, please add the label --5B--.

At column 15, line 5, please delete "5B".

UNITED STATES PATENT AND TRADEMARK OFFICE
CERTIFICATE OF CORRECTION

PATENT NO. : 5,958,970                  Page 3 of 16

DATED      : Sep. 28, 1999

INVENTOR(S) : Hua et al.

It is certified that error appears in the above-identified patent and that said Letters Patent is hereby corrected as shown below:

At column 15, line 5, please replace

" 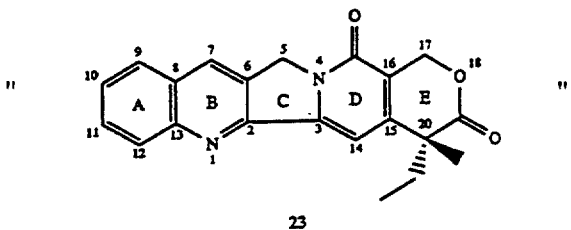 "

with

-- 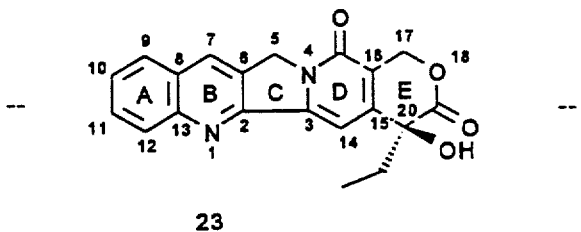 --

UNITED STATES PATENT AND TRADEMARK OFFICE
CERTIFICATE OF CORRECTION

PATENT NO. : 5,958,970

DATED : Sep. 28, 1999

INVENTOR(S) : Hua et al.

It is certified that error appears in the above-identified patent and that said Letters Patent is hereby corrected as shown below:

At column 16, line 27, please rewrite "13C NMR," as --$^{13}$C NMR--.

At column 19, line 14, please delete "☐".

At column 20, line 5, please rewrite "E. A" as --II. A--.

At column 24, first equation product, please replace

" 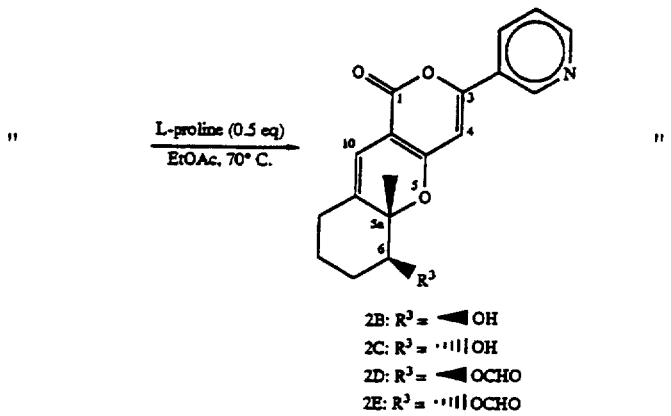 "

UNITED STATES PATENT AND TRADEMARK OFFICE
CERTIFICATE OF CORRECTION

PATENT NO. : 5,958,970

DATED : Sep. 28, 1999

INVENTOR(S) : Hua et al.

It is certified that error appears in the above-identified patent and that said Letters Patent is hereby corrected as shown below:

with

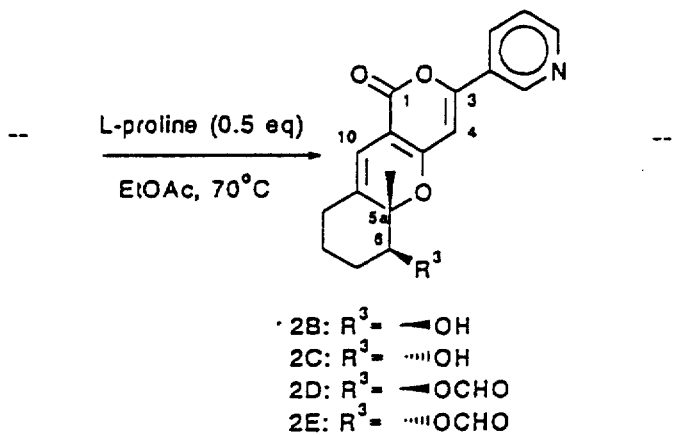

UNITED STATES PATENT AND TRADEMARK OFFICE
CERTIFICATE OF CORRECTION

PATENT NO. : 5,958,970

DATED : Sep. 28, 1999

INVENTOR(S) : Hua et al.

It is certified that error appears in the above-identified patent and that said Letters Patent is hereby corrected as shown below:

At column 24, second equation product, please replace

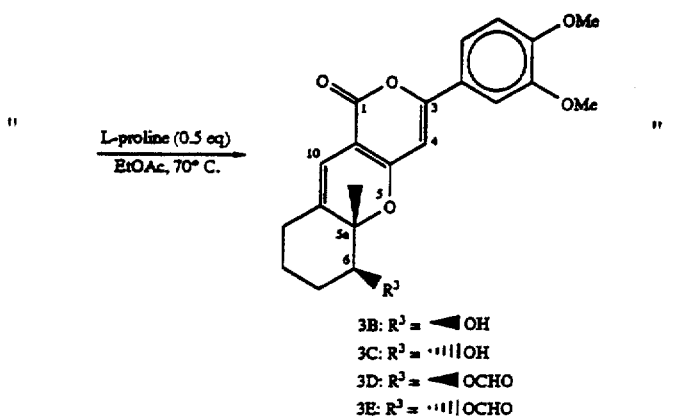

UNITED STATES PATENT AND TRADEMARK OFFICE
CERTIFICATE OF CORRECTION

PATENT NO. : 5,958,970

DATED : Sep. 28, 1999

INVENTOR(S) : Hua et al.

It is certified that error appears in the above-identified patent and that said Letters Patent is hereby corrected as shown below:

with

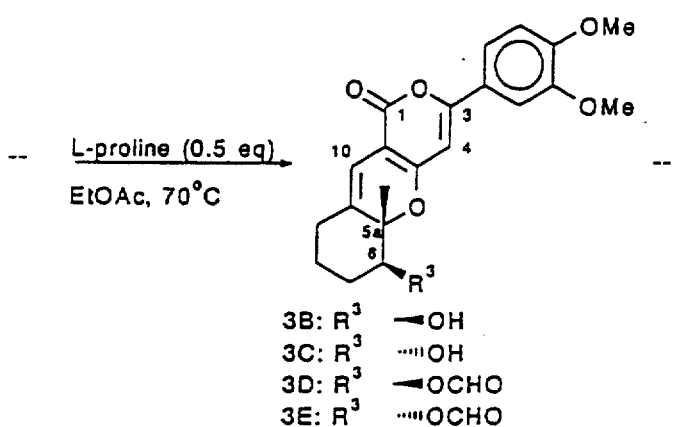

UNITED STATES PATENT AND TRADEMARK OFFICE
CERTIFICATE OF CORRECTION

PATENT NO. : 5,958,970

DATED : Sep. 28, 1999

INVENTOR(S) : Hua et al.

It is certified that error appears in the above-identified patent and that said Letters Patent is hereby corrected as shown below:

At column 27, please replace

"
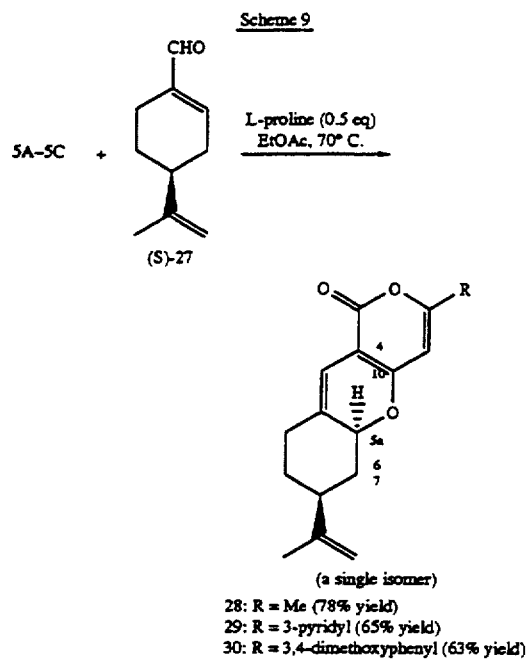
"

UNITED STATES PATENT AND TRADEMARK OFFICE
CERTIFICATE OF CORRECTION

PATENT NO. : 5,958,970

DATED : Sep. 28, 1999

INVENTOR(S) : Hua et al.

It is certified that error appears in the above-identified patent and that said Letters Patent is hereby corrected as shown below:

with

--

Scheme 9

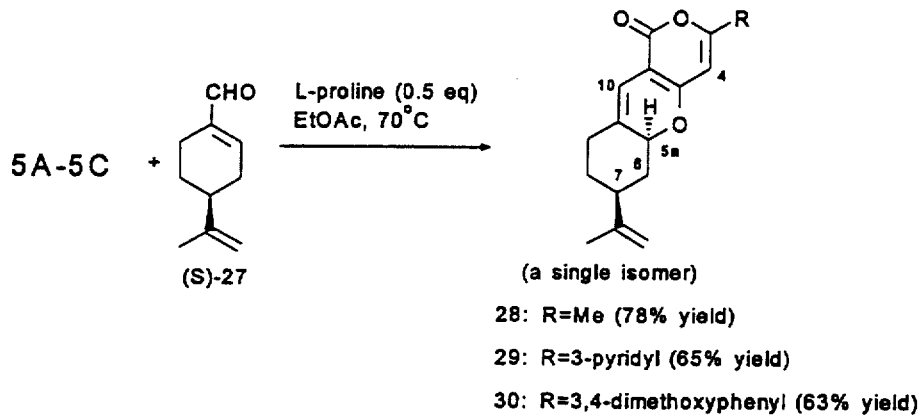

28: R=Me (78% yield)

29: R=3-pyridyl (65% yield)

30: R=3,4-dimethoxyphenyl (63% yield)

--

UNITED STATES PATENT AND TRADEMARK OFFICE
CERTIFICATE OF CORRECTION

PATENT NO. : 5,958,970

DATED : Sep. 28, 1999

INVENTOR(S) : Hua et al.

It is certified that error appears in the above-identified patent and that said Letters Patent is hereby corrected as shown below:

At column 28, please replace

"
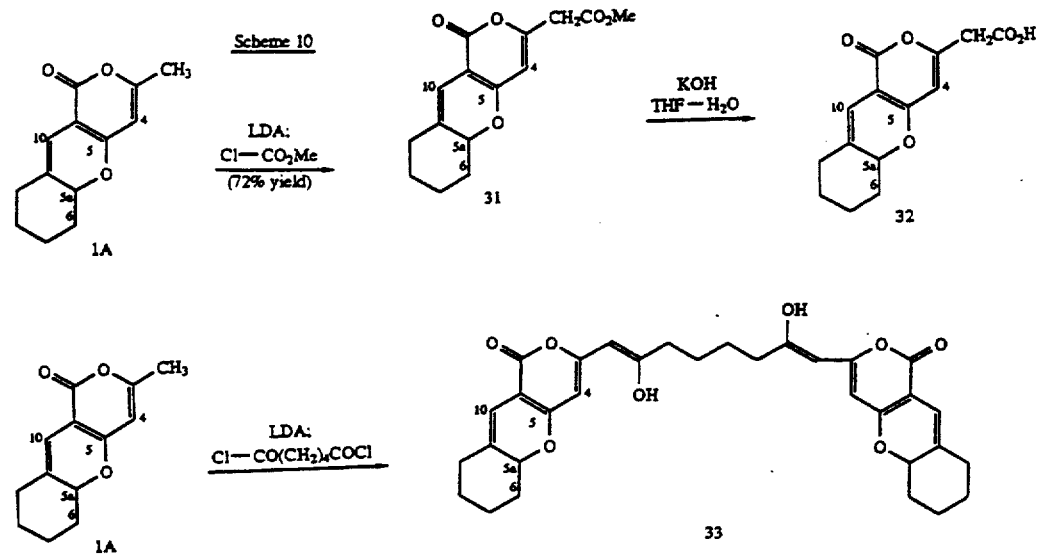
"

UNITED STATES PATENT AND TRADEMARK OFFICE
CERTIFICATE OF CORRECTION

PATENT NO. : 5,958,970

DATED : Sep. 28, 1999

INVENTOR(S) : Hua et al.

It is certified that error appears in the above-identified patent and that said Letters Patent is hereby corrected as shown below:

with

-- Scheme 10

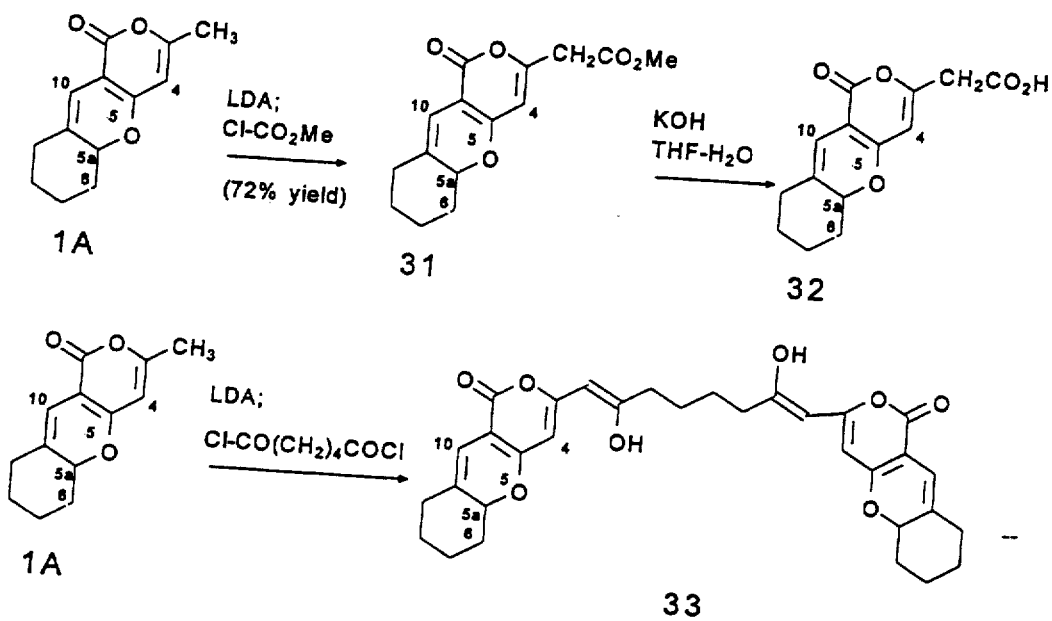

UNITED STATES PATENT AND TRADEMARK OFFICE
CERTIFICATE OF CORRECTION

PATENT NO. : 5,958,970

DATED : Sep. 28, 1999

INVENTOR(S) : Hua et al.

It is certified that error appears in the above-identified patent and that said Letters Patent is hereby corrected as shown below:

At column 31, line 30, please rewrite "6-monomnethylated" as --6-monomethylated--.

At column 34, line 21, please rewrite "2.292.23" as --2.29 - 2.23--.

At column 36, line 2, please rewrite "13C" as --$^{13}$C--.

At column 39, line 31, please rewrite "mmnol" as --mmol--.

At column 39, line 49, please rewrite "[4,3b]-[1]benzopyran" as --[4,3-b][1]benzopyran--

At column 39, line 52, please rewrite "chroinatographic" as --chromatographic--.

At column 39, line 62, please rewrite "CS')" as --C5')--.

At column 40, line 8, please rewrite "ininol" as --mmol--.

At column 40, line 58, please rewrite "[4,3b]" as --[4,3-b]--.

At column 40, line 60, please rewrite "SC" as --5C--.

At column 40, line 62, please rewrite "chromnatographic" as --chromatographic--.

UNITED STATES PATENT AND TRADEMARK OFFICE
CERTIFICATE OF CORRECTION

PATENT NO. : 5,958,970

DATED : Sep. 28, 1999

INVENTOR(S) : Hua et al.

It is certified that error appears in the above-identified patent and that said Letters Patent is hereby corrected as shown below:

At column 41, line 1, please rewrite "1.82(I," as --1.82(m,--.

At column 41, line 8, please rewrite "C1OH)," as --C10H),--.

At column 41, line 10, please rewrite "2.42 (1 H)," as --2.42 (m,1H),--.

At column 41, line 49, please rewrite "C1OH)," as --C10H),--.

At column 41, line 52, please rewrite "398 M+)." as --398 (M+).--.

At column 41, lines 54 and 55, please rewrite "1H-7,8,9,10-tetrahydro-1-oxopyrano[4,3-c]isoguinoline" as --1H-3-methyl-7,8,9,10-tetrahydropyrano[4,3-c]isoquinolin-1-one--.

At column 41, line 58, please rewrite "10-cainphorsulfonic" as --10-camphorsulfonic--.

At column 41, line 64, please rewrite "acetate-" as --acetate --.

At column 42, line 4, please rewrite "CO H)," as --C10 H)--.

At column 42, line 19, please rewrite "CH2" as --$CH_2$--.

At column 42, line 49, please rewrite "(In," as --(m,--.

UNITED STATES PATENT AND TRADEMARK OFFICE
CERTIFICATE OF CORRECTION

PATENT NO. : 5,958,970

DATED : Sep. 28, 1999

INVENTOR(S) : Hua et al.

It is certified that error appears in the above-identified patent and that said Letters Patent is hereby corrected as shown below:

At column 42, line 60, please rewrite "[4,3b]" as --[4,3-b]--.

At column 43, line 3, please rewrite "of in," as --of m,--.

At column 43, line 57, please rewrite "4,3-b]" as --[4,3-b]--.

At column 43, line 59, please rewrite "similar" as --similar--.

At column 44, lines 11 and 58, both occurrences, please rewrite "BH$_3$.THF" as --BH$_3$•THF--.

At column 45, line 49, please rewrite "HCI" as --HCl--.

At column 46, line 31, please rewrite "4,4a5,8" as --4,4a,5,8--.

At column 50, lines 17 and 18, please rewrite "OD340 nm," as --OD$_{340nm}$--.

At column 53, line 42, claim 1, please rewrite "sulphydryl," as --sulfhydryl,--.

At column 54, first line of claim 2, please delete "of claim 1".

At column 55, line 49, claim 17, please rewrite "9,a," as --9a,--.

At column 56, line 21, claim 21, please rewrite "1H-Sa,6,7,8," as --1H-5a,6,7,8,--.

UNITED STATES PATENT AND TRADEMARK OFFICE
CERTIFICATE OF CORRECTION

PATENT NO. : 5,958,970

DATED : Sep. 28, 1999

INVENTOR(S) : Hua et al.

It is certified that error appears in the above-identified patent and that said Letters Patent is hereby corrected as shown below:

At column 56, line 45, claim 22, please replace

"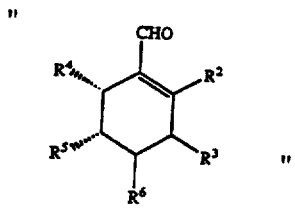"

with

--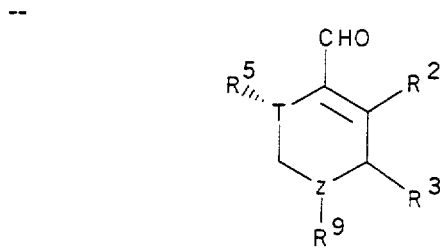--

UNITED STATES PATENT AND TRADEMARK OFFICE
CERTIFICATE OF CORRECTION

PATENT NO. : 5,958,970

DATED : Sep. 28, 1999

INVENTOR(S) : Hua et al.

It is certified that error appears in the above-identified patent and that said Letters Patent is hereby corrected as shown below:

At column 56, line 56, claim 22, please delete "$R^4$," and replace "$R^6$" with --$R^9$--.

At column 57, claim 23, please insert --wherein:-- after the last structure and just before the last line of the column.

Signed and Sealed this

Fourteenth Day of November, 2000

Attest:

Q. TODD DICKINSON

*Attesting Officer*  *Director of Patents and Trademarks*